(12) United States Patent
Fisher

(10) Patent No.: US 10,245,380 B2
(45) Date of Patent: Apr. 2, 2019

(54) CONTAINER CLOSURE, CONTAINER ASSEMBLY AND METHOD FOR UTILIZING THE SAME

(71) Applicant: William Beaumont Hospital, Royal Oak, MI (US)

(72) Inventor: Sally Ann Fisher, Clawson, MI (US)

(73) Assignee: William Beaumont Hospital, Royal Oak, MI (US)

( * ) Notice: Subject to any disclaimer, the term of this patent is extended or adjusted under 35 U.S.C. 154(b) by 396 days.

(21) Appl. No.: 15/108,020

(22) PCT Filed: Dec. 19, 2014

(86) PCT No.: PCT/US2014/071550
§ 371 (c)(1),
(2) Date: Jun. 24, 2016

(87) PCT Pub. No.: WO2015/100169
PCT Pub. Date: Jul. 2, 2015

(65) Prior Publication Data
US 2016/0325043 A1    Nov. 10, 2016

Related U.S. Application Data

(60) Provisional application No. 61/964,205, filed on Dec. 27, 2013.

(51) Int. Cl.
*A61B 19/00* (2006.01)
*A61M 5/178* (2006.01)
(Continued)

(52) U.S. Cl.
CPC ........ *A61M 5/1782* (2013.01); *A61M 5/3205* (2013.01); *B01L 3/502* (2013.01);
(Continued)

(58) Field of Classification Search
CPC ... A61M 5/1782; A61M 5/3205; B01L 3/502; B01L 3/508; B01L 3/50825; B65D 51/002; B65D 51/2807
See application file for complete search history.

(56) References Cited

U.S. PATENT DOCUMENTS 396,110 A    1/1889    Parks
502,840 A    8/1893    Ward
(Continued)

FOREIGN PATENT DOCUMENTS

EP    0327519 A1    8/1989
WO    199218844 A1    10/1992
(Continued)

OTHER PUBLICATIONS

PCT/US2014/071550 International Search Report and Written Opinion dated Apr. 17, 2015.
(Continued)

*Primary Examiner* — Ariana Zimbouski
(74) *Attorney, Agent, or Firm* — Honigman LLP; Douglas H. Siegel; Jonathan P. O'Brien

(57) ABSTRACT

A container closure ($14, 14^1, 14^2, 14^3, 14^4, 14^5, 14^6$) is disclosed. The container closure ($14, 14^1, 14^2, 14^3, 14^4, 14^5, 14^6$) includes a fluid-drawing member ($42, 42^1, 42^2, 42^3, 42^4, 42^5, 42^6$) that extends axially away from and is integral with the inner surface ($28_I, 28_I^1, 28_I^2, 28_I^3, 28_I^4, 28_I^5, 28_I^6$) of the end wall ($28, 28^1, 28^2, 28^3, 28^4, 28^5, 28^6$) of the container closure ($14, 14^1, 14^2, 14^3, 14^4, 14^5, 14^6$). A container assembly ($10, 10^1, 10^2, 10^3, 10^4, 10^5, 10^6$) is also disclosed. The container assembly ($10, 10^1, 10^2, 10^3, 10^4, 10^5, 10^6$) includes the container closure ($14, 14^1, 14^2, 14^3, 14^4, 14^5, 14^6$) and a container ($12, 12^1, 12^2, 12^3, 12^4, 12^5, 12^6$) connected to the container closure ($14, 14^1, 14^2, 14^3$, (Continued)

$14^4$, $14^5$, $14^6$). A method for utilizing the container assembly (10, $10^1$, $10^2$, $10^3$, $10^4$, $10^5$, $10^6$) is also disclosed.

35 Claims, 49 Drawing Sheets

(51) Int. Cl.
*B65D 51/28* (2006.01)
*B01L 3/00* (2006.01)
*A61M 5/32* (2006.01)
*B65D 51/00* (2006.01)
*A61M 5/00* (2006.01)

(52) U.S. Cl.
CPC ............ *B01L 3/508* (2013.01); *B01L 3/50825* (2013.01); *B65D 51/002* (2013.01); *B65D 51/2807* (2013.01); *A61M 5/008* (2013.01); *A61M 5/3213* (2013.01); *B01L 2200/025* (2013.01); *B01L 2200/026* (2013.01); *B01L 2200/141* (2013.01); *B01L 2300/021* (2013.01); *B01L 2300/042* (2013.01); *B01L 2300/043* (2013.01); *B01L 2300/044* (2013.01); *B01L 2300/046* (2013.01); *B01L 2300/0803* (2013.01); *B01L 2300/0832* (2013.01); *B01L 2300/0848* (2013.01); *B01L 2300/0851* (2013.01); *B01L 2300/0858* (2013.01); *B01L 2300/12* (2013.01)

(56) References Cited

U.S. PATENT DOCUMENTS

| | | |
|---|---|---|
| 1,219,937 A | 3/1917 | Green |
| 4,303,071 A | 12/1981 | Smith |
| 5,102,408 A | 4/1992 | Hamacher |
| 5,106,379 A | 4/1992 | Leap |
| 5,135,508 A | 8/1992 | Vernamonti |
| 5,290,256 A | 3/1994 | Weatherford et al. |
| 5,328,041 A | 7/1994 | Hook et al. |
| 5,403,288 A | 4/1995 | Stanners |
| 5,429,803 A * | 7/1995 | Guirguis ............ A61B 10/007 422/419 |
| 5,433,330 A | 7/1995 | Yatsko et al. |
| 5,454,409 A | 10/1995 | McAffer et al. |
| RE35,167 E | 3/1996 | Mouchawar et al. |
| 5,527,294 A | 6/1996 | Weatherford et al. |
| 5,573,525 A | 11/1996 | Watson et al. |
| 5,603,436 A * | 2/1997 | Leoncavallo ...... B65D 47/0885 222/212 |
| 5,681,742 A | 10/1997 | Merskelly et al. |
| 5,833,213 A | 11/1998 | Ryan |
| 5,924,584 A | 7/1999 | Hellstrom et al. |
| D418,222 S | 12/1999 | Pellow |
| 6,056,135 A | 5/2000 | Widman |
| 6,189,580 B1 * | 2/2001 | Thibault ............... A61J 1/2096 141/25 |
| 6,648,858 B2 | 11/2003 | Asbaghi |
| 6,716,396 B1 | 4/2004 | Anderson et al. |
| 6,806,094 B2 | 10/2004 | Anderson et al. |
| 6,893,612 B2 | 5/2005 | Kacian et al. |
| 7,294,308 B2 * | 11/2007 | Kacian ............... B01L 3/50825 422/534 |
| 7,322,969 B2 | 1/2008 | Hattori et al. |
| 7,691,332 B2 | 4/2010 | Kacian et al. |
| 7,762,524 B2 | 7/2010 | Cawthon et al. |
| 7,824,922 B2 | 11/2010 | Kacian et al. |
| 7,963,949 B2 | 6/2011 | Chevallier et al. |
| 8,034,033 B2 | 10/2011 | Grinberg |
| 8,052,944 B2 | 11/2011 | Kacian et al. |
| 8,057,762 B2 | 11/2011 | Kacian et al. |
| 8,158,412 B2 | 4/2012 | Porat et al. |
| 8,234,828 B2 | 8/2012 | MacDonald |
| 8,273,303 B2 | 9/2012 | Ferlic et al. |
| 8,460,620 B2 | 6/2013 | Bartfeld et al. |
| 8,512,308 B2 | 8/2013 | Yokoyama |
| 8,551,067 B2 | 10/2013 | Zinger et al. |
| 8,561,282 B2 | 10/2013 | Hirota |
| D694,405 S | 11/2013 | Khalaj |
| 8,685,347 B2 | 4/2014 | Kacian et al. |
| 8,806,920 B2 | 8/2014 | Blekher et al. |
| 8,827,075 B2 | 9/2014 | Seiwell |
| RE45,194 E | 10/2014 | Kacian et al. |
| 2007/0123831 A1 | 5/2007 | Haindl et al. |
| 2008/0221547 A1 | 9/2008 | Monty |
| 2009/0294446 A1 * | 12/2009 | DeJulio ................ B65D 25/16 220/254.8 |
| 2011/0130740 A1 | 6/2011 | Levy |
| 2013/0060162 A1 * | 3/2013 | Crawford ............ A61J 1/2096 600/576 |

FOREIGN PATENT DOCUMENTS

| | | |
|---|---|---|
| WO | 2007141255 A1 | 12/2007 |
| WO | 2012170813 A1 | 12/2012 |
| WO | 2013148881 A1 | 10/2013 |

OTHER PUBLICATIONS

Aug. 1, 2017 Supplementary European Search Report for EP14874425.

\* cited by examiner

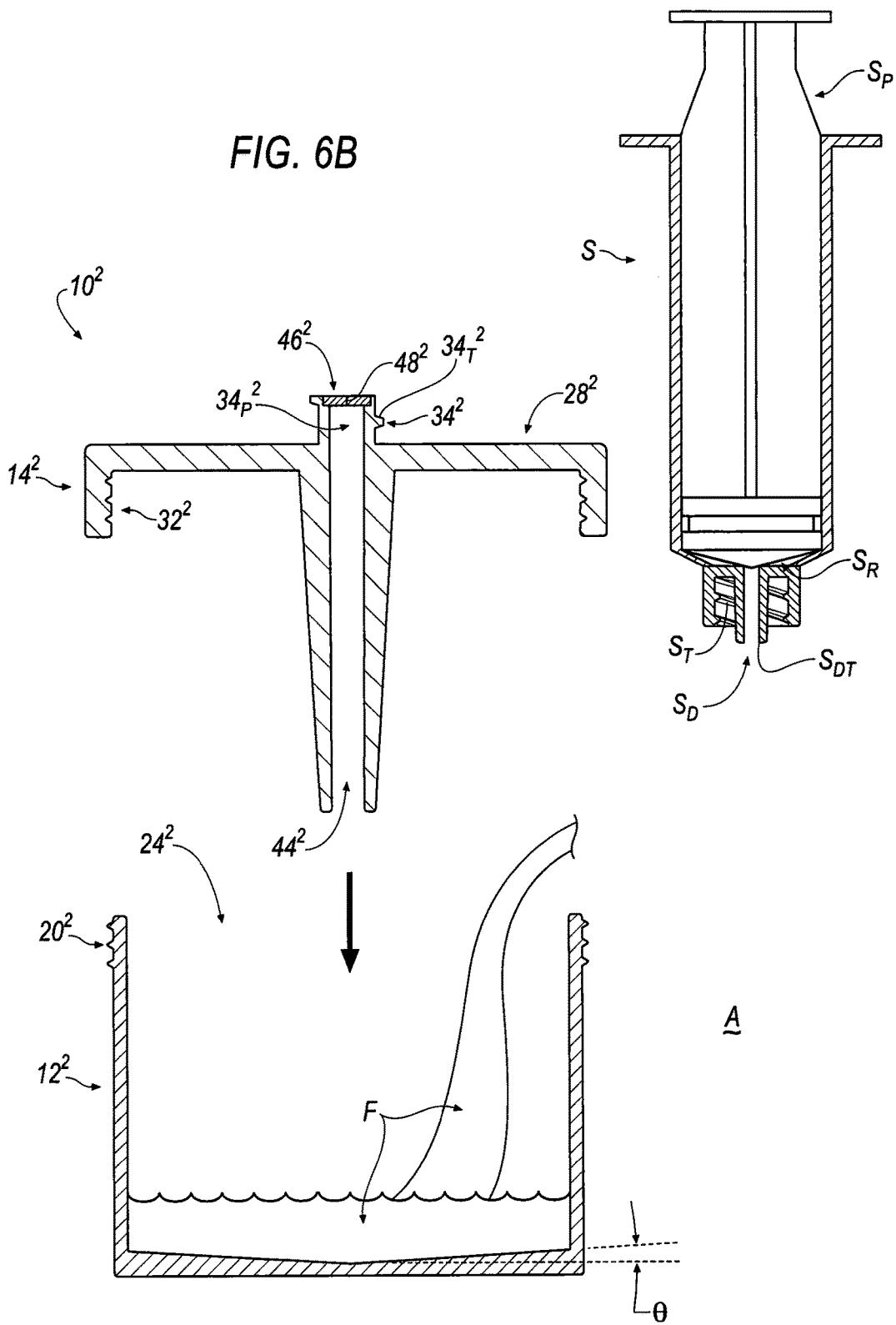

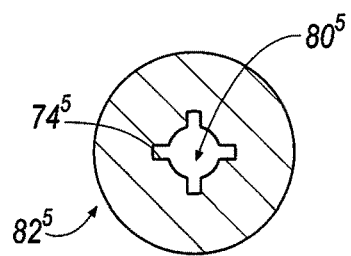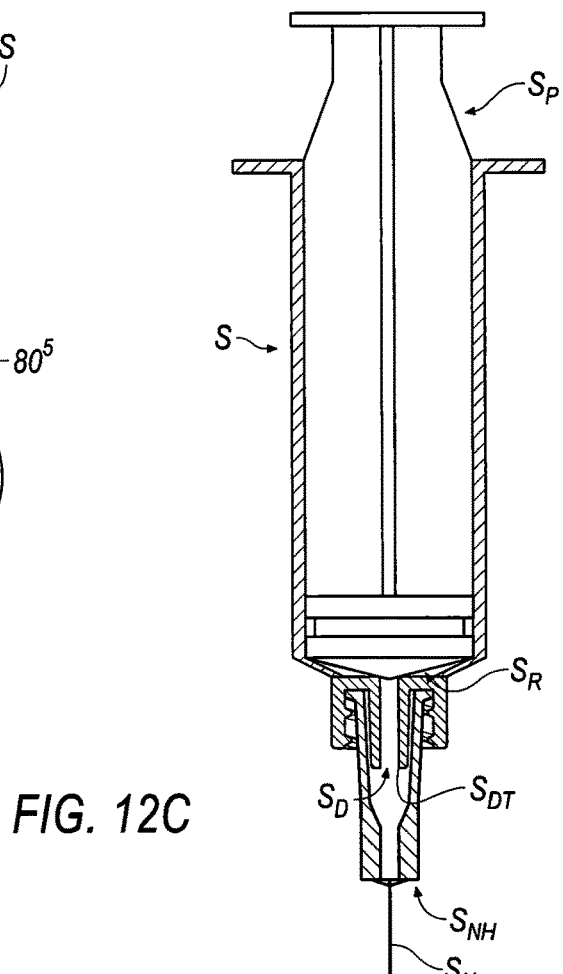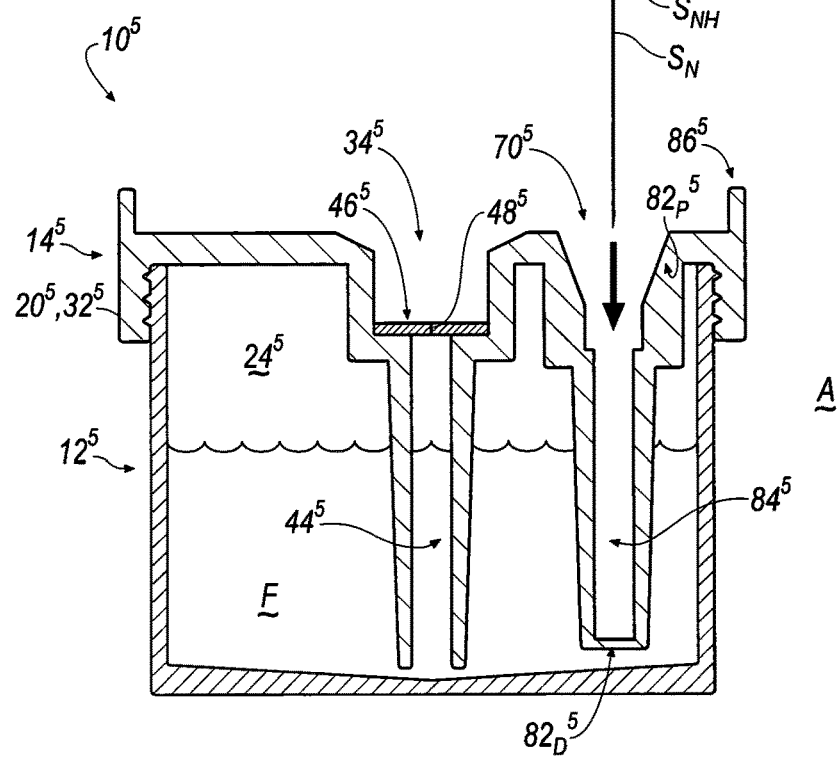
FIG. 13
FIG. 14
FIG. 12C

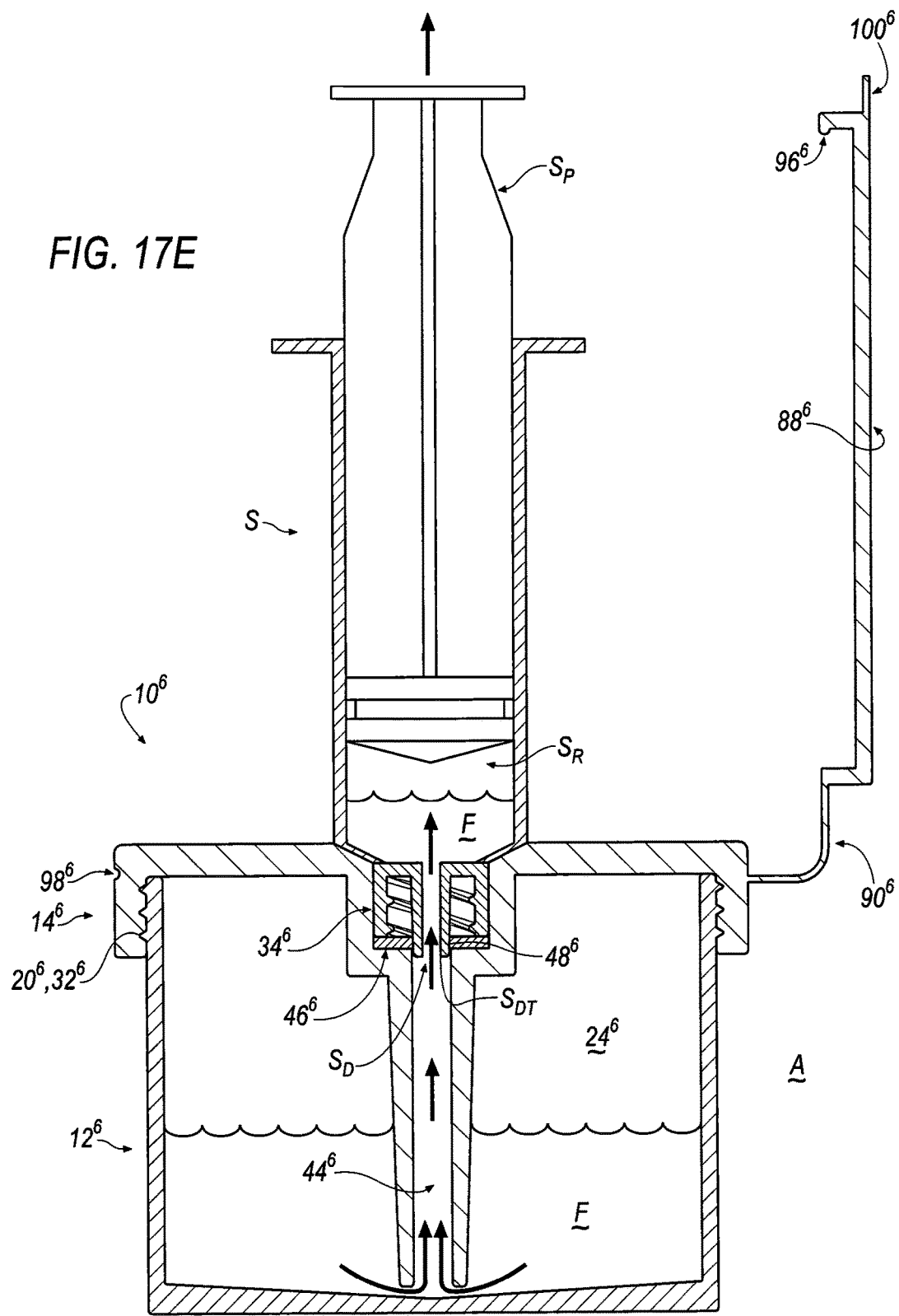

CONTAINER CLOSURE, CONTAINER ASSEMBLY AND METHOD FOR UTILIZING THE SAME

CROSS-REFERENCE TO RELATED APPLICATIONS

This Patent Application is a 35 U.S.C. § 371 United States National Phase Stage of, and claims priority to PCT International Application No. PCT/US2014/071550 filed Dec. 19, 2014, which claims the benefit under 35 U.S.C. § 119 of U.S. Provisional Application 61/964,205, filed on Dec. 27, 2013. The entire contents of both of the aforesaid applications are incorporated by reference herein in their entireties.

FIELD OF THE INVENTION

The disclosure relates to a container closure, a container assembly and a method for utilizing the same.

DESCRIPTION OF THE RELATED ART

Container closures and container assemblies are known in the art. Improvements to container closures and container assemblies are sought in order to advance the art.

BRIEF DESCRIPTION OF THE DRAWINGS

The disclosure will now be described, by way of example, with reference to the accompanying drawings, in which:

FIGS. 6B-6E illustrate a method of utilizing the container assembly of FIG. 6A.

FIGS. 12B-12I illustrate a method of utilizing the container assembly of FIG. 12A.

FIG. 13 is a cross-sectional view according to line 13-13 of FIG. 12B.

FIG. 14 is a cross-sectional view according to line 14-14 of FIG. 12B.

FIGS. 17B-17g illustrate a method of utilizing the container assembly of FIG. 17A.

SUMMARY

Figure 1:
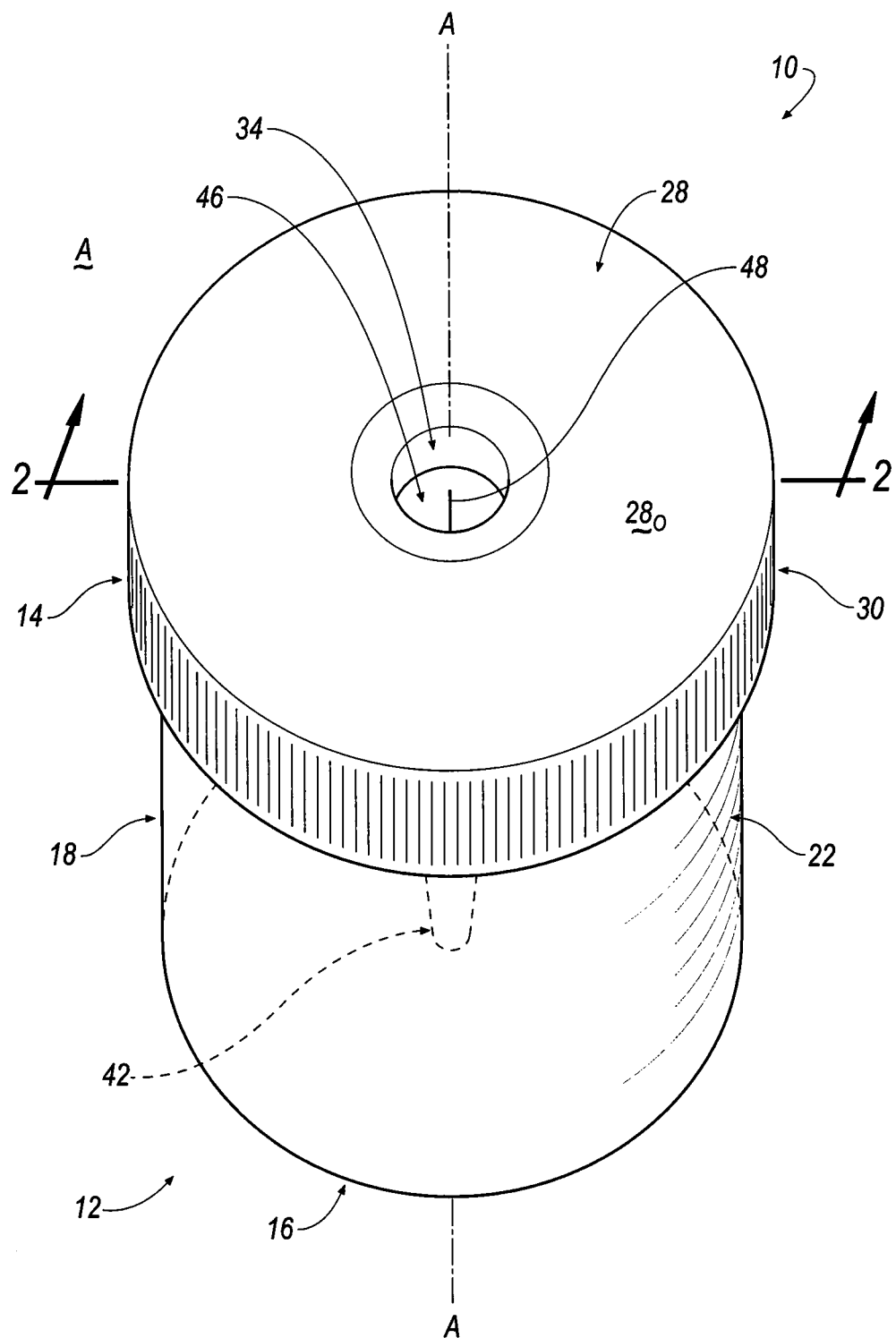
FIG. 1 illustrates a perspective view of a container assembly in accordance with an exemplary embodiment of the invention.

One aspect of the disclosure provides a portion of a container assembly including a container closure. The container closure includes an end wall connected to the side wall. The end wall includes a central portion and an outer perimeter portion. The side wall includes a proximal end and a distal end. The proximal end of the side wall is connected to and extends away from the outer perimeter portion of the end wall. The end wall includes an inner surface and an outer surface. The side wall includes an inner surface and an outer surface. The outer surface of the end wall of the container closure generally defines a syringe-engaging portion. The container closure includes a fluid-drawing member that extends axially away from and is integral with the inner surface of the end wall of the container closure. The fluid-drawing member includes a proximal end and a distal end. A fluid-flow passage extends through the fluid-drawing member between the proximal end and the distal end. The proximal end of the fluid-drawing member is connected to and extends away from the inner surface of the end wall of the container closure.

In some implementations, the syringe-engaging portion is a syringe-receiving bore. The syringe-receiving bore is sized for receiving a distal end of a syringe.

In some examples, the syringe-receiving bore is formed in the outer surface of the end wall. The syringe-receiving bore is aligned with a central axis extending through the container closure.

In some instances, the syringe-receiving bore is formed in the outer surface of the side wall. The syringe-receiving bore is arranged substantially perpendicularly with respect to a central axis extending through the container closure.

In some implementations, the fluid-drawing member includes a radial segment and an axial segment. The radial segment is integral with and extends in a radial direction toward the central axis from the inner surface of the side wall of the container closure. The radial segment is connected to the axial segment that is aligned with the central axis.

In some examples, the syringe-engaging portion is a substantially cylindrical tube-shaped member extending away from the outer surface of the end wall of the container closure. The substantially cylindrical tube-shaped member includes an outer threaded surface that is sized for receiving an inner threaded surface portion of a syringe.

In some instances, the substantially cylindrical tube-shaped member is recessed within a bore formed in the outer surface of the end wall of the container closure.

In some implementations, the substantially cylindrical tube-shaped member is aligned with a central axis extending through the container closure.

In some examples, at least a portion of the fluid-flow passage is aligned with an axial center of the fluid-drawing member.

In some instances, the container closure also includes a disk-shaped member including a slit. The disk-shaped member is disposed upon and supported by one or more of a shoulder surface and an axial wall surface defining the syringe-engaging portion.

In some implementations, the disk-shaped member is secured to one or more of the shoulder surface and the axial wall surface by an adhesive connection.

In some examples, the disk-shaped member is secured to one or more of the shoulder surface and the axial wall surface by a friction-fit connection.

In some instances, the disk-shaped member includes a foam or rubber material.

In some implementations, the container closure also includes a pair of spaced-apart cover-retaining members extending from the outer surface of the end wall of the container closure. The pair of spaced-apart cover-retaining members includes a first cover-retaining member and a second cover-retaining member. The container closure also includes a cover member that is selectively disposed upon and supported by outer surface of the end wall of the container closure. The cover member is selectively retained to the container closure by the pair of spaced-apart cover-retaining members.

In some examples, the cover member isolates the syringe-engaging portion from surrounding atmosphere when the cover member that is selectively disposed upon and supported by outer surface of the end wall of the container closure.

In some instances, each cover-retaining member of the pair of cover-retaining members includes an axial surface portion and a radial surface portion. The axial surface portion of the first cover-retaining member is spaced apart from the axial surface portion of the second cover-retaining member to define a width gap having a width dimension. The radial surface portion of each of the first cover-retaining member and the second cover-retaining member is spaced apart from the outer surface of the end wall of the container closure to define a height gap having a height dimension. The cover member includes a width dimension extending between opposite side surfaces of the cover member. The cover member also includes a height dimension extending between a lower surface and an upper surface of the cover member. The width dimension of the cover member is approximately equal to but slightly less than the width dimension of the gap extending between the axial surface portions of the first cover-retaining member and the second cover-retaining member. The height dimension of the cover member is approximately equal to but slightly less than the height dimension of the gap extending between the radial surface portion of each of the first cover-retaining member and the second cover-retaining member and the outer surface of the end wall of the container closure.

In some implementations, the container closure also includes a needle sheath member that extends axially away from and is integral with the inner surface of the end wall of the container closure. The needle sheath member forms a needle-receiving passage that is sized for receiving a needle extending from a needle hub that is removably-attached to a syringe. The needle-receiving passage is in fluid communication with a needle hub-engaging portion that is defined by the outer surface of the end wall of the container closure. The needle hub-engaging portion is sized for receiving the needle hub that is removably-attached to a syringe.

In some examples, the syringe-engaging portion is aligned with a central axis extending through an axial center the container closure. The needle hub-engaging portion and the needle-receiving passage are radially-offset with respect to the central axis extending through an axial center the container closure.

In some instances, the needle hub-engaging portion is a needle hub-receiving bore.

In some implementations, one or more surface portions of the needle hub-receiving bore are sized for receiving a flanged portion of the needle hub.

In some examples, the container closure also includes a flange wall that extends axially away from and is integral with the outer surface of the end wall of the container closure.

In some instances, the container closure also includes a cover member attached to the container closure by a tether. The cover member includes an end wall having an inner surface and an outer surface. The cover member includes a side wall having an inner surface and an outer surface. The tether includes a proximal end and a distal end. The proximal end of the tether integrally extends radially away from the outer surface of the side wall of the container closure. The distal end of the tether integrally extends from the outer surface of the side wall of the cover member.

In some implementations, the cover member defines a first portion of a snap-fit connection including a projection. The projection extends radially inwardly from the inner surface of the side wall of the cover member. The container closure defines a second portion of the snap-fit connection including a recess. The recess is formed in the outer surface of the side wall of the container closure and opposite where the proximal end of the tether integrally extends radially away from the outer surface of the side wall of the container closure.

In some examples, the cover member includes a flanged lip that extends radially outwardly from the outer surface of the side wall of the cover member. The flanged lip is radially aligned with the snap-fit connection defined by the projection and the recess.

Another aspect of the disclosure provides a container assembly including a container closure connected to a container. The container includes an end wall and a side wall. The end wall of the container includes a central portion and an outer perimeter portion. The side wall of the container includes a proximal end and a distal end. The proximal end of the side wall of the container is connected to and extends away from the outer perimeter portion of the end wall of the container. An inner surface of the end wall of the container and an inner surface of the side wall of the container forms a fluid reservoir. Access to the fluid reservoir is permitted by an opening formed by a distal end of the side wall of the container. The fluid-drawing member extends through the opening and into the fluid reservoir. A distal end of the fluid-drawing member is arranged proximate the inner surface of the end wall of the container. The disk-shaped member prevents fluid communication between surrounding atmosphere and the fluid-flow passage that is in fluid communication with the fluid reservoir.

In some implementations, the inner surface of the side wall of the container closure is connected to an outer surface of the side wall of the container.

In some examples, the inner surface of the side wall of the container closure defines an inner threaded surface. The outer surface of the side wall of the container defines an outer threaded surface. The inner threaded surface is connected to the outer threaded surface.

In some instances, the inner surface of the side wall of the container closure defines one of a projection and a recess. The outer surface of the side wall of the container defines the other of the projection and the recess. The projection is disposed in the recess.

In some implementations, an outer surface of the side wall of the container includes printed indicia.

In some examples, the inner surface inner surface of the end wall of the container is conically-pitched according to an angle toward the central portion of the end wall of the container. The central portion of the end wall of the container is aligned with a central axis extending through an axial center of the container assembly.

In yet another aspect of the disclosure provides a method for utilizing the container assembly including the steps of: disposing a fluid within the fluid reservoir of the container; from surrounding atmosphere, interfacing a syringe with the container closure by: axially-aligning the syringe with the syringe-engaging portion of the container closure, connecting a distal end of the syringe to the syringe-engaging portion of the container closure, and utilizing a distal tip of the syringe for penetrating the disk-shaped member to permit fluid communication between a fluid reservoir of the and the fluid-flow passage that is in fluid communication with the fluid reservoir that contains the fluid; and actuating the syringe for withdrawing an amount of the fluid from the fluid reservoir.

In some implementations, the syringe-engaging portion is a syringe-receiving bore. The connecting step includes: inserting the distal end of the syringe into the syringe-receiving bore.

In some examples, the syringe-engaging portion is a substantially cylindrical tube-shaped member extending away from the outer surface of the end wall of the container closure. The substantially cylindrical tube-shaped member includes an outer threaded surface that is sized for receiving an inner threaded surface portion of a syringe. The connecting step includes: rotating the syringe relative the substantially cylindrical tube-shaped member for threadingly connecting the inner threaded surface portion of a syringe to the outer threaded surface of the substantially cylindrical tube-shaped member.

In some instances, prior to the interfacing step, the method further includes the step of: removing a cover member from the outer surface of the end wall of the container closure for permitting access to the syringe-engaging portion.

In some implementations, prior to the interfacing step, the method further includes the steps of: axially-aligning the syringe that is attached to a needle hub that is attached to a needle with a needle sheath member defining a needle-receiving passage and a needle hub-receiving bore; inserting the needle into the needle-receiving passage and arranging the needle hub within the needle hub-receiving bore; and disconnecting the needle hub from the distal end of the syringe and docking the needle in needle sheath member.

In some examples, after the actuating step, the method further includes the steps of: axially-aligning the distal end of the syringe with the needle hub-receiving bore; attaching the distal end of the syringe to the needle hub; and withdrawing the needle from the needle-receiving passage and the needle hub from the needle hub-receiving bore.

DETAILED DESCRIPTION OF THE INVENTION

The Figures illustrate exemplary embodiments of container closures, container assemblies and methods for utilizing the same. Based on the foregoing, it is to be generally understood that the nomenclature used herein is simply for convenience and the terms used to describe the invention should be given the broadest meaning by one of ordinary skill in the art.

An exemplary container assembly is shown generally at 10 in FIG. 1. The container assembly 10 generally includes a container 12 and a container closure 14.

Figure 2A:
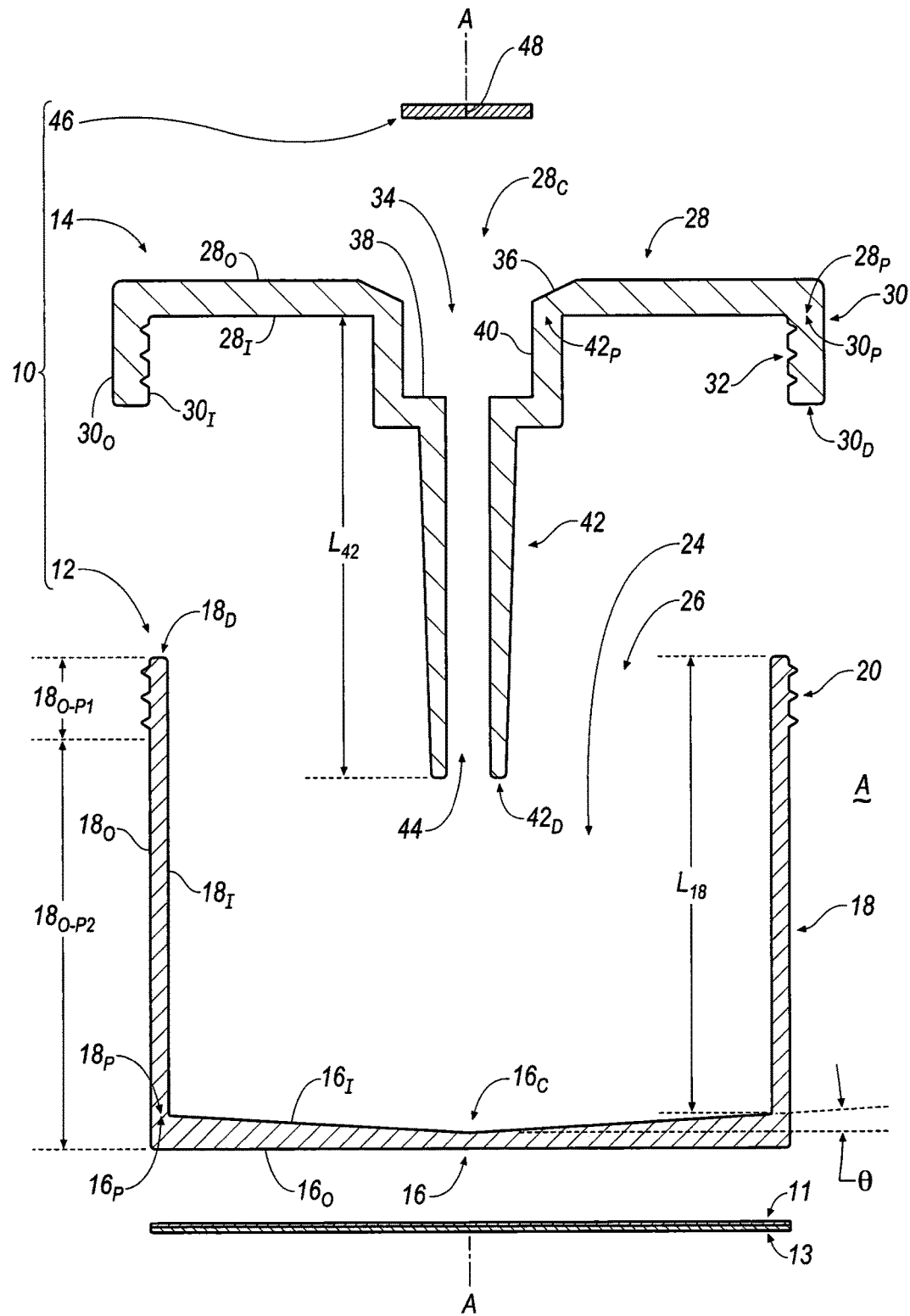
FIG. 2A is an exploded cross-sectional view of the container assembly according to line 2-2 of FIG. 1.

Referring to FIG. 2A, the container 12 includes an end wall 16 and a side wall 18. The end wall 16 and the side wall 18 may include any desirable material or geometry. In some instances, the container 12 may include a clear plastic or glass material; in some implementations, the material may include a coating (e.g., an antimicrobial coating). In some examples as seen in FIG. 1, the end wall 16 may define an annular member and the side wall 18 may define a cylindrical, tube-shaped body.

As seen in FIG. 2A, the end wall 16 includes a central portion $16_C$ and an outer perimeter portion $16_P$. The side wall 18 includes a proximal end $18_P$ and a distal end $18_D$. The proximal end $18_P$ of the side wall 18 is connected to and extends away from the outer perimeter portion $16_P$ of the end wall 16.

The end wall 16 includes an inner surface $16_I$ and an outer surface $16_O$. The inner surface $16_I$ of the end wall 16 may be conically-pitched according to an angle, θ, to define the central portion $16_C$ of the end wall 16 the container 12 to be a low point of the inner surface $16_I$ of the end wall 16 of the container 12. In some instances, the angle may be approximately equal to 15°. In some examples, the container 12 may optionally include an adhesive 11 applied over the outer surface $16_O$ of the end wall 16. In some instances, an optional release paper 13 may be applied over the adhesive 11. Prior to disposing the container 12 upon a support surface, a user may remove the release paper (thereby exposing the adhesive 11 applied over the outer surface $16_O$ of the end wall 16); the exposed adhesive 13 may assist in the prevention of movement of the container 12 upon the support surface once the outer surface $16_O$ of the end wall 16 is arranged upon the support surface.

The side wall 18 includes an inner surface $18_I$ and an outer surface $18_O$. A first portion $18_{O-P1}$ of the outer surface $18_O$ of the side wall 18 may define an outer threaded surface 20 of the container 12. A second portion $18_{O-P2}$ of the outer surface $18_O$ of the side wall 18 may include printed indicia 22 (as seen in FIG. 1) defining, for example, an amount of fluid disposed within the container 12. As will be described in the following disclosure, the outer threaded surface 20 of the container 12 may cooperate with an inner threaded surface 32 of the container closure 14 for selectively attaching the container closure 14 to the container 12.

The container 12 forms a fluid reservoir 24 that is defined by the inner surface $16_I$, $18_I$ of both of the end wall 16 and the side wall 18. Access to the fluid reservoir 24 is permitted by an opening 26 formed by the distal end $18_D$ of the side wall 18.

Referring to FIG. 2A, the container closure 14 includes an end wall 28 and a side wall 30. The end wall 28 and the side wall 30 may include any desirable material or geometry. In some instances, the container closure 14 may include an opaque plastic material; in some implementations, the material may include a coating (e.g., an antimicrobial coating). In some examples as seen in FIG. 1, the end wall 28 may define an annular member and the side wall 30 may define a cylindrical, tube-shaped body.

As seen in FIG. 2A, the end wall 28 includes a central portion $28_C$ and an outer perimeter portion $28_P$. The side wall 30 includes a proximal end $30_P$ and a distal end $30_D$. The proximal end $30_P$ of the side wall 30 is connected to and extends away from the outer perimeter portion $28_P$ of the end wall 28. The central portion $28_C$ of the end wall 28 of the container closure 14 and the central portion $16_C$ of the end wall 16 of the container 12 may be aligned with a central axis, A-A, extending through the container assembly 10.

The end wall 28 includes an inner surface $28_I$ and an outer surface $28_O$. The side wall 30 includes an inner surface $30_I$ and an outer surface $30_O$. The inner surface $30_I$ of the side wall 30 may define an inner threaded surface 32 of the container closure 14. As will be described in the following disclosure, the inner threaded surface 32 of the container closure 14 may cooperate with the outer threaded surface 20 of the container 12 for selectively attaching the container closure 14 to the container 12.

The outer surface $28_O$ of the end wall 28 of the container closure 14 generally defines a syringe-engaging portion, such as, for example, a syringe-receiving bore 34. The syringe-receiving bore 34 is formed in the central portion $28_C$ of the end wall 28 of the container closure 14. An axial center of the syringe-receiving bore 34 is aligned with the central axis, A-A.

The syringe-receiving bore 34 is defined by portions 36, 38, 40 of the outer surface $28_O$ of the end wall 28 of the container closure 14 and sized for receiving a distal end, $S_D$ (see, e.g., FIGS. 2B-2E), of a syringe, S (see, e.g., FIGS. 2B-2E). The portions 36, 38, 40 of the outer surface $28_O$ of the end wall 28 of the container closure 14 includes: a first shoulder surface 36, a second shoulder surface 38 and an axial wall surface 40 extending substantially perpendicularly from the second shoulder surface 38 and connects the first shoulder surface 36 to the second shoulder surface 38. The first shoulder surface 36 may be tapered in order to conform to a tapered outer wall surface portion of the distal end, $S_D$, of the syringe, S.

The container closure 14 also includes a fluid-drawing member 42 that extends axially away from and is integral with the inner surface $28_I$ of the end wall 28 of the container closure 14. The fluid-drawing member 42 includes a proximal end $42_P$ and a distal end $42_D$. A fluid-flow passage 44 extends through the fluid-drawing member 42 between the proximal end $42_P$ and the distal end $42_D$. The fluid-flow passage 44 is aligned with an axial center of the fluid-drawing member 42. When the container closure 14 is connected to the container 12, the fluid-flow passage 44 is in fluid communication with the fluid reservoir 24 defined by the container 12.

The proximal end $42_P$ of the fluid-drawing member 42 is connected to and extends away from the inner surface $28_I$ of the end wall 28 of the container closure 14. In some instances, the fluid-drawing member 42 may extend away from the inner surface $28_I$ at the central portion $28_C$ of the end wall 28 of the container closure 14 (such that the fluid-drawing member 42 is aligned with the central axis, A-A, when the container closure 14 is attached to the container 12).

The fluid-drawing member 42 may also be defined by a length dimension, $L_{42}$. A portion of the syringe-receiving bore 34 may extend into a portion of the length, $L_{42}$, defining the fluid-drawing member 42. The length dimension $L_{42}$ of the fluid-drawing member 42 may be approximately equal to, but slightly greater than a length $L_{18}$ of the side wall 18 of the container 12; due to the conically-pitched angle, θ, formed by the inner surface $16_I$ of the end wall 16, upon connecting the container closure 14 to the container 12, the distal end $42_D$ of the fluid-drawing member 42 may be arranged substantially adjacent to but in a slightly spaced-apart relationship with respect to the inner surface $16_I$ of the end wall 16 defined by the central portion $16_C$ of the end wall 16 that is aligned with the central axis, A-A. By selectively defining the length relationship of the length dimensions $L_{42}$, $L_{18}$ of the fluid-drawing member 42 and the side wall 18, and, in addition, the axial alignment of the fluid-drawing member 42 with respect to the central portion $28_C$ of the end wall 28 of the container closure 14, the fluid drawing member 42 is selectively positioned relative to the container 12 in order to draw a remainder of fluid, F, contained within the fluid reservoir 24 when all of the fluid, F, contained within the container 12 is nearly depleted as seen in FIG. 2E.

The container assembly 10 also includes a disk-shaped member 46 that is disposed upon and supported by one or both of the second shoulder surface 38 and the axial wall surface 40 defining the syringe-receiving bore 34. The disk-shaped member 46 may be secured to one or more of the second shoulder surface 38 and the axial wall surface 40 in any desirable fashion (e.g., with an adhesive or a friction-fit connection). The disk-shaped member 46 may be formed from any desirable material including, for example, foam, rubber or the like.

The disk-shaped member 46 selectively prevents fluid communication between the syringe-receiving bore 34 and the fluid-flow passage 44. The disk-shaped member 46 also inhibits contaminates from surrounding atmosphere, A, from entering the fluid-flow passage 44 and into the fluid reservoir 24.

The disk-shaped member 46 may include a slit 48 that is aligned with an axial center of both of the container closure 14 and the disk-shaped member 46. The slit 48 permits selective fluid communication with the fluid-flow passage 44 and the fluid reservoir 24 from surrounding atmosphere, A. Access to (i.e., fluid communication) with the fluid-flow passage 44 from a device (e.g., the syringe, S) that is located in surrounding atmosphere, A, is permitted when a distal tip, $S_{DT}$, of the syringe, S, axially penetrates the slit 48 as seen in FIG. 2D.

Figure 2B:
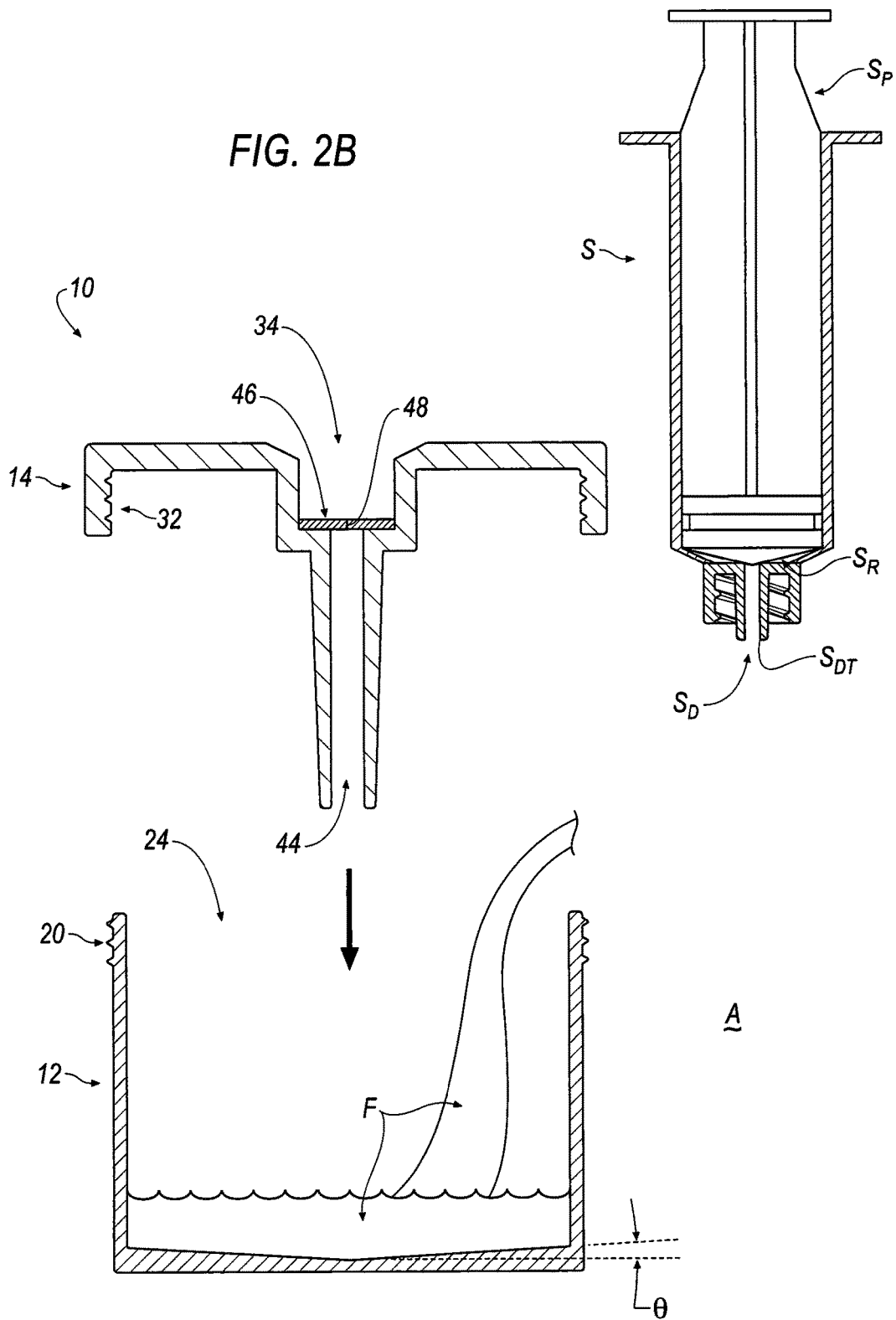
FIGS. 2B-2E illustrate a method of utilizing the container assembly of FIG. 2A.
Figure 2C:
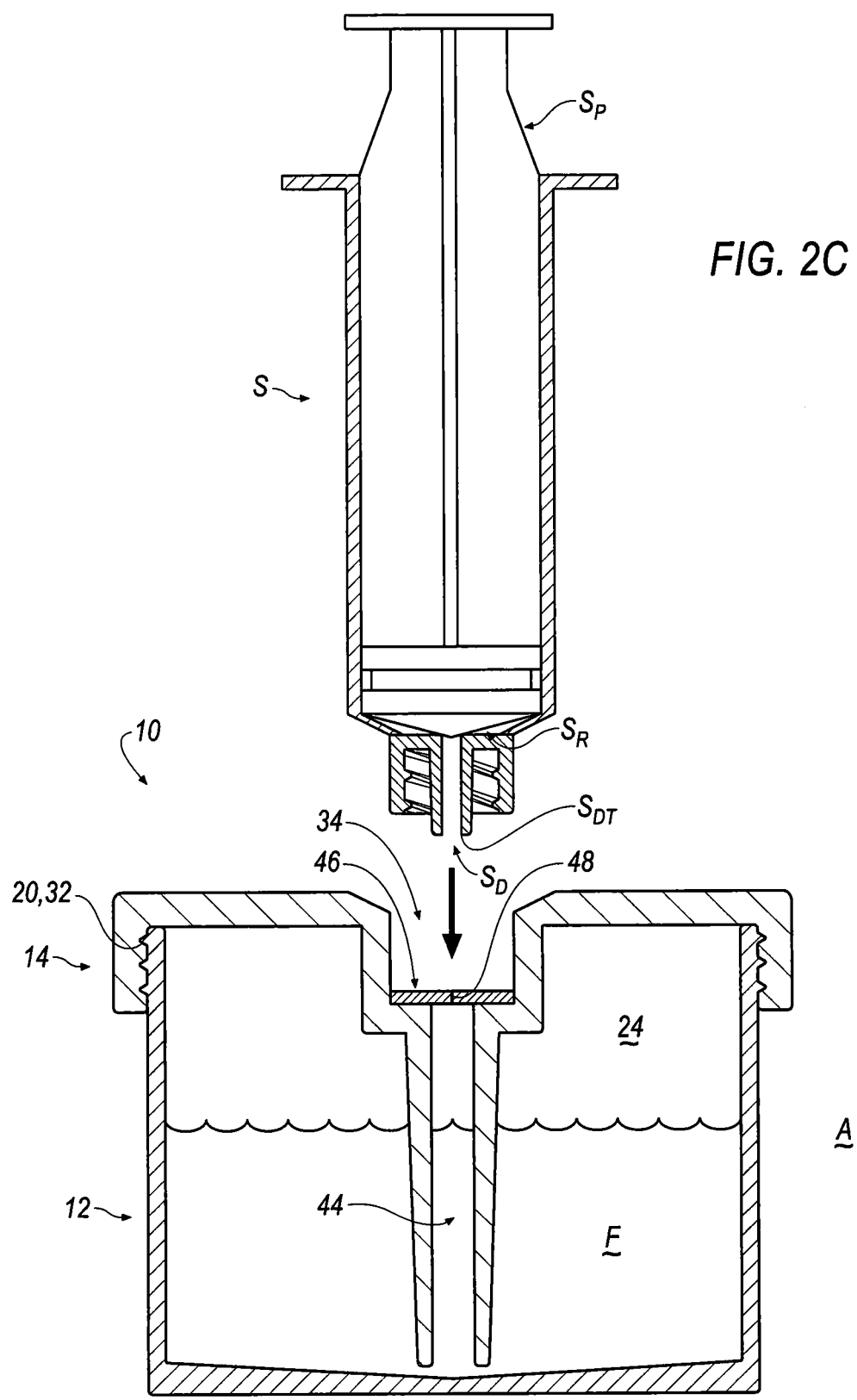
Figure 2D:
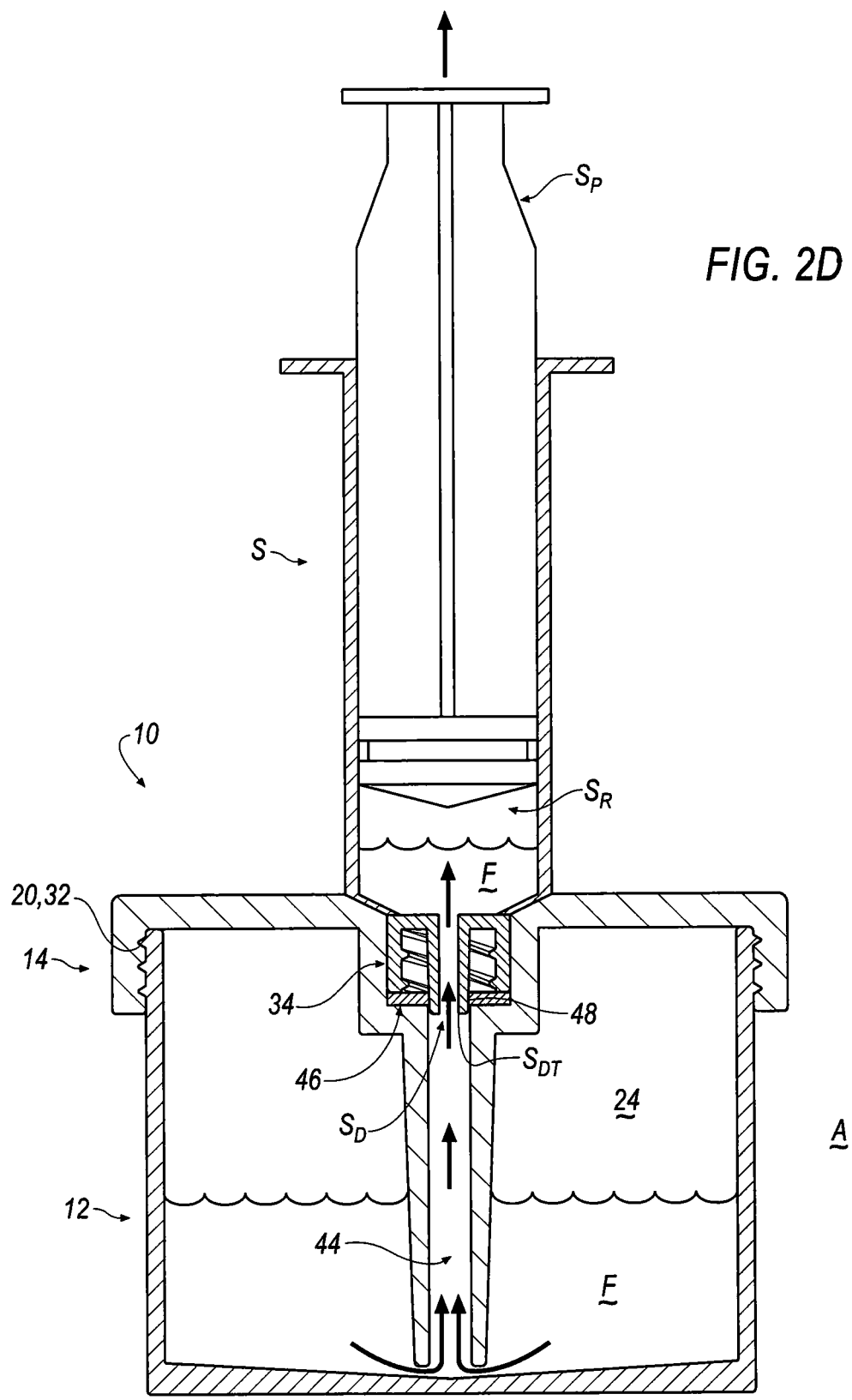
Figure 2E:
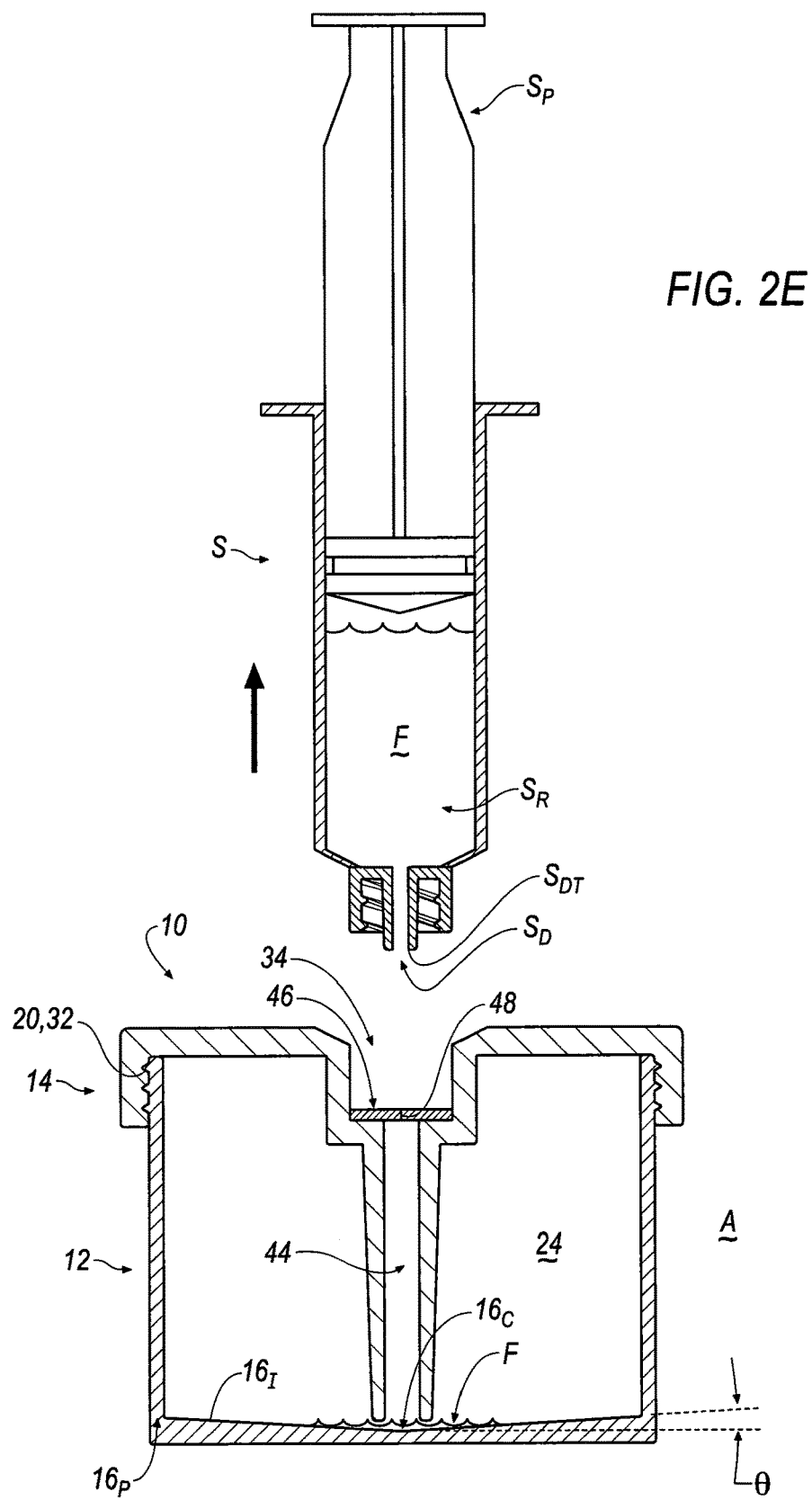

Referring to FIGS. 2B-2E, a method for utilizing the container assembly 10 is described. Referring firstly to FIG. 2B, the container closure 14 is shown disengaged from the container 12, and, a fluid, F, is disposed within the fluid reservoir 24. Referring to FIG. 2C, the container closure 14 is connected (e.g., threadingly-connected) to the container 12 by, for example, the cooperating threaded surfaces 20, 32 of the container 12 and container closure 14 thereby fluidly sealing the fluid reservoir 24 from surrounding atmosphere, A. Once the container closure 14 is secured to the container 12, the distal end, $S_D$, of the syringe, S, may be axially-aligned with and arranged over the syringe-receiving bore 34 formed in the central portion $28_C$ of the end wall 28 of the container closure 14.

Referring to FIG. 2D, the distal end, $S_D$, of the syringe, S, is inserted into the syringe-receiving bore 34 and the distal tip, $S_{DT}$, of the syringe, S, axially penetrates the slit 48 to thereby arrange a fluid reservoir, $S_R$, of the syringe, S, in fluid communication with the fluid-flow passage 44 that is in fluid communication with the fluid, F, contained by the fluid reservoir 24. Once the fluid reservoir, $S_R$, of the syringe, S, is in fluid communication with the fluid-flow passage 44 as described above, a user may axially manipulate a plunger, $S_P$, of the syringe, S, in order to draw the fluid, F, from the fluid reservoir 24 into the fluid reservoir, $S_R$, of the syringe, S, by way of the fluid-flow passage 44.

Referring to FIG. 2E, once the user has withdrawn a desired amount of fluid, F, from the fluid reservoir 24 and into the fluid reservoir, $S_R$, of the syringe, S, the user may remove the distal end, $S_D$, of the syringe, S, from the syringe-receiving bore 34. Once the distal end, $S_D$, of the syringe, S, is withdrawn from the syringe-receiving bore 34, the distal tip, $S_{DT}$, of the syringe, S, no longer penetrates the slit 48, and, as a result, the disk-shaped member 46 may return to its pre-penetrated state, thereby fluidly sealing the fluid-flow passage 44 and the fluid reservoir 24 from surrounding atmosphere, A.

As seen in FIG. 2E, the conically-pitched angle, θ, formed by the inner surface $16_I$ of the end wall 16, directs a remainder of non-withdrawn fluid, F, disposed upon the inner surface $16_I$ of the end wall 16 (with the assistance of gravity) away from the outer perimeter portion $16_P$ of the end wall 16 and toward the central portion $16_C$ of the end wall 16; as a result, the remainder of the non-withdrawn fluid, F, may be arranged/aligned with the fluid-flow passage 44 for subsequent withdrawal from the container 12.

Figure 3:
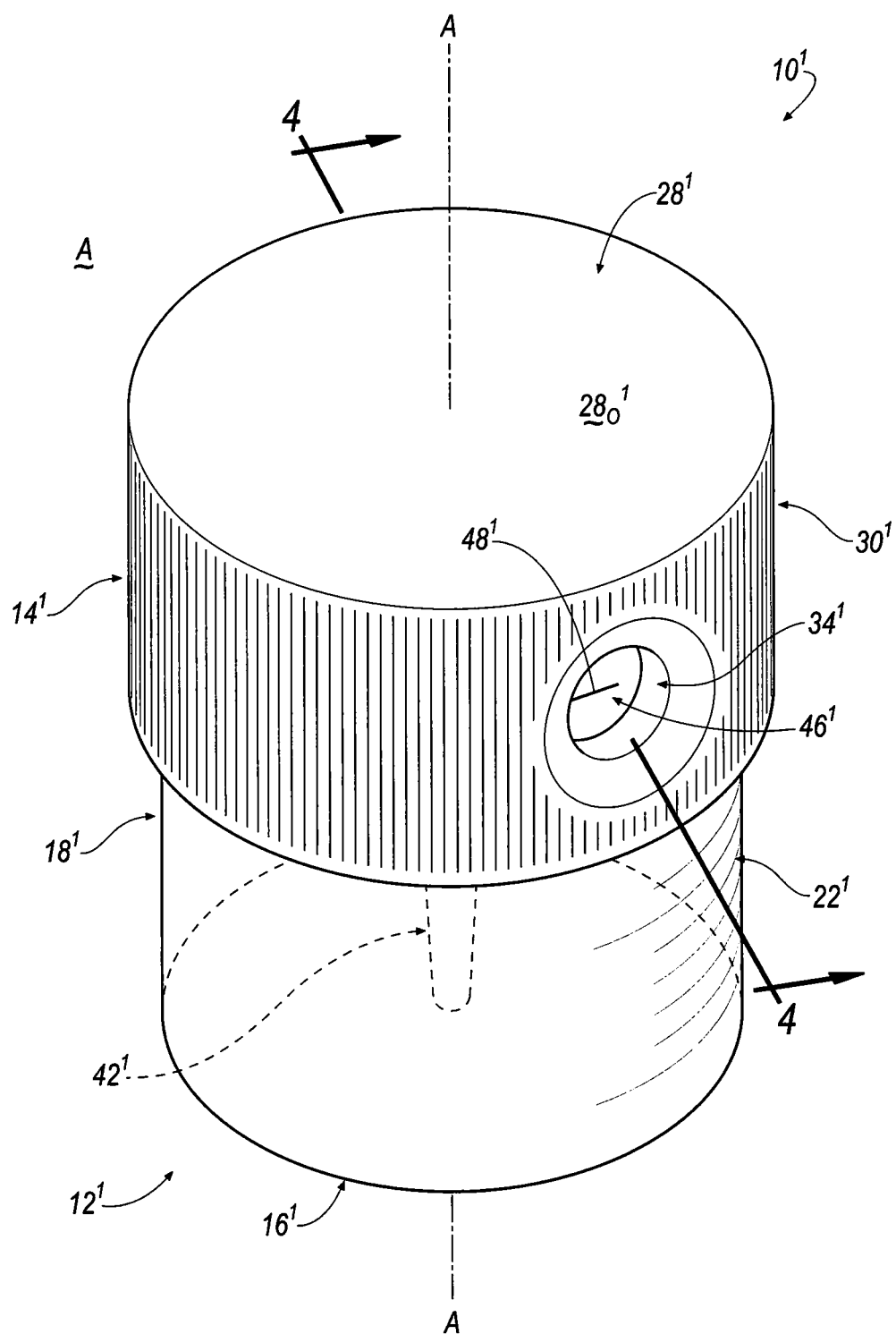
FIG. 3 illustrates a perspective view of a container assembly in accordance with an exemplary embodiment of the invention.

An exemplary container assembly is shown generally at $10^1$ in FIG. 3. The container assembly $10^1$ generally includes a container $12^1$ and a container closure $14^1$.

Figure 4A:
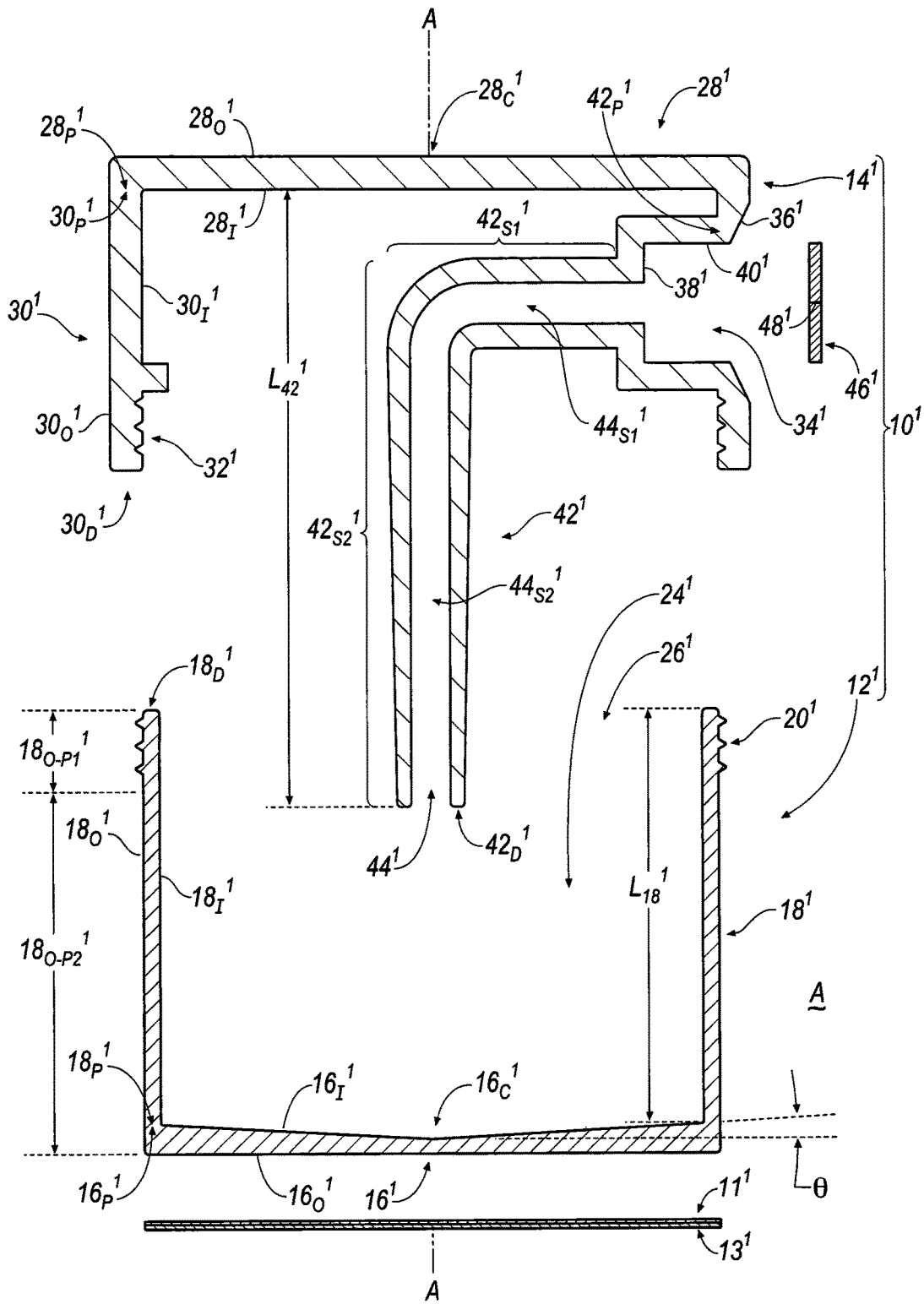
FIG. 4A is an exploded cross-sectional view of the container assembly according to line 4-4 of FIG. 3.

Referring to FIG. 4A, the container $12^1$ includes an end wall $16^1$ and a side wall $18^1$. The end wall $16^1$ and the side wall $18^1$ may include any desirable material or geometry. In some instances, the container $12^1$ may include a clear plastic or glass material; in some implementations, the material may include a coating (e.g., an antimicrobial coating). In some examples as seen in FIG. 3, the end wall $16^1$ may define an annular member and the side wall $18^1$ may define a cylindrical, tube-shaped body.

As seen in FIG. 4A, the end wall $16^1$ includes a central portion $16_C^1$ and an outer perimeter portion $16_P^1$. The side wall $18^1$ includes a proximal end $18_P^1$ and a distal end $18_D^1$. The proximal end $18_P^1$ of the side wall $18^1$ is connected to and extends away from the outer perimeter portion $16_P^1$ of the end wall $16^1$.

The end wall $16^1$ includes an inner surface $16_I^1$ and an outer surface $16_O^1$. The inner surface $16_I^1$ of the end wall $16^1$ may be conically-pitched according to an angle, θ, to define the central portion $16_C^1$ of the end wall $16^1$ the container $12^1$ to be a low point of the inner surface $16_I^1$ of the end wall $16^1$ of the container $12^1$. In some instances, the angle may be approximately equal to 15°. In some examples, the container $12^1$ may optionally include an adhesive $11^1$ applied over the outer surface $16_O^1$ of the end wall $16^1$. In some instances, an optional release paper $13^1$ may be applied over the adhesive $11^1$. Prior to disposing the container $12^1$ upon a support surface, a user may remove the release paper (thereby exposing the adhesive $11^1$ applied over the outer surface $16_O^1$ of the end wall $16^1$); the exposed adhesive $13^1$ may assist in the prevention of movement of the container $12^1$ upon the support surface once the outer surface $16_O^1$ of the end wall $16^1$ is arranged upon the support surface.

The side wall $18^1$ includes an inner surface $18_I^1$ and an outer surface $18_O^1$. A first portion $18_{O-P1}^1$ of the outer surface $18_O^1$ of the side wall $18^1$ may define an outer threaded surface $20^1$ of the container $12^1$. A second portion $18_{O-P2}^1$ of the outer surface $18_O^1$ of the side wall $18^1$ may include printed indicia $22^1$ (as seen in FIG. 3) defining, for example, an amount of fluid disposed within the container $12^1$. As will be described in the following disclosure, the outer threaded surface $20^1$ of the container $12^1$ may cooperate with an inner threaded surface $32^1$ of the container closure $14^1$ for selectively attaching the container closure $14^1$ to the container $12^1$.

The container $12^1$ forms a fluid reservoir $24^1$ that is defined by the inner surface $16_I^1$, $18_I^1$ of both of the end wall $16^1$ and the side wall $18^1$. Access to the fluid reservoir $24^1$ is permitted by an opening $26^1$ formed by the distal end $18_D^1$ of the side wall $18^1$.

Referring to FIG. 4A, the container closure $14^1$ includes an end wall $28^1$ and a side wall $30^1$. The end wall $28^1$ and the side wall $30^1$ may include any desirable material or geometry. In some instances, the container closure $14^1$ may include an opaque plastic material; in some implementations, the material may include a coating (e.g., an antimicrobial coating). In some examples as seen in FIG. 3, the end wall $28^1$ may define an annular member and the side wall $30^1$ may define a cylindrical, tube-shaped body.

As seen in FIG. 4A, the end wall $28^1$ includes a central portion $28_C^1$ and an outer perimeter portion $28_P^1$. The side wall $30^1$ includes a proximal end $30_P^1$ and a distal end $30_D^1$. The proximal end $30_P^1$ of the side wall $30^1$ is connected to and extends away from the outer perimeter portion $28_P^1$ of the end wall $28^1$. The central portion $28_C^1$ of the end wall $28^1$ of the container closure $14^1$ and the central portion $16_C^1$ of the end wall $16^1$ of the container $12^1$ may be aligned with a central axis, A-A, extending through the container assembly $10^1$.

The end wall $28^1$ includes an inner surface $28_I^1$ and an outer surface $28_O^1$. The side wall $30^1$ includes an inner surface $30_I^1$ and an outer surface $30_O^1$. A portion of the inner surface $30_I^1$ of the side wall $30^1$ may define an inner threaded surface $32^1$ of the container closure $14^1$. As will be described in the following disclosure, the inner threaded surface $32^1$ of the container closure $14^1$ may cooperate with the outer threaded surface $20^1$ of the container $12^1$ for selectively attaching the container closure $14^1$ to the container $12^1$.

A portion of the outer surface $30_O^1$ of the side wall $30^1$ of the container closure $14^1$ generally defines a syringe-engaging portion, such as, for example, a syringe-receiving bore $34^1$. Unlike the container closure 14 described above at FIGS. 1-2E, the syringe-receiving bore $34^1$ is not axially-aligned with the central axis, A-A; rather, an axial center of the syringe-receiving bore $34^1$ is arranged substantially perpendicularly with respect to the central axis, A-A. Because the syringe-receiving bore $34^1$ is arranged in a radial orientation (as opposed to an axial orientation described above at FIGS. 1-2E), contaminates that may fall with gravity are less likely to infiltrate the syringe-receiving bore $34^1$. Although the syringe-engaging portion is shown as a syringe-receiving bore $34^1$ that is arranged substantially perpendicularly with respect to the central axis, A-A at FIGS. 3-4E, the syringe-engaging portion $34^1$ at FIGS. 3-4E is not limited to a bore and may include other structure configurations such as, for example, a Luer lock (see, e.g., $34^2$, $34^3$ in FIGS. 5-6E and 7-8E, respectively) extending from an outer surface (see, e.g., $28_O^2$ in FIGS. 5-6E) or recessed in a bore (see, e.g., $35^3$ in FIG. 7-8E) that is arranged substantially perpendicularly with respect to the central axis, A-A.

The syringe-receiving bore $34^1$ is defined by portions $36^1$, $38^1$, $40^1$ of the outer surface $30_O^1$ of the side wall $30^1$ of the container closure $14^1$ and sized for receiving a distal end, $S_D$, of a syringe, S. The portions $36^1$, $38^1$, $40^1$ of the outer surface $30_O^1$ of the side wall $30^1$ of the container closure $14^1$ includes: a first shoulder surface $36^1$, a second shoulder surface $38^1$ and an axial wall surface $40^1$ extending substantially perpendicularly from the second shoulder surface $38^1$ and connects the first shoulder surface $36^1$ to the second shoulder surface $38^1$. The first shoulder surface $36^1$ may be tapered in order to conform to a tapered outer wall surface portion of the distal end, $S_D$, of the syringe, S.

The container closure $14^1$ also includes a fluid-drawing member $42^1$ having a radial segment $42_{S1}^1$ and an axial segment $42_{S2}^1$. The radial segment $42_{S1}^1$ is integral with and extends in a radial direction (with respect to the central axis, A-A) away from the inner surface $30_I^1$ of the side wall $30^1$ of the container closure $14^1$. As the radial segment $42_{S1}^1$ extends toward the central axis, A-A, the fluid-drawing member $42^1$ deviates from a radially-extending direction (defined by the radial segment $42_{S1}^1$) to an axially-extending direction (defined by the axial segment $42_{S2}^1$, which is aligned with the central axis, A-A).

The fluid-drawing member $42^1$ includes a proximal end $42_P^1$ and a distal end $42_D^1$. A fluid-flow passage $44^1$ extends through the fluid-drawing member $42^1$ between the proximal end $42_P^1$ and the distal end $42_D^1$. Like the fluid-drawing member $42^1$, the fluid-flow passage $44^1$ includes a radial segment $44_{S1}^1$ and an axial segment $44_{S2}^1$. When the container closure $14^1$ is connected to the container $12^1$, the fluid-flow passage $44^1$ is in fluid communication with the fluid reservoir $24^1$ defined by the container $12^1$. The proximal end $42_P^1$ of the fluid-drawing member $42^1$ is connected to and extends away from the inner surface $30_I^1$ of the side wall $30^1$ of the container closure $14^1$.

The fluid-drawing member $42^1$ may also be defined by a length dimension, $L_{42}^1$, that is referenced from the inner surface $28_I^1$ of the $28^1$. The length dimension, $L_{42}^1$, extends between the inner surface $28_I^1$ of the $28^1$ and the distal end $42_D^1$ of the fluid-drawing member $42^1$.

The syringe-receiving bore $34^1$ may extend into a portion of the fluid-drawing member $42^1$ at the proximal end $42_P^1$ of the fluid-drawing member $42^1$. The length dimension $L_{42}^1$ of the fluid-drawing member $42^1$ may be approximately equal to, but slightly greater than a length $L_{18}^1$ of the side wall $18^1$ of the container $12^1$; due to the conically-pitched angle, θ, formed by the inner surface $16_I^1$ of the end wall $16^1$, upon connecting the container closure $14^1$ to the container $12^1$, the distal end $42_D^1$ of the fluid-drawing member $42^1$ may be arranged substantially adjacent to but in a slightly spaced-apart relationship with respect to the inner surface $16_I^1$ of the end wall $16^1$ defined by the central portion $16_C^1$ of the end wall $16^1$ that is aligned with the central axis, A-A. By selectively defining the length relationship of the length dimensions $L_{42}^1$, $L_{18}^1$ of the fluid-drawing member $42^1$ and the side wall $18^1$, and, in addition, the axial alignment of the fluid-drawing member $42^1$ with respect to the central portion $28_C^1$ of the end wall $28^1$ of the container closure $14^1$, the fluid drawing member $42^1$ is selectively positioned relative to the container $12^1$ in order to draw a remainder of fluid, F, contained within the fluid reservoir $24^1$ when all of the fluid, F, contained within the container $12^1$ is nearly depleted (as seen, e.g., in FIG. 4E).

The container assembly $10^1$ also includes a disk-shaped member $46^1$ that is disposed upon and supported by one or both of the second shoulder surface $38^1$ and the axial wall surface $40^1$ defining the syringe-receiving bore $34^1$. The disk-shaped member $46^1$ may be secured to one or more of the second shoulder surface $38^1$ and the axial wall surface $40^1$ in any desirable fashion (e.g., with an adhesive or a friction-fit connection). The disk-shaped member $46^1$ may be formed from any desirable material including, for example, foam, rubber or the like.

The disk-shaped member $46^1$ selectively prevents fluid communication between the syringe-receiving bore $34^1$ and the fluid-flow passage $44^1$. The disk-shaped member $46^1$ also inhibits contaminates from surrounding atmosphere, A, from entering the fluid-flow passage $44^1$ and into the fluid reservoir $24^1$.

The disk-shaped member $46^1$ may include a slit $48^1$ that is aligned with an axial center of the disk-shaped member $46^1$. The slit $48^1$ permits selective fluid communication with the fluid-flow passage $44^1$ and the fluid reservoir $24^1$ from surrounding atmosphere, A. Access to (i.e., fluid communication) with the fluid-flow passage $44^1$ from a device (e.g., the syringe, S) that is located in surrounding atmosphere, A, is permitted when a distal tip, $S_{DT}$, of the syringe, S, axially penetrates the slit $48^1$ (as seen, e.g., in FIG. 4D).

Figure 4B:
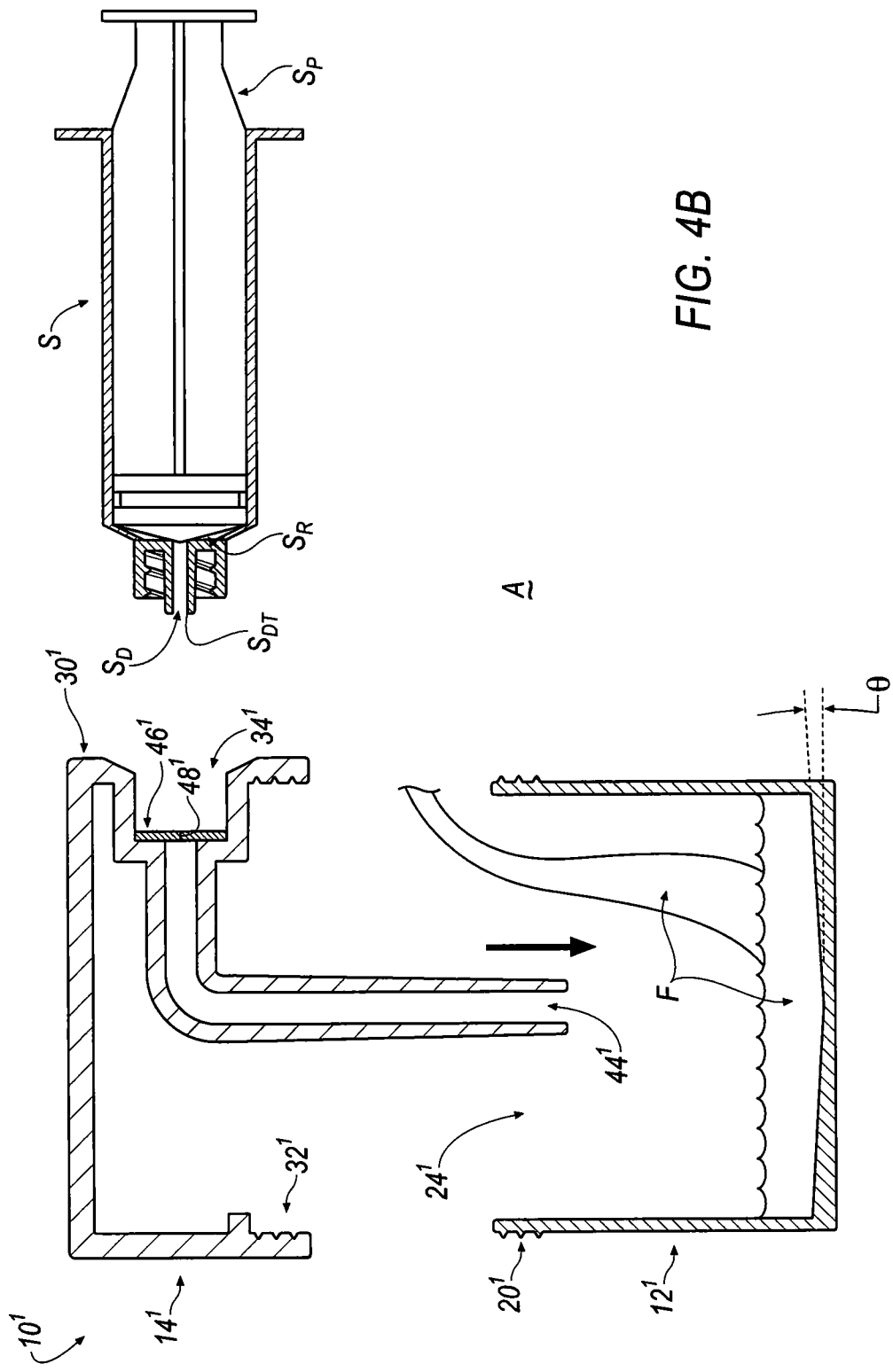
FIGS. 4B-4E illustrate a method of utilizing the container assembly of FIG. 4A.
Figure 4C:
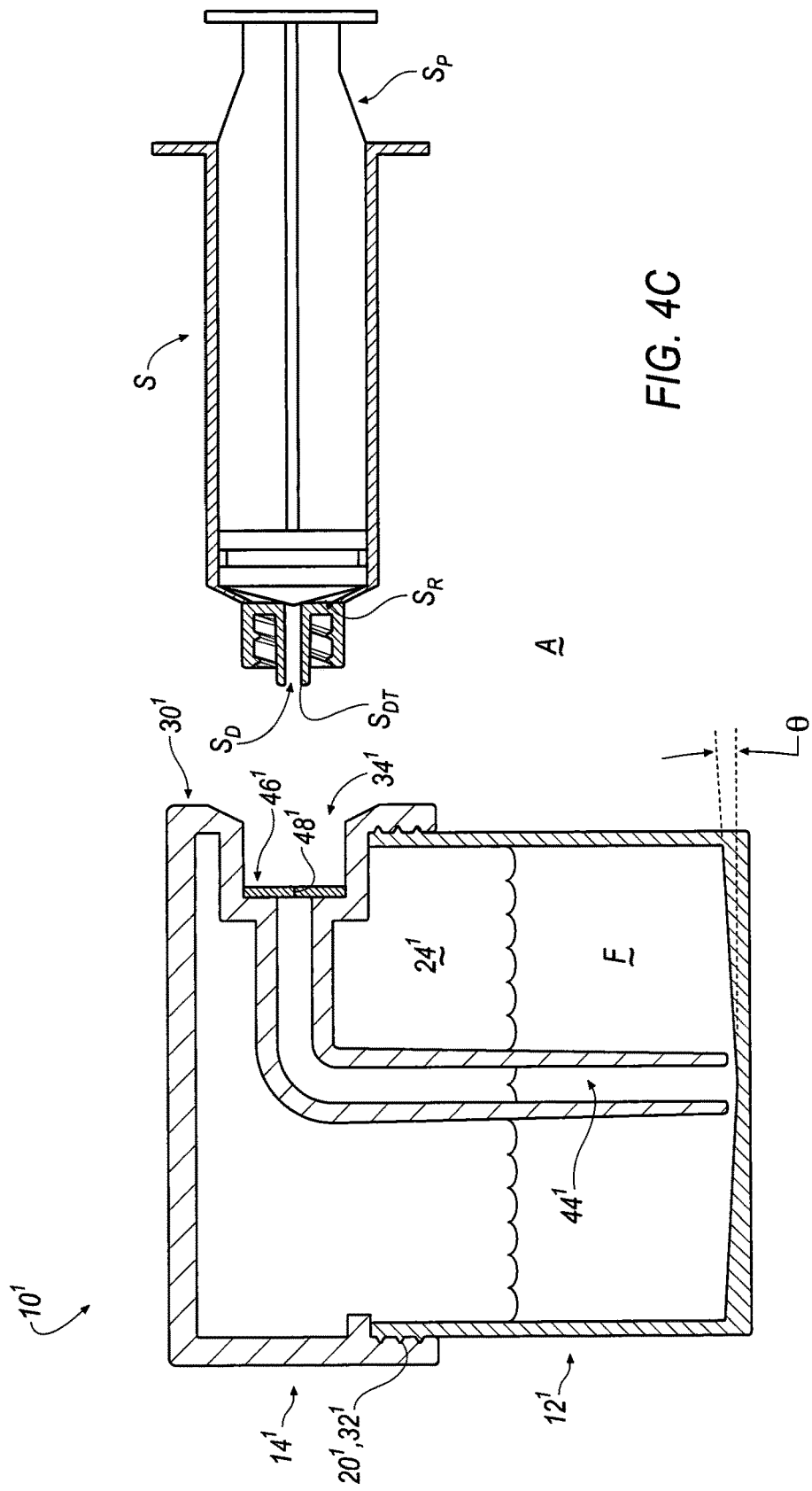
Figure 4D:
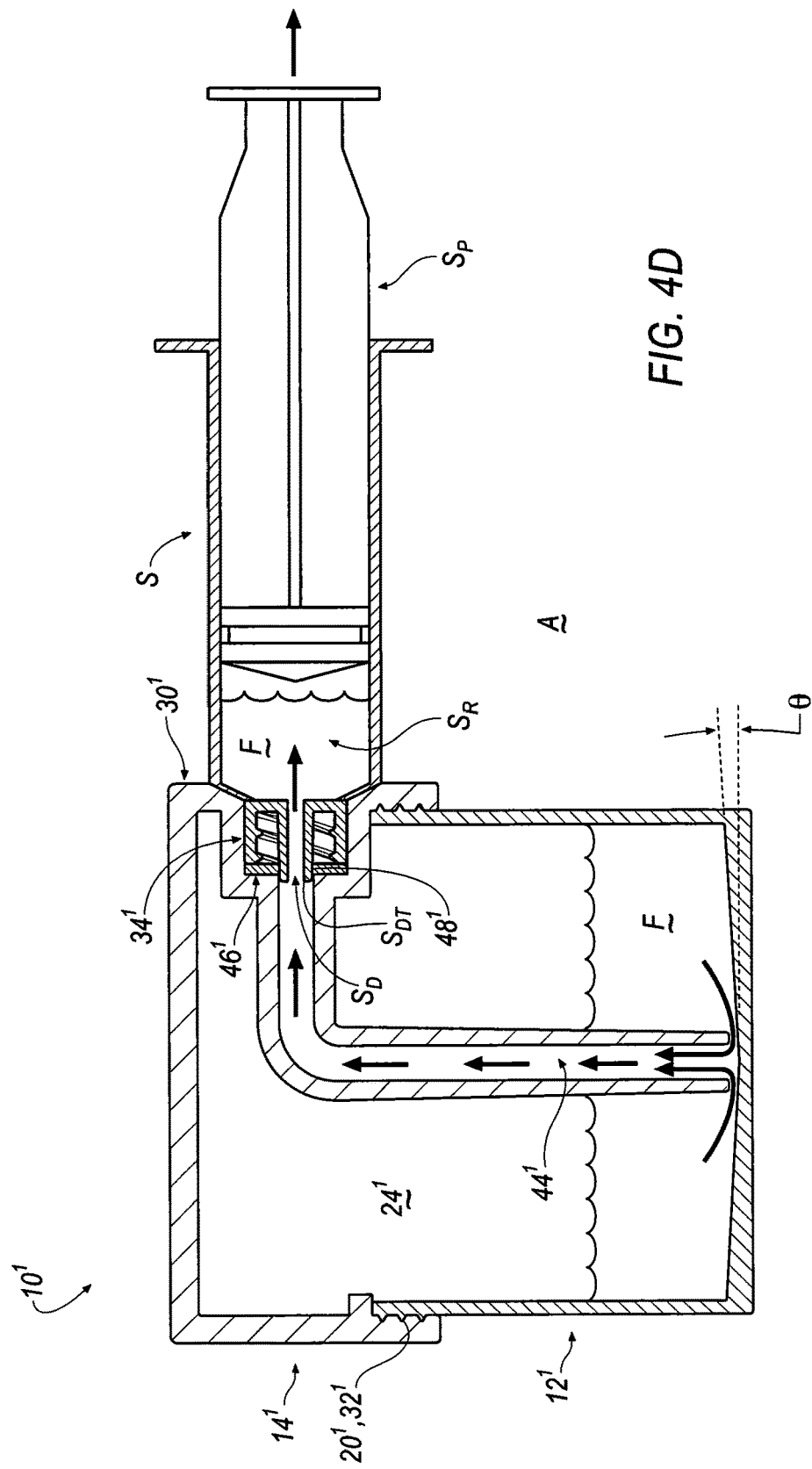
Figure 4E:
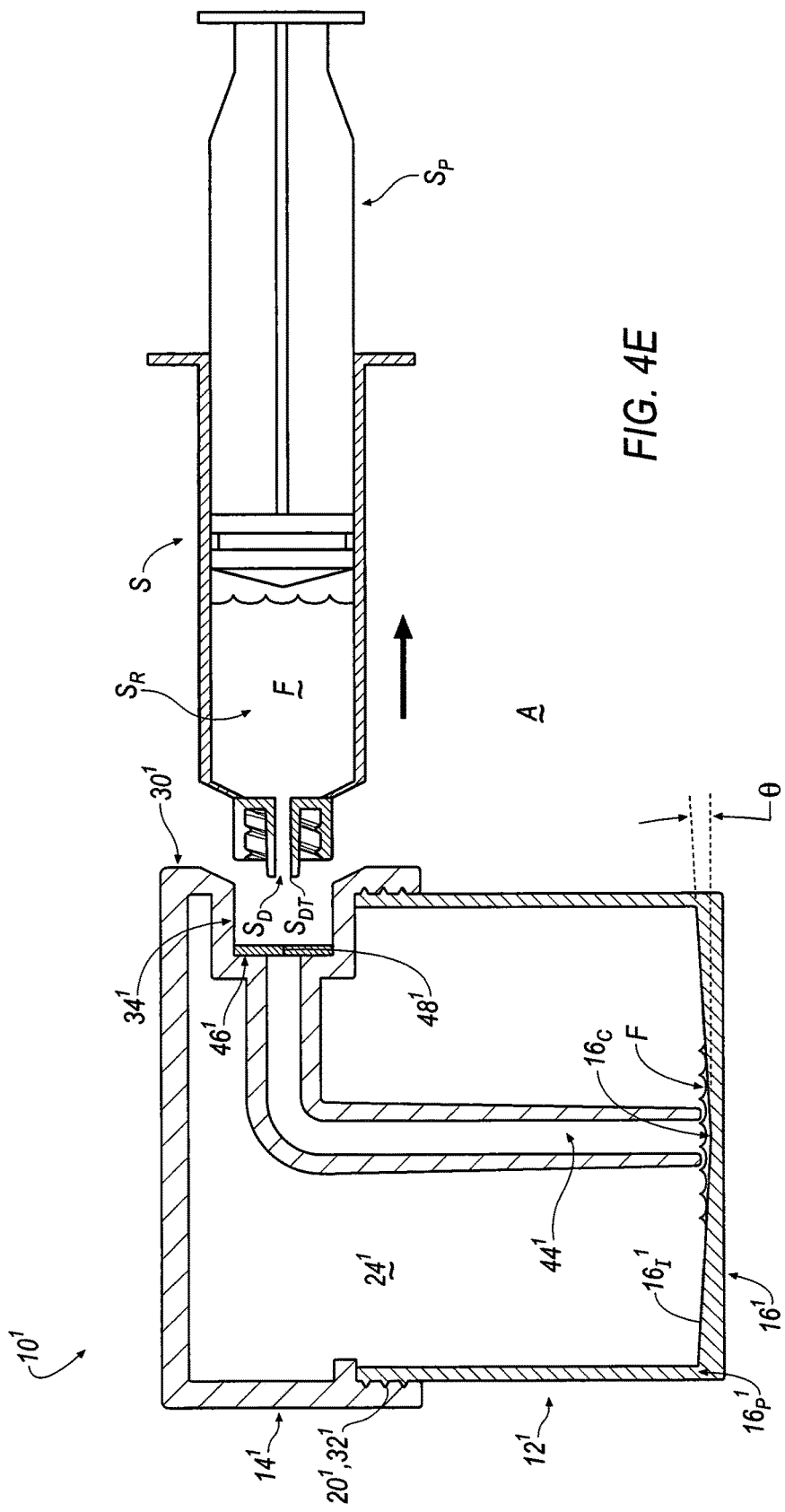

Referring to FIGS. 4B-4E, a method for utilizing the container assembly $10^1$ is described. Referring firstly to FIG. 4B, the container closure $14^1$ may be arranged in a disengaged state with respect to the container $12^1$, and, a fluid, F, is disposed within the fluid reservoir $24^1$. Referring to FIG. 4C, the container closure $14^1$ may be threadingly-connected to the container $12^1$ by the cooperating threaded surfaces $20^1$, $32^1$ of the container $12^1$ and container closure $14^1$ thereby fluidly sealing the fluid reservoir $24^1$ from surrounding atmosphere, A. Once the container closure $14^1$ is secured to the container $12^1$, the distal end, $S_D$, of the syringe, S, may be aligned with and arranged over the syringe-receiving bore $34^1$ formed in the side wall $30^1$ of the container closure $14^1$.

Referring to FIG. 4D, the distal end, $S_D$, of the syringe, S, is inserted into the syringe-receiving bore $34^1$ and the distal tip, $S_{DT}$, of the syringe, S, axially penetrates the slit $48^1$ to thereby arrange a fluid reservoir, $S_R$, of the syringe, S, in fluid communication with the fluid-flow passage $44^1$ that is in fluid communication with the fluid, F, contained by the fluid reservoir $24^1$. Once the fluid reservoir, $S_R$, of the syringe, S, is in fluid communication with the fluid-flow passage $44^1$ as described above, a user may axially manipulate a plunger, $S_P$, of the syringe, S, in order to draw the fluid, F, from the fluid reservoir $24^1$ into the fluid reservoir, $S_R$, of the syringe, S, by way of the fluid-flow passage $44^1$.

Referring to FIG. 4E, once the user has withdrawn a desired amount of fluid, F, from the fluid reservoir $24^1$ and into the fluid reservoir, $S_R$, of the syringe, S, the user may remove the syringe, S, from the syringe-receiving bore $34^1$. Once the distal end, $S_D$, of the syringe, S, is withdrawn from the syringe-receiving bore $34^1$, the distal tip, $S_{DT}$, of the syringe, S, no longer penetrates the slit $48^1$, and, as a result, the disk-shaped member $46^1$ may return to its pre-penetrated state, thereby fluidly sealing the fluid-flow passage 44 and the fluid reservoir $24^1$ from surrounding atmosphere, A.

As seen in FIG. 4E, the conically-pitched angle, θ, formed by the inner surface $16_I^1$ of the end wall $16^1$, directs a remainder of non-withdrawn fluid, F, disposed upon the inner surface $16_I^1$ of the end wall $16^1$ (with the assistance of gravity) away from the outer perimeter portion $16_P^1$ of the end wall $16^1$ and toward the central portion $16_C^1$ of the end wall $16^1$; as a result, the remainder of the non-withdrawn fluid, F, may be arranged/aligned with the fluid-flow passage $44^1$ for subsequent withdrawal from the container $12^1$.

Figure 5:
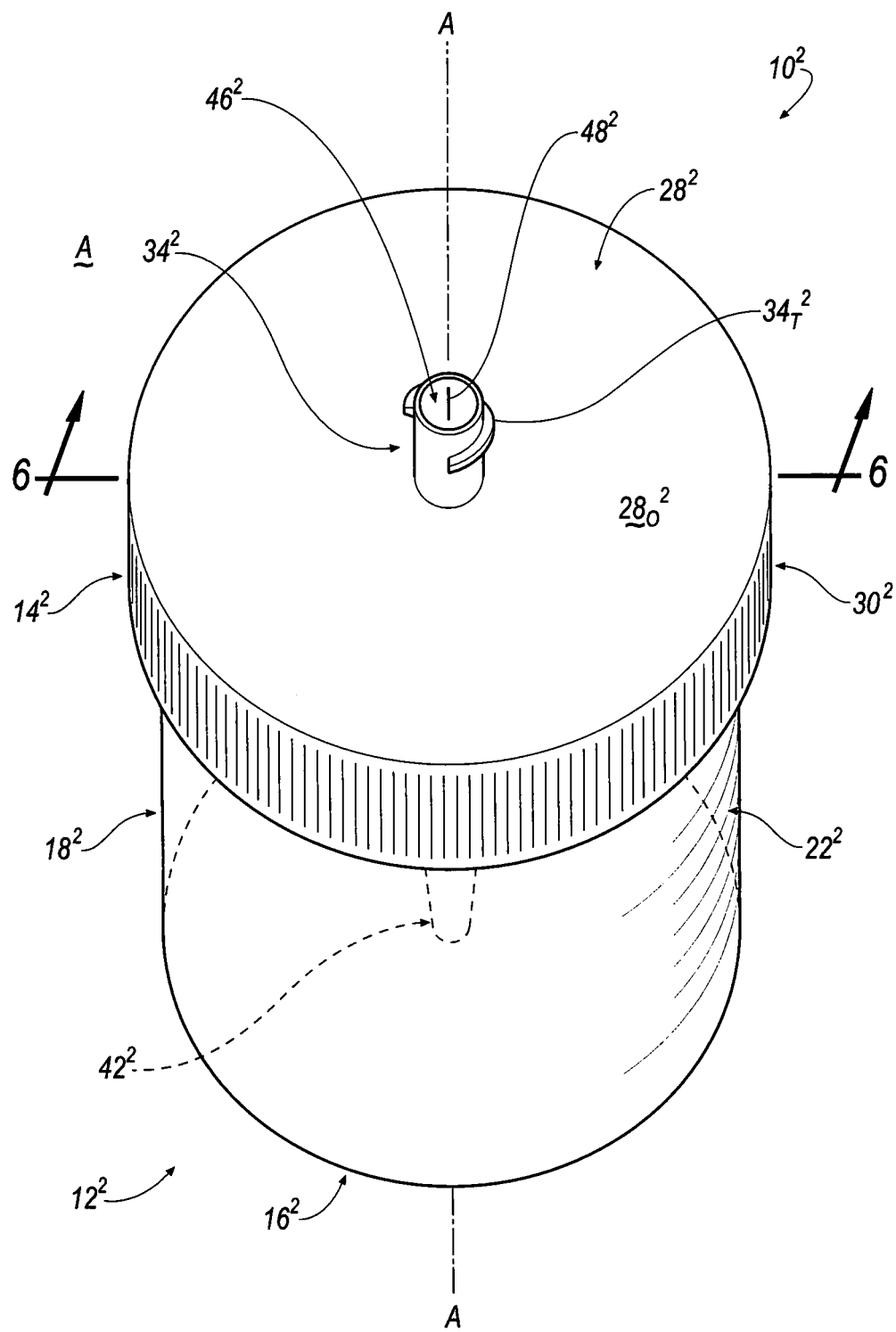
FIG. 5 illustrates a perspective view of a container assembly in accordance with an exemplary embodiment of the invention.

An exemplary container assembly is shown generally at $10^2$ in FIG. 5. The container assembly $10^2$ generally includes a container $12^2$ and a container closure $14^2$.

Figure 6A:
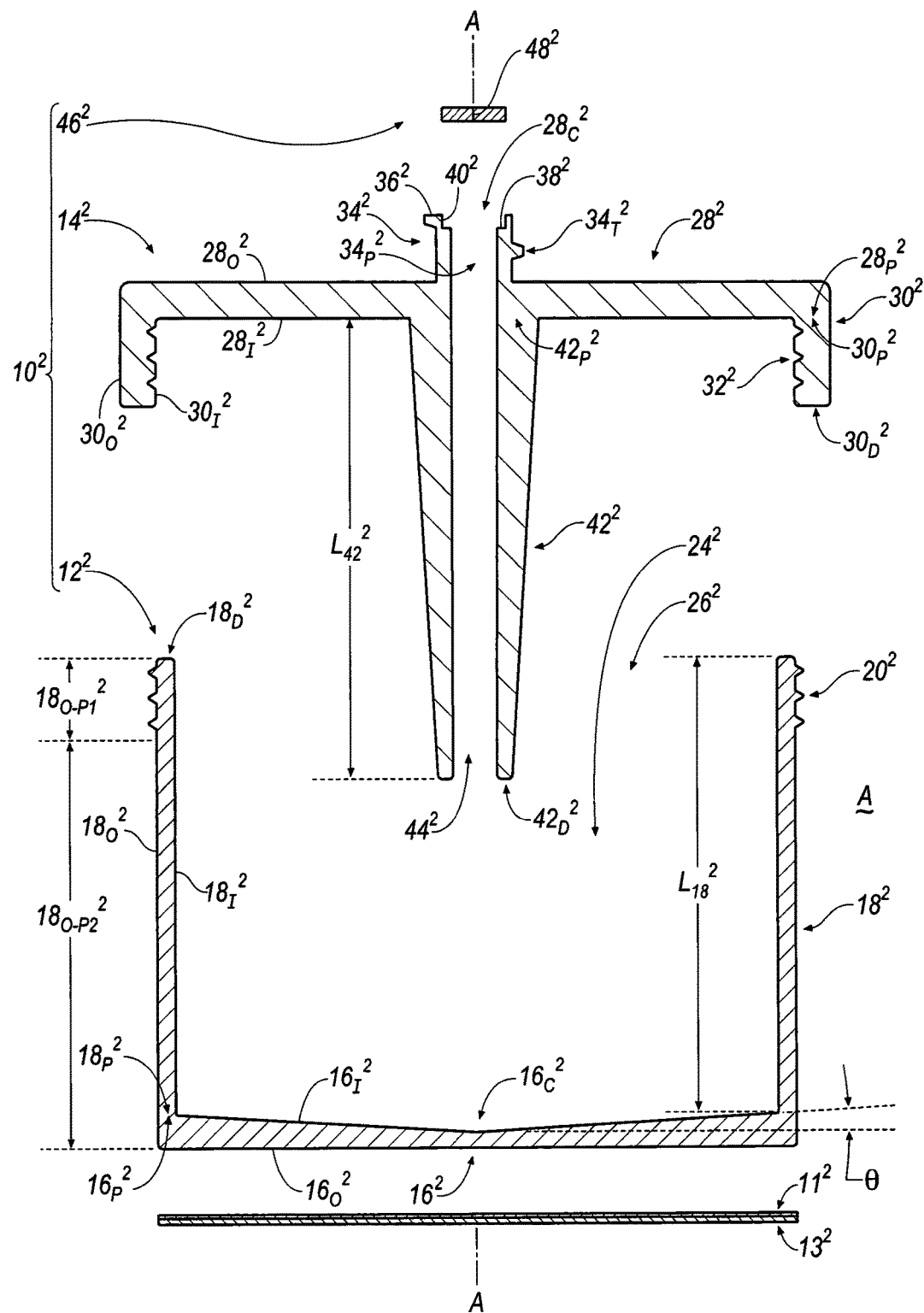
FIG. 6A is an exploded cross-sectional view of the container assembly according to line 6-6 of FIG. 5.

Referring to FIG. 6A, the container $12^2$ includes an end wall $16^2$ and a side wall $18^2$. The end wall $16^2$ and the side wall $18^2$ may include any desirable material or geometry. In some instances, the container $12^2$ may include a clear plastic or glass material; in some implementations, the material may include a coating (e.g., an antimicrobial coating). In some examples as seen in FIG. 5, the end wall $16^2$ may define an annular member and the side wall $18^2$ may define a cylindrical, tube-shaped body.

As seen in FIG. 6A, the end wall $16^2$ includes a central portion $16^2$ and an outer perimeter portion $16_P^2$. The side wall $18^2$ includes a proximal end $18_P^2$ and a distal end $18_D^2$. The proximal end $18_P^2$ of the side wall $18^2$ is connected to and extends away from the outer perimeter portion $16_P^2$ of the end wall $16^2$.

The end wall $16^2$ includes an inner surface $16_I^2$ and an outer surface $16_O^2$. The inner surface $16_I^2$ of the end wall $16^2$ may be conically-pitched according to an angle, θ, to define the central portion $16_C^2$ of the end wall $16^2$ the container $12^2$ to be a low point of the inner surface $16_I^2$ of the end wall $16^2$ of the container $12^2$. In some instances, the angle may be approximately equal to 15°. In some examples, the container $12^2$ may optionally include an adhesive $11^2$ applied over the outer surface $16_O^2$ of the end wall $16^2$. In some instances, an optional release paper $13^2$ may be applied over the adhesive $11^2$. Prior to disposing the container $12^2$ upon a support surface, a user may remove the release paper (thereby exposing the adhesive $11^2$ applied over the outer surface $16_O^2$ of the end wall $16^2$); the exposed adhesive $13^2$ may assist in the prevention of movement of the container $12^2$ upon the support surface once the outer surface $16_O^2$ of the end wall $16^2$ is arranged upon the support surface.

The side wall $18^2$ includes an inner surface $18_I^2$ and an outer surface $18_O^2$. A first portion $18_{O-1}^2$ of the outer surface $18_O^2$ of the side wall $18^2$ may define an outer threaded surface $20^2$ of the container $12^2$. A second portion $18_{O-P2}^2$ of the outer surface $18_O^2$ of the side wall $18^2$ may include printed indicia $22^2$ (as seen in FIG. 5) defining, for example, an amount of fluid disposed within the container $12^2$. As will be described in the following disclosure, the outer threaded surface $20^2$ of the container $12^2$ may cooperate with an inner threaded surface $32^2$ of the container closure $14^2$ for selectively attaching the container closure $14^2$ to the container $12^2$.

The container $12^2$ forms a fluid reservoir $24^2$ that is defined by the inner surface $16_I^2$, $18_I^2$ of both of the end wall $16^2$ and the side wall $18^2$. Access to the fluid reservoir $24^2$ is permitted by an opening $26^2$ formed by the distal end $18_D^2$ of the side wall $18^2$.

Referring to FIG. 6A, the container closure $14^2$ includes an end wall $28^2$ and a side wall $30^2$. The end wall $28^2$ and the side wall $30^2$ may include any desirable material or geometry. In some instances, the container closure $14^2$ may include an opaque plastic material; in some implementations, the material may include a coating (e.g., an antimicrobial coating). In some examples as seen in FIG. 5, the end wall $28^2$ may define an annular member and the side wall $30^2$ may define a cylindrical, tube-shaped body.

As seen in FIG. 6A, the end wall $28^2$ includes a central portion $28_C^2$ and an outer perimeter portion $28_P^2$. The side wall $30^2$ includes a proximal end $30_P^2$ and a distal end $30_D^2$. The proximal end $30_P^2$ of the side wall $30^2$ is connected to and extends away from the outer perimeter portion $28_P^2$ of the end wall $28^2$. The central portion $28_C^2$ of the end wall $28^2$ of the container closure $14^2$ and the central portion $16_C^2$ of the end wall $16^2$ of the container $12^2$ may be aligned with a central axis, A-A, extending through the container assembly $10^2$.

The end wall $28^2$ includes an inner surface $28_I^2$ and an outer surface $28_O^2$. The side wall $30^2$ includes an inner surface $30_I^2$ and an outer surface $30_O^2$. The inner surface $30_I^2$ of the side wall $30^2$ may define an inner threaded surface $32^2$ of the container closure $14^2$. As will be described in the following disclosure, the inner threaded surface $32^2$ of the container closure $14^2$ may cooperate with the outer threaded surface $20^2$ of the container $12^2$ for selectively attaching the container closure $14^2$ to the container $12^2$.

The container closure $14^2$ may further include a syringe-engaging portion $34^2$ formed by and extending axially-away from the outer surface $28_O^2$ of the end wall $28^2$ of the container closure $14^2$. The syringe-engaging portion $34^2$ is axially aligned with the central portion $28_C^2$ of the end wall $28^2$ of the container closure $14^2$. An axial center of the syringe-engaging portion $34^2$ is aligned with the central axis, A-A. The syringe-engaging portion $34^2$ is generally defined by a substantially cylindrical tube-shaped member having an outer threaded surface $34_T^2$.

Figure 6C:
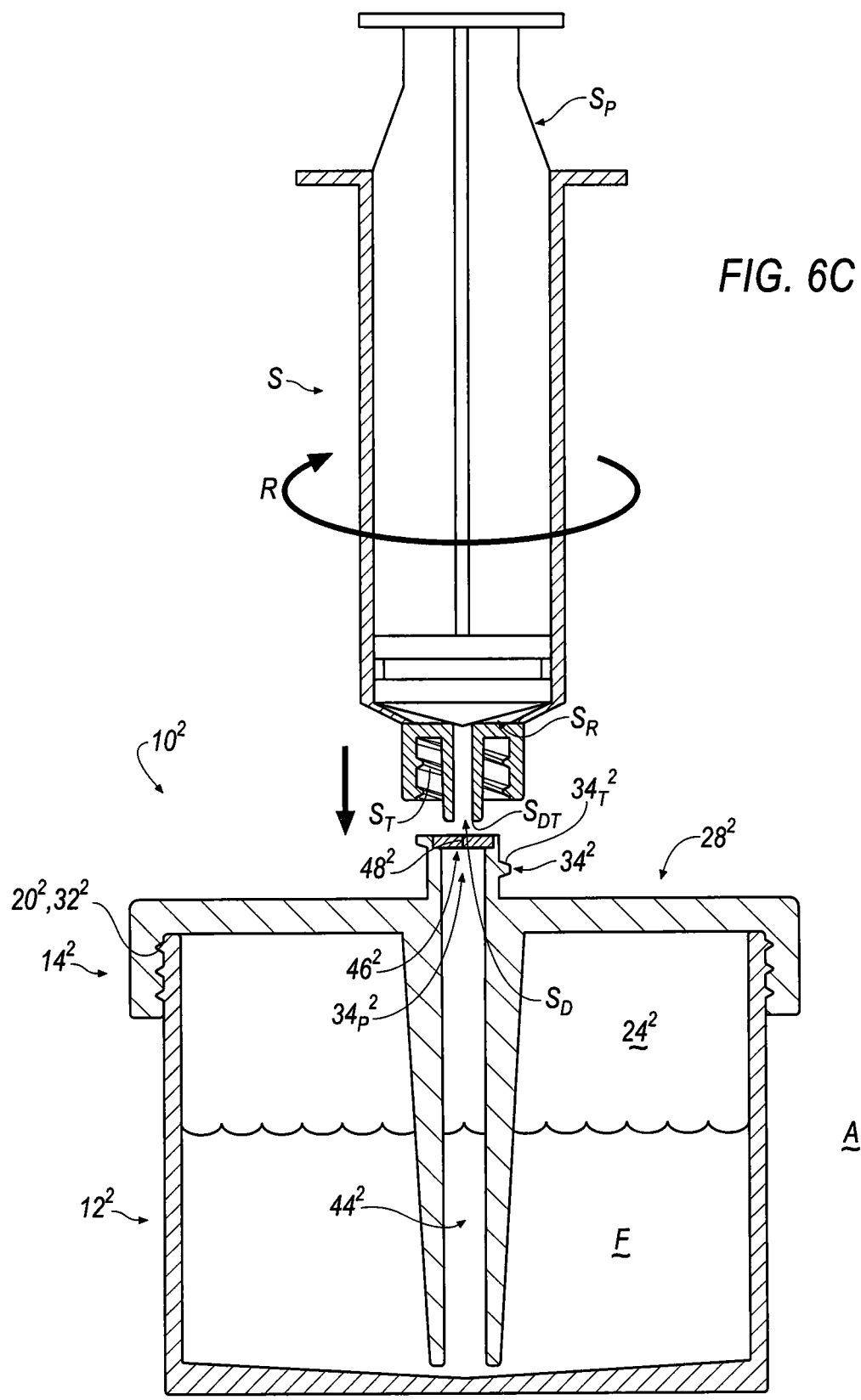

As will be seen in the following disclosure at FIGS. 6C-6D, the outer threaded surface $34_T^2$ of the syringe-engaging portion $34^2$ engages an inner threaded surface portion, $S_T$ (as seen in, e.g., FIG. 6B), of the syringe, S, which may be referred to as a Luer lock. The substantially cylindrical tube-shaped member defining the syringe-engaging portion $34^2$ is sized for being correspondingly inserted into a distal end, $S_D$, of a syringe, S, which is defined by an outer tube-shaped member (having the inner threaded surface, $S_T$) and an inner tube-shaped member. The inner tube-shaped member defines a distal tip, $S_{DT}$, of the syringe, S, that is inserted into a passage $34_P^2$ formed by the cylindrical tube-shaped member of the syringe-engaging portion $34^2$.

Referring to FIG. 6A, a distal end of the syringe-engaging portion $34^2$ may be defined by portions $36^2$, $38^2$, $40^2$ of the outer surface $28_O^2$ of the end wall $28^2$ of the container closure $14^2$, and includes, for example: a first shoulder surface $36^2$, a second shoulder surface $38^2$ and an axial wall surface $40^2$ extending substantially perpendicularly from the second shoulder surface $38^2$ and connects the first shoulder surface $36^2$ to the second shoulder surface $38^2$.

The container closure $14^2$ also includes a fluid-drawing member $42^2$ that extends axially away from and is integral with the inner surface $28_I^2$ of the end wall $28^2$ of the container closure $14^2$. The fluid-drawing member $42^2$ includes a proximal end $42_P^2$ and a distal end $42_D^2$. A fluid-flow passage $44^2$ extends through the fluid-drawing member $42^2$ between the proximal end $42_P^2$ and the distal end $42_D^2$. The fluid-flow passage $44^2$ also axially extends into the syringe-engaging portion $34^2$. The fluid-flow passage $44^2$ is aligned with an axial center of the fluid-drawing member $42^2$. When the container closure $14^2$ is connected to the container $12^2$, the fluid-flow passage $44^2$ is in fluid communication with the fluid reservoir $24^2$ defined by the container $12^2$.

The proximal end $42_P^2$ of the fluid-drawing member $42^2$ is connected to and extends away from the inner surface $28_I^2$ of the end wall $28^2$ of the container closure $14^2$. In some instances, the fluid-drawing member $42^2$ may extend away from the inner surface $28_I^2$ at the central portion $28_C^2$ of the end wall $28^2$ of the container closure $14^2$ (such that the fluid-drawing member $42^2$ is aligned with the central axis, A-A, when the container closure $14^2$ is attached to the container $12^2$).

The fluid-drawing member $42^2$ may also be defined by a length dimension, $L_{42}{}^2$. The length dimension $L_{42}{}^2$ of the fluid-drawing member $42^2$ may be approximately equal to, but slightly greater than a length $L_{18}{}^2$ of the side wall $18^2$ of the container $12^2$; due to the conically-pitched angle, θ, formed by the inner surface $16_I{}^2$ of the end wall $16^2$, upon connecting the container closure $14^2$ to the container $12^2$, the distal end $42_D{}^2$ of the fluid-drawing member $42^2$ may be arranged substantially adjacent to but in a slightly spaced-apart relationship with respect to the inner surface $16_I{}^2$ of the end wall $16^2$ defined by the central portion $16_C{}^2$ of the end wall $16^2$ that is aligned with the central axis, A-A. By selectively defining the length relationship of the length dimensions $L_{42}{}^2$, $L_{18}{}^2$ of the fluid-drawing member $42^2$ and the side wall $18^2$, and, in addition, the axial alignment of the fluid-drawing member $42^2$ with respect to the central portion $28_C{}^2$ of the end wall $28^2$ of the container closure $14^2$, the fluid drawing member $42^2$ is selectively positioned relative to the container $12^2$ in order to draw a remainder of fluid, F, contained within the fluid reservoir $24^2$ when all of the fluid, F, contained within the container $12^2$ is nearly depleted as seen in FIG. 6E.

The container assembly $10^2$ also includes a disk-shaped member $46^2$ that is disposed upon and supported by one or both of the second shoulder surface $38^2$ and the axial wall surface $40^2$ defined by the distal end of the syringe-engaging portion $34^2$. The disk-shaped member $46^2$ may be secured to one or more of the second shoulder surface $38^2$ and the axial wall surface $40^2$ in any desirable fashion (e.g., with an adhesive or a friction-fit connection). The disk-shaped member $46^2$ may be formed from any desirable material including, for example, foam, rubber or the like. The disk-shaped member $46^2$ inhibits contaminates from surrounding atmosphere, A, from entering the fluid-flow passage $44^2$ and into the fluid reservoir $24^2$.

The disk-shaped member $46^2$ may include a slit $48^2$ that is aligned with an axial center of both of the container closure $14^2$ and the disk-shaped member $46^2$. The slit $48^2$ selectively permits selective fluid communication with the fluid-flow passage $44^2$ and the fluid reservoir $24^2$ from surrounding atmosphere, A. Access to (i.e., fluid communication) with the fluid-flow passage $44^2$ from a device (e.g., the syringe, S) that is located in surrounding atmosphere, A, is permitted when a distal tip, $S_{DT}$, of the syringe, S, axially penetrates the slit $48^2$, as seen in FIG. 6D Referring to FIGS. 6B-6E, a method for utilizing the container assembly $10^2$ is described. Referring firstly to FIG. 6B, the container closure $14^2$ is shown disengaged from the container $12^2$, and, a fluid, F, is disposed within the fluid reservoir $24^2$. Referring to FIG. 6C, the container closure $14^2$ is connected (e.g., threadingly-connected) to the container $12^2$ by, for example, the cooperating threaded surfaces $20^2$, $32^2$ of the container $12^2$ and container closure $14^2$ thereby fluidly sealing the fluid reservoir $24^2$ from surrounding atmosphere, A. Once the container closure $14^2$ is secured to the container $12^2$, the distal end, $S_D$, of the syringe, S, may be aligned with and arranged over the syringe-engaging portion $34^2$ extending axially away from the central portion $28_C{}^2$ of the end wall $28^2$ of the container closure $14^2$. The syringe, S, may be connected to the syringe-engaging portion $34^2$ by axially rotating, R, the syringe, S, relative to the syringe-engaging portion $34^2$ such that the inner threaded surface portion, $S_T$, of the syringe, S, threadingly-engages the outer threaded surface $34_T{}^2$ of the syringe-engaging portion $34^2$.

Figure 6D:
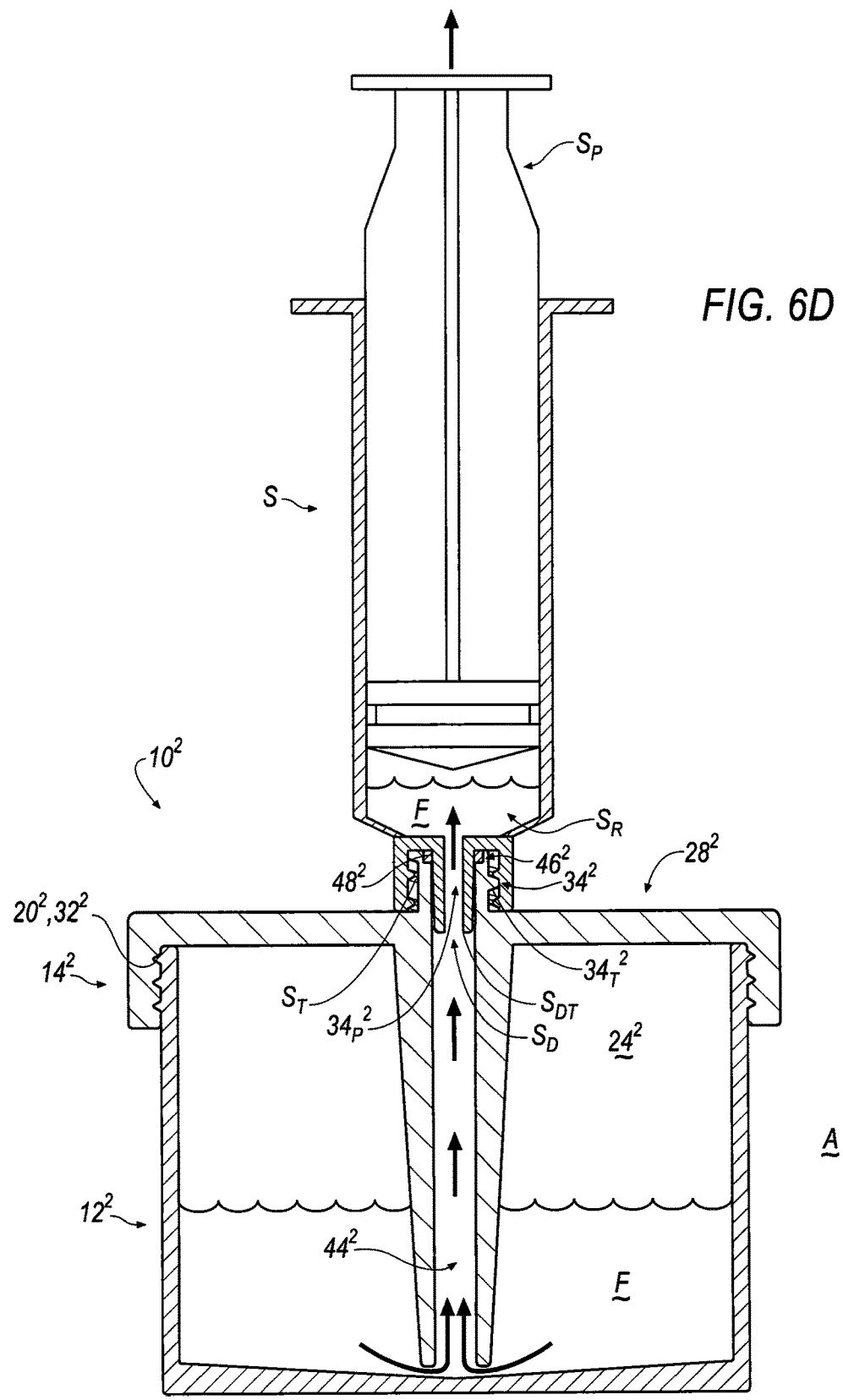
Figure 6E:
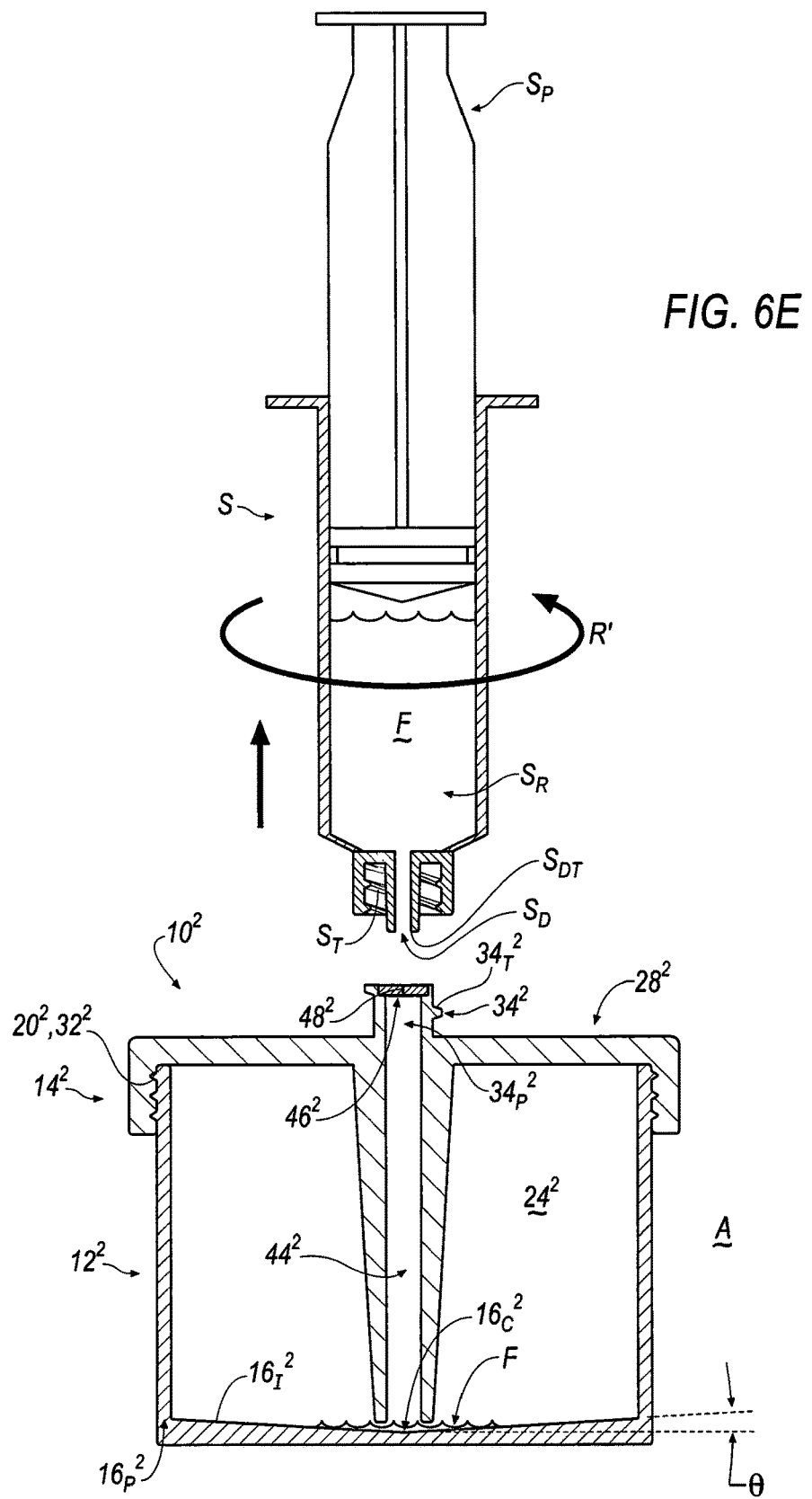

Referring to FIG. 6D, once the distal end, $S_D$, of the syringe, S, is threadingly-connected to the syringe-engaging portion $34^2$, the distal tip, $S_{DT}$, of the syringe, S, axially penetrates the slit $48^2$ to thereby arrange a fluid reservoir, $S_R$, of the syringe, S, is in fluid communication with the fluid-flow passage $44^2$ that is in fluid communication with the fluid, F, contained by the fluid reservoir $24^2$. Once the fluid reservoir, $S_R$, of the syringe, S, is in fluid communication with the fluid-flow passage $44^2$ as described above, a user may axially manipulate a plunger, $S_P$, of the syringe, S, in order to draw the fluid, F, from the fluid reservoir $24^2$ into the fluid reservoir, $S_R$, of the syringe, S, by way of the fluid-flow passage $44^2$.

Referring to FIG. 6E, once the user has withdrawn a desired amount of fluid, F, from the fluid reservoir $24^2$ and into the fluid reservoir, $S_R$, of the syringe, S, the user may axially rotate, R', the syringe, S, in a direction opposite that of the rotational direction, R, in order to axially disconnect the distal end, $S_D$, of the syringe, S, from the syringe-engaging portion $34^2$. Once the distal end, $S_D$, of the syringe, S, is withdrawn from the syringe-engaging portion $34^2$, the distal tip, $S_{DT}$, of the syringe, S, no longer penetrates the slit $48^2$, and, as a result, the disk-shaped member $46^2$ may return to its pre-penetrated state, thereby fluidly sealing the fluid flow passage $44^2$ and the fluid reservoir $24^2$ from surrounding atmosphere, A.

As seen in FIG. 6E, the conically-pitched angle, θ, formed by the inner surface $16_I{}^2$ of the end wall $16^2$, directs a remainder of non-withdrawn fluid, F, disposed upon the inner surface $16_I{}^2$ of the end wall $16^2$ (with the assistance of gravity) away from the outer perimeter portion $16_P{}^2$ of the end wall $16^2$ and toward the central portion $16_C{}^2$ of the end wall $16^2$; as a result, the remainder of the non-withdrawn fluid, F, may be arranged/aligned with the fluid-flow passage $44^2$ for subsequent withdrawal from the container $12^2$.

Figure 7:
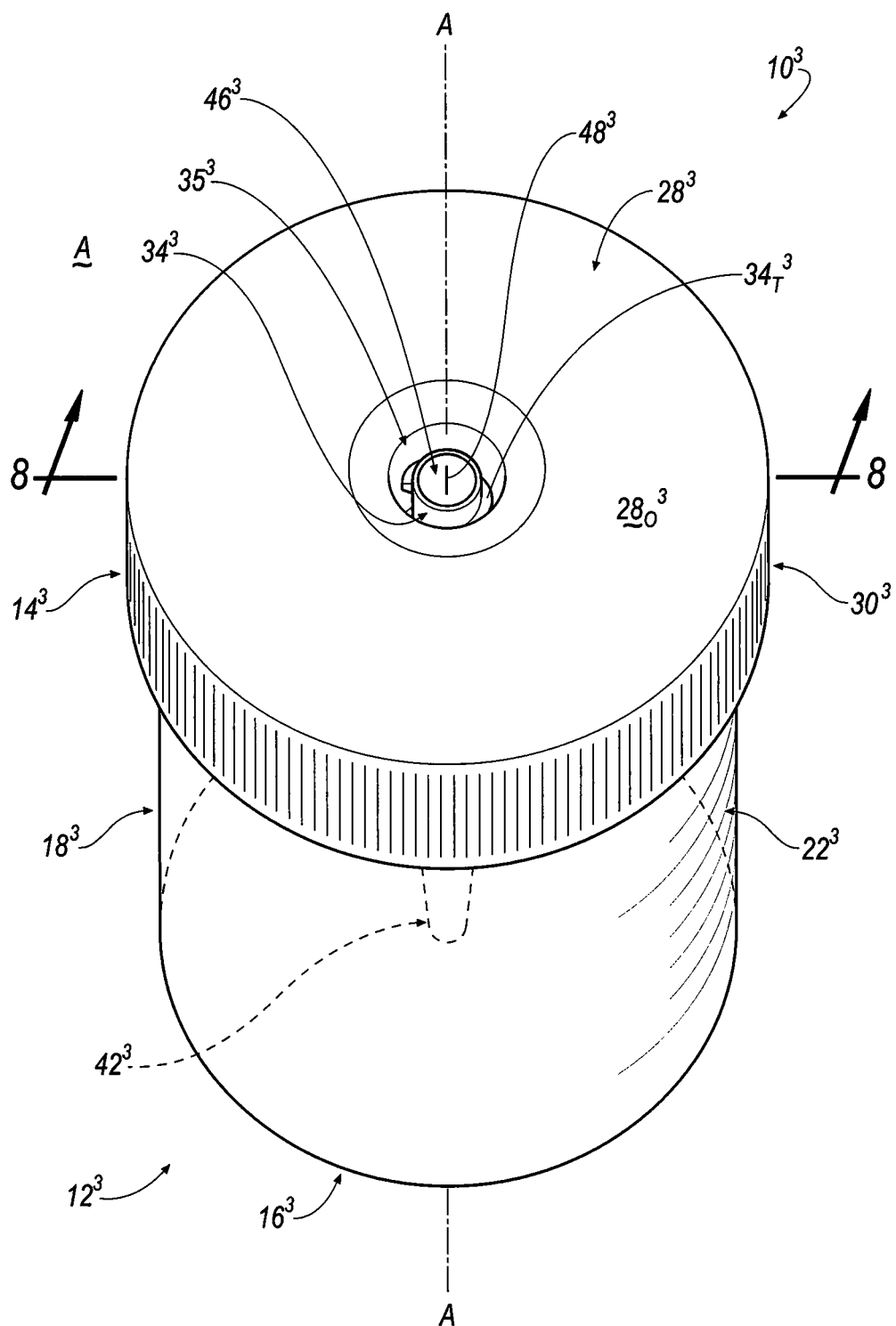
FIG. 7 illustrates a perspective view of a container assembly in accordance with an exemplary embodiment of the invention.

An exemplary container assembly is shown generally at $10^3$ in FIG. 7. The container assembly $10^3$ generally includes a container $12^3$ and a container closure $14^3$.

Figure 8A:
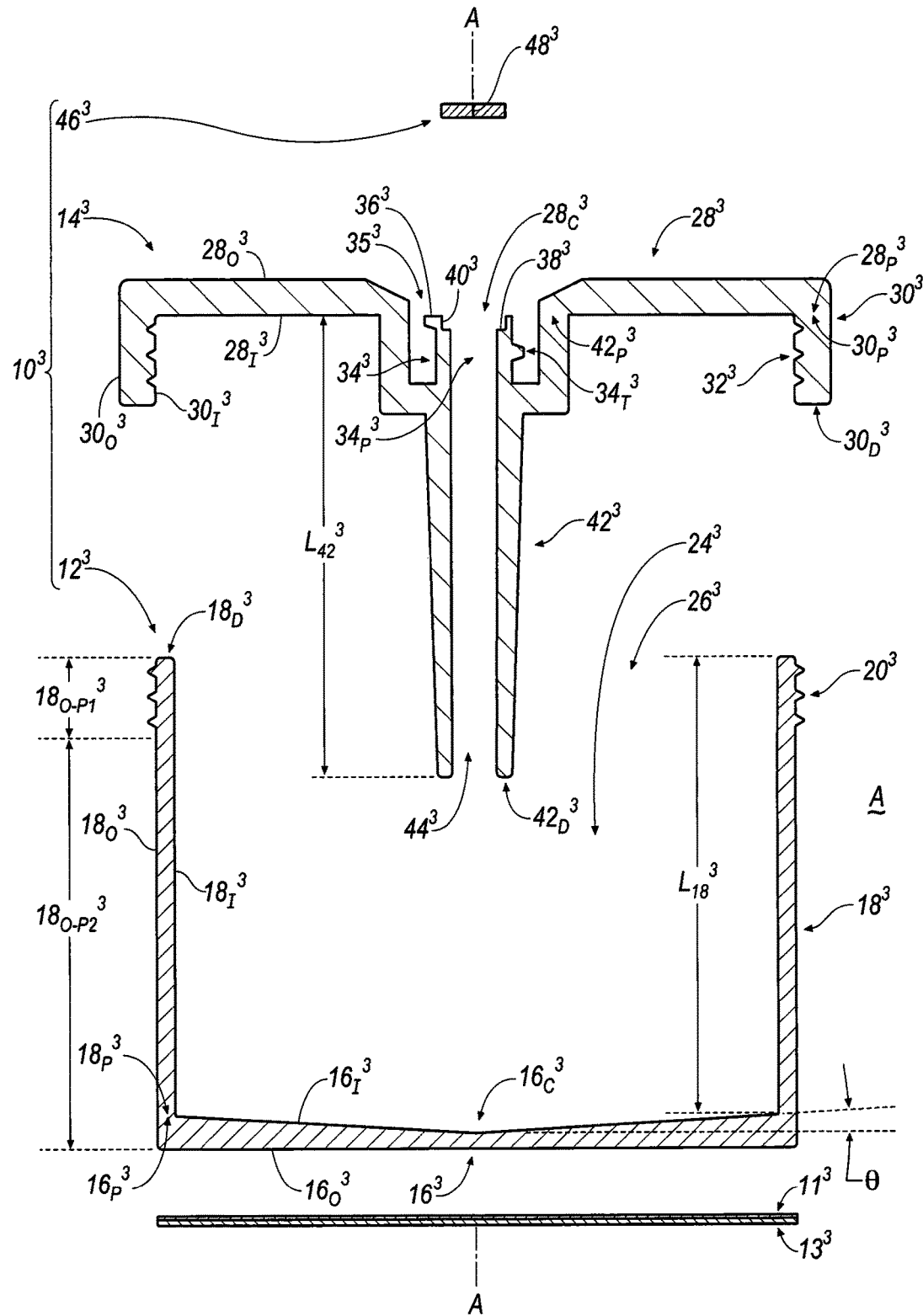
FIG. 8A is an exploded cross-sectional view of the container assembly according to line 8-8 of FIG. 7.

Referring to FIG. 8A, the container $12^3$ includes an end wall $16^3$ and a side wall $18^3$. The end wall $16^3$ and the side wall $18^3$ may include any desirable material or geometry. In some instances, the container $12^3$ may include a clear plastic or glass material; in some implementations, the material may include a coating (e.g., an antimicrobial coating). In some examples as seen in FIG. 7, the end wall $16^3$ may define an annular member and the side wall $18^3$ may define a cylindrical, tube-shaped body.

As seen in FIG. 8A, the end wall $16^3$ includes a central portion $16_C{}^3$ and an outer perimeter portion $16_P{}^3$. The side wall $18^3$ includes a proximal end $18_P{}^3$ and a distal end $18_D{}^3$. The proximal end $18_P{}^3$ of the side wall $18^3$ is connected to and extends away from the outer perimeter portion $16_P{}^3$ of the end wall $16^3$.

The end wall $16^3$ includes an inner surface $16_I{}^3$ and an outer surface $16_O{}^3$. The inner surface $16_I{}^3$ of the end wall $16^3$ may be conically-pitched according to an angle, θ, to define the central portion $16^3$ of the end wall $16^3$ the container $12^3$ to be a low point of the inner surface $16_I{}^3$ of the end wall $16^3$ of the container $12^3$. In some instances, the angle may be approximately equal to 15°. In some examples, the container $12^3$ may optionally include an adhesive $11^3$ applied over the outer surface $16_O{}^3$ of the end wall $16^3$. In some instances, an optional release paper $13^3$ may be applied over the adhesive $11^3$. Prior to disposing the container $12^3$ upon a support surface, a user may remove the release paper (thereby exposing the adhesive $11^3$ applied over the outer surface $16_O^3$ of the end wall $16^3$); the exposed adhesive $13^3$ may assist in the prevention of movement of the container $12^3$ upon the support surface once the outer surface $16_O^3$ of the end wall $16^3$ is arranged upon the support surface.

The side wall $18^3$ includes an inner surface $18_I^3$ and an outer surface $18_O^3$. A first portion $18_{O-P1}^3$ of the outer surface $18_O^3$ of the side wall $18^3$ may define an outer threaded surface $20^3$ of the container $12^3$. A second portion $18_{O-P2}^3$ of the outer surface $18_O^3$ of the side wall $18^3$ may include printed indicia $22^3$ (as seen in FIG. 7) defining, for example, an amount of fluid disposed within the container $12^3$. As will be described in the following disclosure, the outer threaded surface $20^3$ of the container $12^3$ may cooperate with an inner threaded surface $32^3$ of the container closure $14^3$ for selectively attaching the container closure $14^3$ to the container $12^3$.

The container $12^3$ forms a fluid reservoir $24^3$ that is defined by the inner surface $16_I^3$, $18_I^3$ of both of the end wall $16^3$ and the side wall $18^3$. Access to the fluid reservoir $24^3$ is permitted by an opening $26^3$ formed by the distal end $18_D^3$ of the side wall $18^3$.

Referring to FIG. 8A, the container closure $14^3$ includes an end wall $28^3$ and a side wall $30^3$. The end wall $28^3$ and the side wall $30^3$ may include any desirable material or geometry. In some instances, the container closure $14^3$ may include an opaque plastic material; in some implementations, the material may include a coating (e.g., an antimicrobial coating). In some examples as seen in FIG. 7, the end wall $28^3$ may define an annular member and the side wall $30^3$ may define a cylindrical, tube-shaped body.

As seen in FIG. 8A, the end wall $28^3$ includes a central portion $28_C^3$ and an outer perimeter portion $28_P^3$. The side wall $30^3$ includes a proximal end $30_P^3$ and a distal end $30_D^3$. The proximal end $30_P^3$ of the side wall $30^3$ is connected to and extends away from the outer perimeter portion $28_P^3$ of the end wall $28^3$. The central portion $28_C^3$ of the end wall $28^3$ of the container closure $14^3$ and the central portion $16_C^3$ of the end wall $16^3$ of the container $12^3$ may be aligned with a central axis, A-A, extending through the container assembly $10^3$.

The end wall $28^3$ includes an inner surface $28_I^3$ and an outer surface $28_O^3$. The side wall $30^3$ includes an inner surface $30_I^3$ and an outer surface $30_O^3$. The inner surface $30_I^3$ of the side wall $30^3$ may define an inner threaded surface $32^3$ of the container closure $14^3$. As will be described in the following disclosure, the inner threaded surface $32^3$ of the container closure $14^3$ may cooperate with the outer threaded surface $20^3$ of the container $12^3$ for selectively attaching the container closure $14^3$ to the container $12^3$.

The container closure $14^3$ may further include a syringe-engaging portion $34^3$ formed by the outer surface $28_O^3$ of the end wall $28^3$ of the container closure $14^3$. The syringe-engaging portion $34^3$ is substantially similar to the syringe-engaging portion $34^2$ described above at FIGS. 5-6E with the exception that the syringe-engaging portion $34^3$ is recessed within a bore $35^3$ formed in the outer surface $28_O^3$ of the end wall $28^3$ of the container closure $14^3$ (rather than extending axially away from the outer surface $28_O^2$ of the end wall $28^2$ of the container closure $14^2$ as seen above at FIGS. 5-6E). By arranging the syringe-engaging portion $34^3$ in a recessed orientation within the bore $35^3$, the syringe-engaging portion $34^3$ is protected from being unintentionally sheared off of the outer surface $28_O^3$ of the end wall $28^3$ of the container closure $14^3$.

The syringe-engaging portion $34^3$ is axially-aligned with the central portion $28_C^3$ of the end wall $28^3$ of the container closure $14^3$. An axial center of the syringe-engaging portion $34^3$ is aligned with the central axis, A-A. The syringe-engaging portion $34^3$ is generally defined by a substantially cylindrical tube-shaped member having an outer threaded surface $34_T^3$. The outer threaded surface $34_T^3$ of the syringe-engaging portion $34^3$ engages an inner threaded surface portion, $S_T$ (see, e.g., FIG. 8B), of the syringe, S, which may be referred to as a Luer lock. The substantially cylindrical tube-shaped member defining the syringe-engaging portion $34^3$ is sized for being correspondingly inserted into a distal end, $S_D$, of a syringe, S, which is defined by an outer tube-shaped member (having the inner threaded surface, $S_T$) and an inner tube-shaped member. The inner tube-shaped member defines a distal tip, $S_{DT}$, of the syringe, S, that is inserted into a passage $34_P^3$ formed by the cylindrical tube-shaped member of the syringe-engaging portion $34^3$.

Referring to FIG. 8A, a distal end of the syringe-engaging portion $34^3$ may be defined by portions $36^3$, $38^3$, $40^3$ of the outer surface $28_O^3$ of the end wall $28^3$ of the container closure $14^3$, and includes, for example: a first shoulder surface $36^3$, a second shoulder surface $38^3$ and an axial wall surface $40^3$ extending substantially perpendicularly from the second shoulder surface $38^3$ and connects the first shoulder surface $36^3$ to the second shoulder surface $38^3$.

The container closure $14^3$ also includes a fluid-drawing member $42^3$ that extends axially away from and is integral with the inner surface $28_I^3$ of the end wall $28^3$ of the container closure $14^3$. The fluid-drawing member $42^3$ includes a proximal end $42_P^3$ and a distal end $42_D^3$. A fluid-flow passage $44^3$ extends through the fluid-drawing member $42^3$ between the proximal end $42_P^3$ and the distal end $42_D^3$. The fluid-flow passage $44^3$ also axially extends into the syringe-engaging portion $34^3$. The fluid-flow passage $44^3$ is aligned with an axial center of the fluid-drawing member $42^3$. When the container closure $14^3$ is connected to the container $12^3$, the fluid-flow passage $44^3$ is in fluid communication with the fluid reservoir $24^3$ defined by the container $12^3$.

The proximal end $42_P^3$ of the fluid-drawing member $42^3$ is connected to and extends away from the inner surface $28_I^3$ of the end wall $28^3$ of the container closure $14^3$. In some instances, the fluid-drawing member $42^3$ may extend away from the inner surface $28_I^3$ at the central portion $28_C^3$ of the end wall $28^3$ of the container closure $14^3$ (such that the fluid-drawing member $42^3$ is aligned with the central axis, A-A, when the container closure $14^3$ is attached to the container $12^3$).

The fluid-drawing member $42^3$ may also be defined by a length dimension, $L_{42}^3$. The length dimension $L_{42}^3$ of the fluid-drawing member $42^3$ may be approximately equal to, but slightly greater than a length $L_{18}^3$ of the side wall $18^3$ of the container $12^3$; due to the conically-pitched angle, $\theta$, formed by the inner surface $16_I^3$ of the end wall $16^3$, upon connecting the container closure $14^3$ to the container $12^3$, the distal end $42_D^3$ of the fluid-drawing member $42^3$ may be arranged substantially adjacent to but in a slightly spaced-apart relationship with respect to the inner surface $16_I^3$ of the end wall $16^3$ defined by the central portion $16^3$ of the end wall $16^3$ that is aligned with the central axis, A-A. By selectively defining the length relationship of the length dimensions $L_{42}^3$, $L_{18}^3$ of the fluid-drawing member $42^3$ and the side wall $18^3$, and, in addition, the axial alignment of the fluid-drawing member $42^3$ with respect to the central portion $28_C^3$ of the end wall $28^3$ of the container closure $14^3$, the fluid drawing member $42^3$ is selectively positioned relative to the container $12^3$ in order to draw a remainder of fluid, F, contained within the fluid reservoir $24^3$ when all of the fluid, F, contained within the container $12^3$ is nearly depleted as seen in FIG. 8E.

The container assembly $10^3$ also includes a disk-shaped member $46^3$ that is disposed upon and supported by one or both of the second shoulder surface $38^3$ and the axial wall surface $40^3$ defined by the distal end of the syringe-engaging portion $34^3$. The disk-shaped member $46^3$ may be secured to one or more of the second shoulder surface $38^3$ and the axial wall surface $40^3$ in any desirable fashion (e.g., with an adhesive or a friction-fit connection). The disk-shaped member $46^3$ may be formed from any desirable material including, for example, foam, rubber or the like. The disk-shaped member $46^3$ inhibits contaminates from surrounding atmosphere, A, from entering the fluid-flow passage $44^3$ and into the fluid reservoir $24^3$.

The disk-shaped member $46^3$ may include a slit $48^3$ that is aligned with an axial center of both of the container closure $14^3$ and the disk-shaped member $46^3$. The slit $48^3$ selectively permits fluid communication between surrounding atmosphere, A, and the fluid-flow passage $44^3$ that is fluidly-connected to the fluid reservoir $24^3$. Access to (i.e., fluid communication) with the fluid-flow passage $44^3$ from a device (e.g., the syringe, S) that is located in surrounding atmosphere, A, is permitted when a distal tip, $S_{DT}$, of the syringe, S, axially penetrates the slit $48^3$ as seen in FIG. 8D.

Figure 8B:
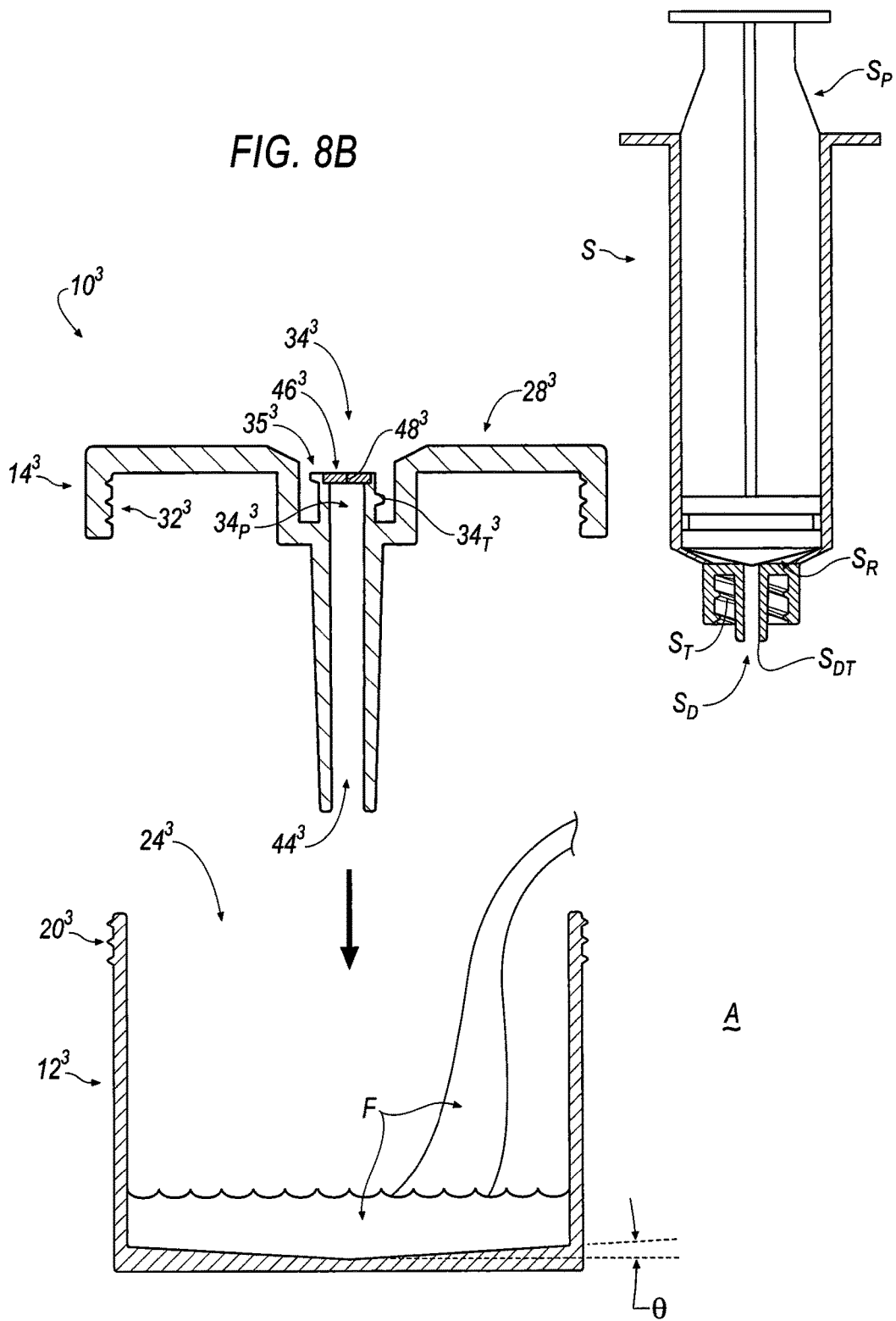
FIGS. 8B-8E illustrate a method of utilizing the container assembly of FIG. 8A.
Figure 8C:
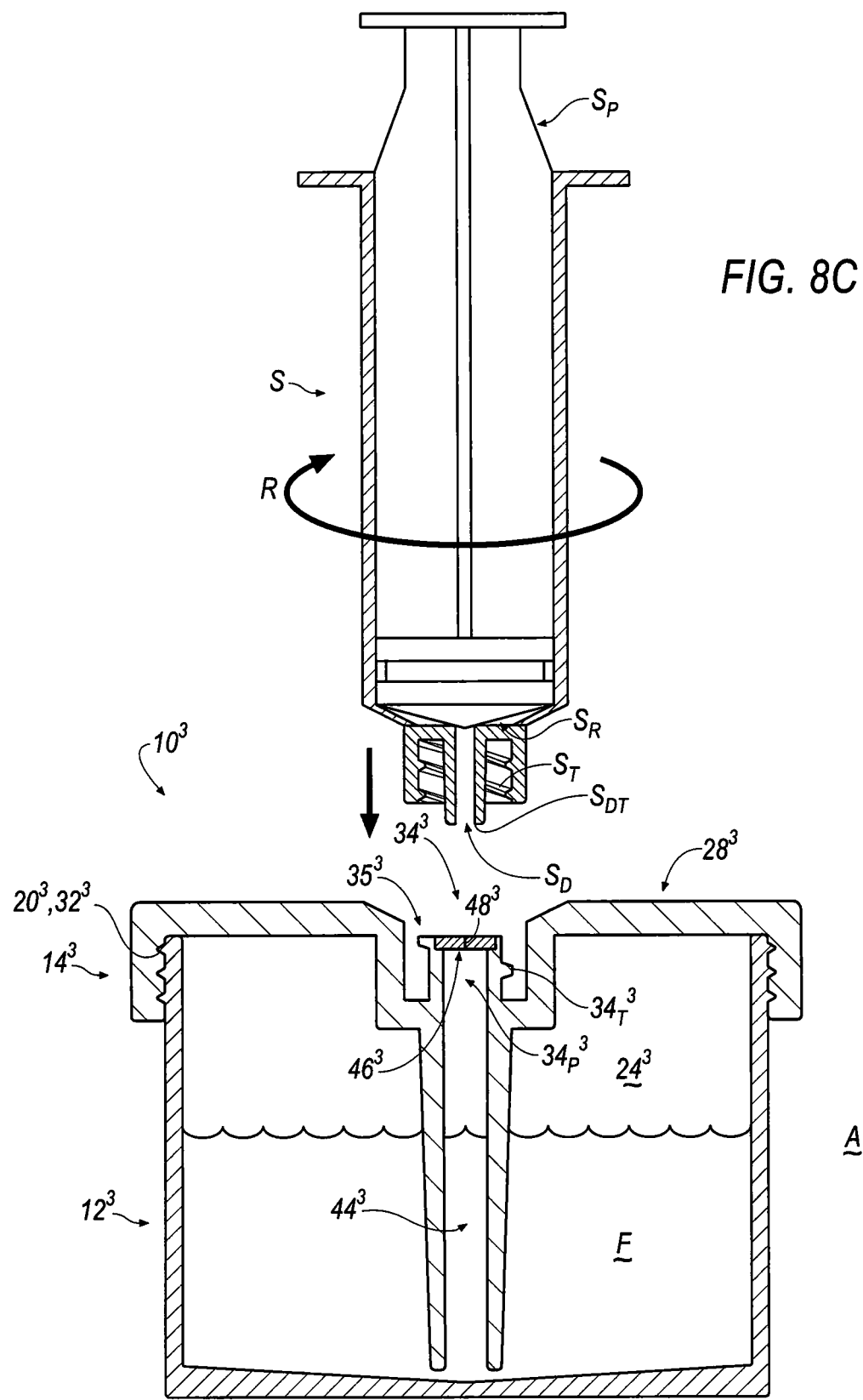
Figure 8D:
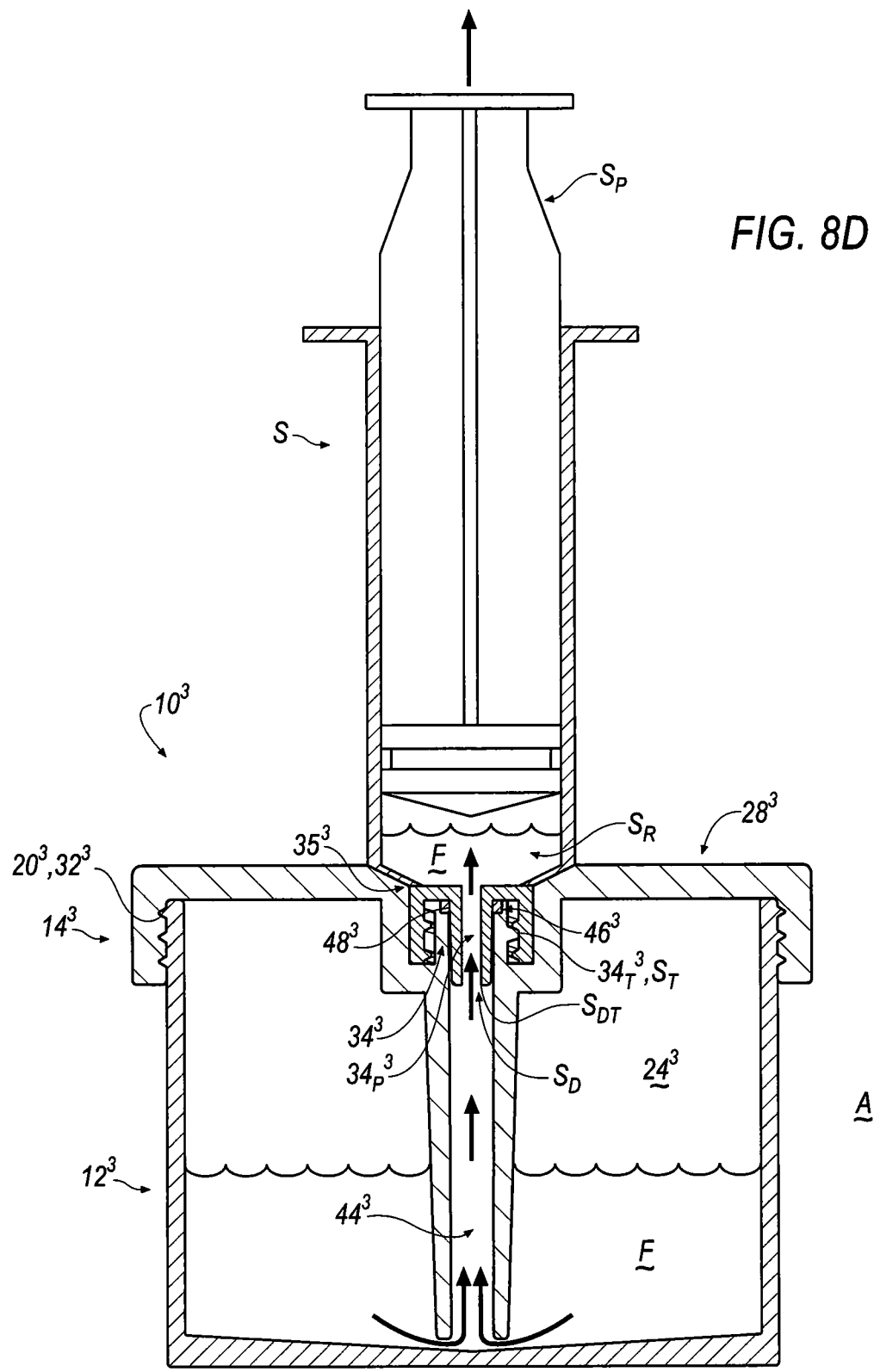
Figure 8E:
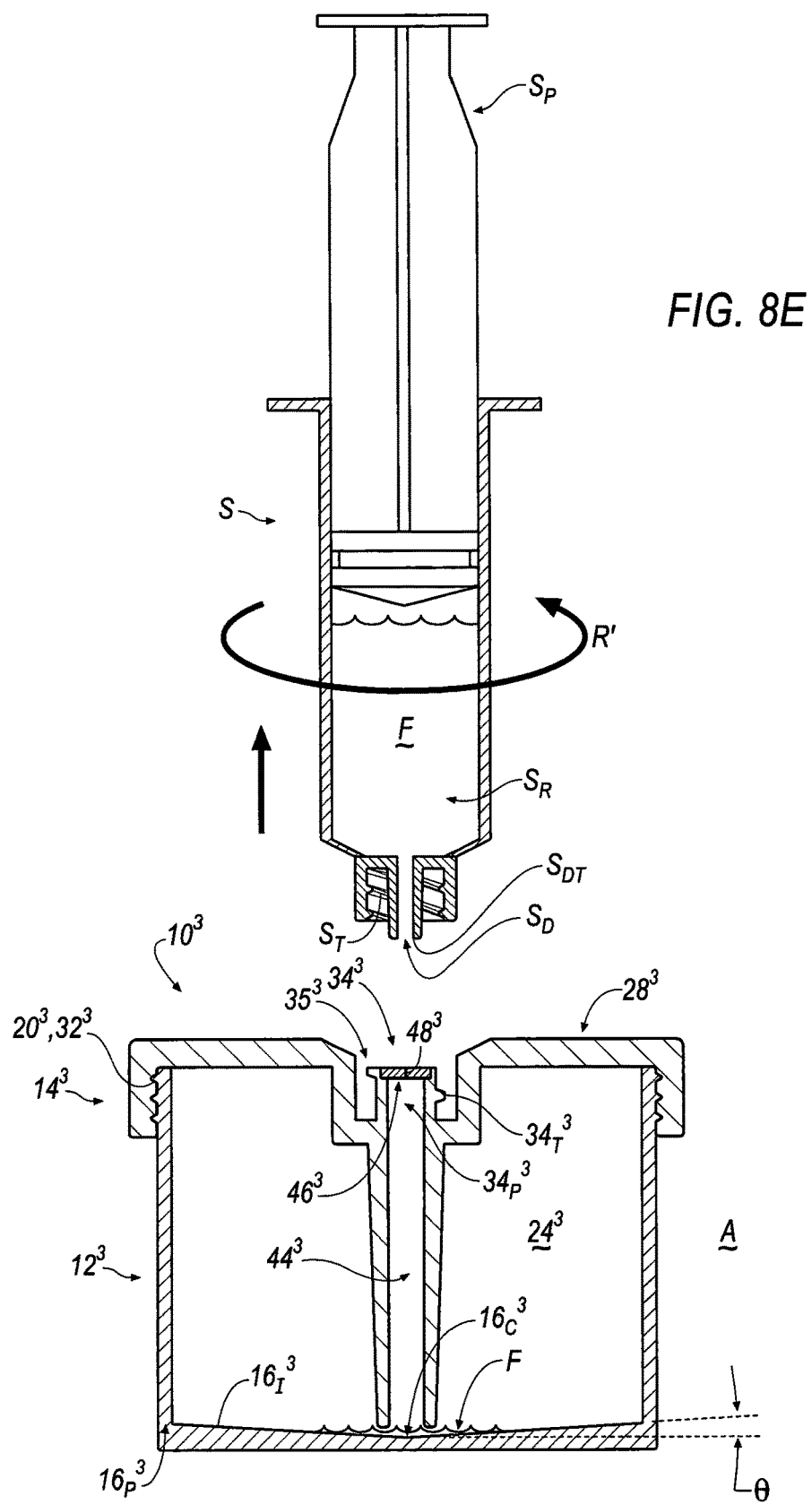

Referring to FIGS. 8B-8E, a method for utilizing the container assembly $10^3$ is described. Referring firstly to FIG. 8B, the container closure $14^3$ is shown disengaged from the container $12^3$, and, a fluid, F, is disposed within the fluid reservoir $28^3$. Referring to FIG. 8C, the container closure $14^3$ is connected (e.g., threadingly-connected) to the container $12^3$ by, for example, the cooperating threaded surfaces $20^3$, $32^3$ of the container $12^3$ and container closure $14^3$ thereby fluidly sealing the fluid reservoir $28^3$ from surrounding atmosphere, A. Once the container closure $14^3$ is secured to the container $12^3$, the distal end, $S_D$, of the syringe, S, may be aligned with and arranged over the syringe-engaging portion $34^3$ extending axially away from the central portion $28_C^3$ of the end wall $28^3$ of the container closure $14^3$. The syringe, S, may be connected to the syringe-engaging portion $34^3$ by axially rotating, R, the syringe, S, relative to the syringe-engaging portion $34^3$ such that the inner threaded surface portion, $S_T$, of the syringe, S, threadingly-engages the outer threaded surface $34_T^3$ of the syringe-engaging portion $34^3$.

Referring to FIG. 8D, the distal end, $S_D$, of the syringe, S, is threadingly-connected to the syringe-engaging portion $34^3$ such that the distal tip, $S_{DT}$, of the syringe, S, axially penetrates the slit $48^3$ to thereby arrange a fluid reservoir, $S_R$, of the syringe, S, in fluid communication with the fluid-flow passage $44^3$ that is in fluid communication with the fluid, F, contained by the fluid reservoir $28^3$. Once the fluid reservoir, $S_R$, of the syringe, S, is in fluid communication with the fluid-flow passage $44^3$ as described above, a user may axially manipulate a plunger, $S_P$, of the syringe, S, in order to draw the fluid, F, from the fluid reservoir $28^3$ into the fluid reservoir, $S_R$, of the syringe, S, by way of the fluid-flow passage $44^3$.

Referring to FIG. 8E, once the user has withdrawn a desired amount of fluid, F, from the fluid reservoir $28^3$ and into the fluid reservoir, $S_R$, of the syringe, S, the user may axially rotate, R', the syringe, S, in a direction opposite that of the rotational direction, R, in order to axially disconnect the distal end, $S_D$, of the syringe, S, from the syringe-engaging portion $34^3$. Once the distal end, $S_D$, of the syringe, S, is withdrawn from the syringe-engaging portion $34^3$, the distal tip, $S_{DT}$, of the syringe, S, no longer penetrates the slit $48^3$, and, as a result, the disk-shaped member $46^3$ may return to its pre-penetrated state, thereby fluidly sealing the fluid-flow passage $44$ and the fluid reservoir $28^3$ from surrounding atmosphere, A.

As seen in FIG. 8E, the conically-pitched angle, θ, formed by the inner surface $16_I^3$ of the end wall $16^3$, directs a remainder of non-withdrawn fluid, F, disposed upon the inner surface $16_I^3$ of the end wall $16^3$ (with the assistance of gravity) away from the outer perimeter portion $16_P^3$ of the end wall $16^3$ and toward the central portion $16^3$ of the end wall $16^3$; as a result, the remainder of the non-withdrawn fluid, F, may be arranged/aligned with the fluid-flow passage $44^3$ for subsequent withdrawal from the container $12^3$.

Figure 9:
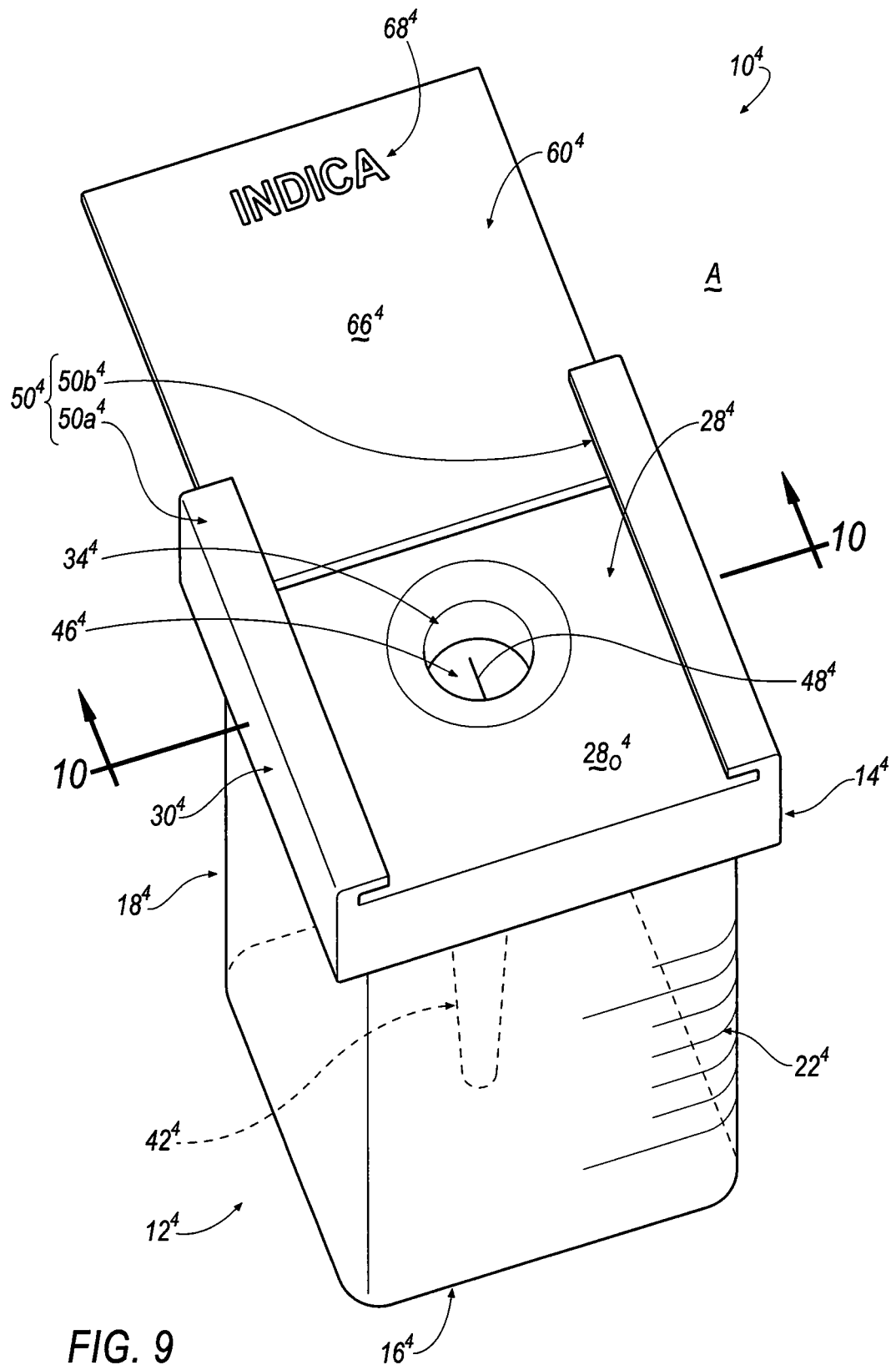
FIG. 9 illustrates a perspective view of a container assembly in accordance with an exemplary embodiment of the invention.

An exemplary container assembly is shown generally at $10^4$ in FIG. 9. The container assembly $10^4$ generally includes a container $12^4$ and a container closure $14^4$.

Figure 10A:
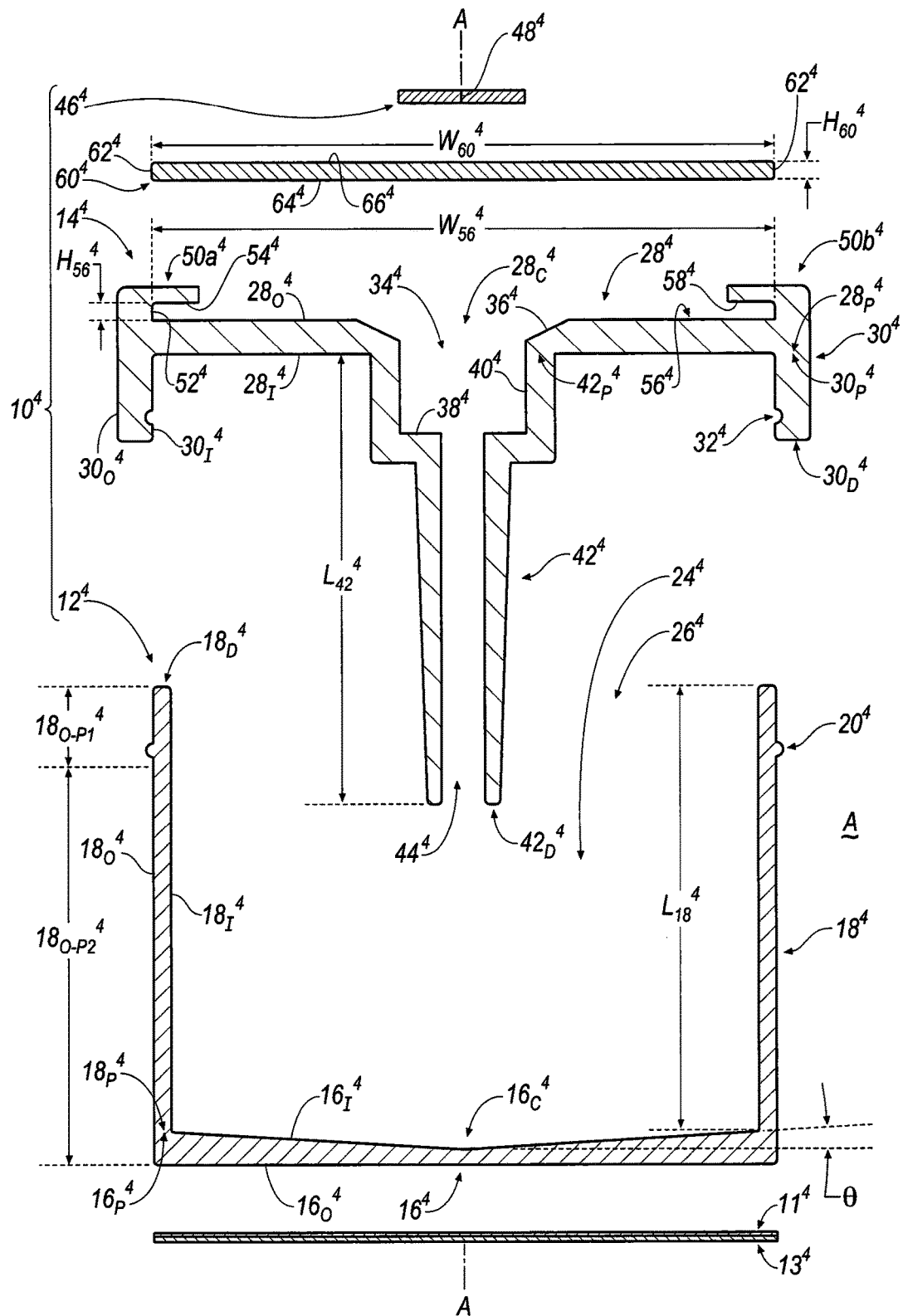
FIG. 10A is an exploded cross-sectional view of the container assembly according to line 10-10 of FIG. 9.

Referring to FIG. 10A, the container $12^4$ includes an end wall $16^4$ and a side wall $18^4$. The end wall $16^4$ and the side wall $18^4$ may include any desirable material or geometry. In some instances, the container $12^4$ may include a clear plastic or glass material; in some implementations, the material may include a coating (e.g., an antimicrobial coating). In some examples as seen in FIG. 9, the end wall $16^4$ may define a square- or recetangular-shaped member and the side wall $18^4$ may define four substantially flat panel portions; collectively, the end wall $16^4$ and the side wall $18^4$ define a cube-shaped body.

As seen in FIG. 10A, the end wall $16^4$ includes a central portion $16_C^4$ and an outer perimeter portion $16_P^4$. The side wall $18^4$ includes a proximal end $18_P^4$ and a distal end $18_D^4$. The proximal end $18_P^4$ of the side wall $18^4$ is connected to and extends away from the outer perimeter portion $16_P^4$ of the end wall $16^4$.

The end wall $16^4$ includes an inner surface $16_I^4$ and an outer surface $16_O^4$. The inner surface $16_I^4$ of the end wall $16^4$ may be conically-pitched according to an angle, θ, to define the central portion $16_C^4$ of the end wall $16^4$ the container $12^4$ to be a low point of the inner surface $16_I^4$ of the end wall $164$ of the container $12^4$. In some instances, the angle may be approximately equal to 15°. In some examples, the container $12^4$ may optionally include an adhesive $11^4$ applied over the outer surface $16_O^4$ of the end wall $16^4$. In some instances, an optional release paper $13^4$ may be applied over the adhesive $11^4$. Prior to disposing the container $12^4$ upon a support surface, a user may remove the release paper (thereby exposing the adhesive $11^4$ applied over the outer surface $16_O^4$ of the end wall $16^4$); the exposed adhesive $13^4$ may assist in the prevention of movement of the container $12^4$ upon the support surface once the outer surface $16_O^4$ of the end wall $164$ is arranged upon the support surface.

The side wall $18^4$ includes an inner surface $18_I^4$ and an outer surface $18_O^4$. A first portion $18_{O-P1}^4$ of the outer surface $18_O^4$ of the side wall $18^4$ may define a first portion of a snap-fit connection (such as, for example, a projection $20^4$ of the container $12^4$). A second portion $18_{O-P2}^4$ of the outer surface $18_O^4$ of the side wall $18^4$ may include printed indicia $22^4$ (as seen in FIG. 9) defining, for example, an amount of fluid disposed within the container $12^4$. As will be described in the following disclosure, the portion of the snap-fit connection $20^4$ of the container $12^4$ may cooperate with a second portion of a snap-fit connection (such as, e.g., a recess $32^4$) of the container closure $14^4$ for selectively attaching the container closure $14^4$ to the container $12^4$.

The container $12^4$ forms a fluid reservoir $28^3$ that is defined by the inner surface $16_I^4$, $18_I^4$ of both of the end wall $16^4$ and the side wall $18^4$. Access to the fluid reservoir $28^4$ is permitted by an opening $28^3$ formed by the distal end $18_D{}^4$ of the side wall $18^4$.

Referring to FIG. 10A, the container closure $14^4$ includes an end wall $28^4$ and a side wall $30^4$. The end wall $28^3$ and the side wall $30^4$ may include any desirable material or geometry. In some instances, the container closure $14^4$ may include an opaque plastic material; in some implementations, the material may include a coating (e.g., an antimicrobial coating). In some examples as seen in FIG. 9, the end wall $28^3$ may define a square- or rectangular-shaped member and the side wall $30^4$ may define four substantially flat panel portions; collectively, the end wall $28^3$ and the side wall $30^4$ define a cube-shaped body.

As seen in FIG. 10A, the end wall $28^3$ includes a central portion $28_C{}^4$ and an outer perimeter portion $28_P{}^4$. The side wall $30^4$ includes a proximal end $30_P{}^4$ and a distal end $30_D{}^4$. The proximal end $30_P{}^4$ of the side wall $30^4$ is connected to and extends away from the outer perimeter portion $28_P{}^4$ of the end wall $28^4$. The central portion $28_C{}^4$ of the end wall $28^4$ of the container closure $14^4$ and the central portion $16_C{}^4$ of the end wall $16^4$ of the container $12^4$ may be aligned with a central axis, A-A, extending through the container assembly $10^4$.

The end wall $28^4$ includes an inner surface $28_I{}^4$ and an outer surface $28_O{}^4$. The side wall $30^4$ includes an inner surface $30_I{}^4$ and an outer surface $30_O{}^4$. The inner surface $30_I{}^4$ of the side wall $30^4$ may define the second portion of a snap-fit connection (such as, e.g., a recess $32^4$) of the container closure $14^4$. As will be described in the following disclosure, the recess $32^4$ of the container closure $14^4$ may cooperate with the projection $20^4$ of the container $12^4$ for selectively attaching the container closure $14^4$ to the container $12^4$.

The outer surface $28_O{}^4$ of the end wall $28^4$ of the container closure $14^4$ generally defines a syringe-engaging portion, such as, for example, a syringe-receiving bore $34^4$. The syringe-receiving bore $34^4$ is formed in the central portion $28_C{}^4$ of the end wall $28^3$ of the container closure $14^4$. An axial center of the syringe-receiving bore $34^4$ is aligned with the central axis, A-A.

The syringe-receiving bore $34^4$ is defined by portions $36^4$, $38^4$, $40^4$ of the outer surface $28_O{}^4$ of the end wall $28^4$ of the container closure $14^4$ and sized for receiving a distal end, $S_D$, of a syringe, S. The portions $36^4$, $38^4$, $40^4$ of the outer surface $28_O{}^4$ of the end wall $28^4$ of the container closure $14^4$ includes: a first shoulder surface $36^4$, a second shoulder surface $38^4$ and an axial wall surface $40^4$ extending substantially perpendicularly from the second shoulder surface $38^4$ and connects the first shoulder surface $36^4$ to the second shoulder surface $38^4$. The first shoulder surface $36^4$ may be tapered in order to conform to a tapered outer wall surface portion of the distal end, $S_D$, of the syringe, S.

The container closure $14^4$ also includes a fluid-drawing member $42^4$ that extends axially away from and is integral with the inner surface $28_I{}^4$ of the end wall $28^4$ of the container closure $14^4$. The fluid-drawing member $42^4$ includes a proximal end $42_P{}^4$ and a distal end $42_D{}^4$. A fluid-flow passage $44^4$ extends through the fluid-drawing member $42^4$ between the proximal end $42_P{}^4$ and the distal end $42_D{}^4$. The fluid-flow passage $44^4$ is aligned with an axial center of the fluid-drawing member $42^4$. When the container closure $14^4$ is connected to the container $12^4$, the fluid-flow passage $44^4$ is in fluid communication with the fluid reservoir $28^4$ defined by the container $12^4$.

The proximal end $42_P{}^4$ of the fluid-drawing member $42^4$ is connected to and extends away from the inner surface $28_I{}^4$ of the end wall $28^4$ of the container closure $14^4$. In some instances, the fluid-drawing member $42^4$ may extend away from the inner surface $28_I{}^4$ at the central portion $28_C{}^4$ of the end wall $28^4$ of the container closure $14^4$ (such that the fluid-drawing member $42^4$ is aligned with the central axis, A-A, when the container closure $14^4$ is attached to the container $12^4$).

The fluid-drawing member $42^4$ may also be defined by a length dimension, $L_{42}{}^4$. A portion of the syringe-receiving bore $34^4$ may extend into a portion of the length, $L_{42}{}^4$, defining the fluid-drawing member $42^4$. The length dimension $L_{42}{}^4$ of the fluid-drawing member $42^4$ may be approximately equal to, but slightly greater than a length $L_{18}{}^4$ of the side wall $18^4$ of the container $12^4$; due to the conically-pitched angle, θ, formed by the inner surface $16_I{}^4$ of the end wall $16^4$, upon connecting the container closure $14^4$ to the container $12^4$, the distal end $42_D{}^4$ of the fluid-drawing member $42^4$ may be arranged substantially adjacent to but in a slightly spaced-apart relationship with respect to the inner surface $16_I{}^4$ of the end wall $16^4$ defined by the central portion $16^4$ of the end wall $16^4$ that is aligned with the central axis, A-A. By selectively defining the length relationship of the length dimensions $L_{42}{}^4$, $L_{18}{}^4$ of the fluid-drawing member $42^4$ and the side wall $18^4$, and, in addition, the axial alignment of the fluid-drawing member $42^4$ with respect to the central portion $28_C{}^4$ of the end wall $28^4$ of the container closure $14^4$, the fluid drawing member $42^4$ is selectively positioned relative to the container $12^4$ in order to draw a remainder of fluid, F, contained within the fluid reservoir $24^4$ when all of the fluid, F, contained within the container $12^4$ is nearly depleted as seen in FIG. 10E.

The container assembly $10^4$ also includes a disk-shaped member $4e$ that is disposed upon and supported by one or both of the second shoulder surface $3e$ and the axial wall surface $40^4$ defining the syringe-receiving bore $34^4$. The disk-shaped member $46^4$ may be secured to one or more of the second shoulder surface $38^4$ and the axial wall surface $40^4$ in any desirable fashion (e.g., with an adhesive or a friction-fit connection). The disk-shaped member $46^4$ may be formed from any desirable material including, for example, foam, rubber or the like.

The disk-shaped member $46^4$ selectively prevents fluid communication between the syringe-receiving bore $34^4$ and the fluid-flow passage $44^4$. The disk-shaped member $46^4$ also inhibits contaminates from surrounding atmosphere, A, from entering the fluid-flow passage $44^4$ and into the fluid reservoir $24^4$.

The disk-shaped member $46^4$ may include a slit $4e$ that is aligned with an axial center of both of the container closure $14^4$ and the disk-shaped member $46^4$. The slit $48^4$ permits selective fluid communication with the fluid-flow passage $44^4$ and the fluid reservoir $28^4$ from surrounding atmosphere, A. Access to (i.e., fluid communication) with the fluid-flow passage $44^4$ from a device (e.g., the syringe, S) that is located in surrounding atmosphere, A, is permitted when a distal tip, $S_{DT}$, of the syringe, S, axially penetrates the slit $48^4$ as seen in FIG. 10D.

The outer surface $28_O{}^4$ of the end wall $28^4$ of the container closure $14^4$ further includes a pair of spaced-apart cover-retaining members $50^4$ (see, e.g., FIG. 9) including a first cover-retaining member $50a^4$ (see, e.g., FIG. 10A) and a second cover-retaining member $50b^4$ (see, e.g., FIG. 10A). Each cover-retaining member $50a^4$, $50b^4$ of the pair of cover-retaining members $50^4$ may include any desirable cross-sectional shape or geometry such as, for example, an L-shaped cross-section.

Each cover-retaining member $50a^4$, $50b^4$ of the pair of cover-retaining members $50^4$ includes an axial surface portion $52^4$ and a radial surface portion $54^4$. The axial surface portion $52^4$ of each cover-retaining member $50a^4$, $50b^4$ are spaced apart to define a gap $56^4$ having a width dimension $W_{56}^4$. The radial surface portion $54^4$ of each cover-retaining member $50a^4$, $50b^4$ is spaced apart from the outer surface $28_O^4$ of the end wall $28^4$ of the container closure $14^4$ to define a gap $55^4$ having a height dimension $H_{58}^4$.

The container closure $14^4$ also includes a cover member $60^4$ that is selectively disposed upon and supported by outer surface $28_O^4$ of the end wall $28^4$ of the container closure $14^4$. Referring to FIG. 9, the cover member $60^4$ is partially selectively disposed upon and supported by outer surface $28_O^4$ of the end wall $28^4$ of the container closure $14^4$; however, when the cover member $60^4$ that is selectively disposed upon and supported by outer surface $28_O^4$ of the end wall $28^4$ of the container closure $14^4$ such that the cover member $60^4$ is disposed over the syringe-receiving bore $34^4$, the cover member $60^4$ isolates the syringe-receiving bore $34^4$ from surrounding atmosphere, A, thereby mitigating contaminates from intruding into the syringe-receiving bore $34^4$.

Referring to FIG. 10A, the cover member $60^4$ includes a width dimension $W_{60}^4$ extending between opposite side surfaces $62^4$ of the cover member $60^4$. The cover member $60^4$ also includes a height dimension $H_{60}^4$ extending between a lower surface $6e$ and an upper surface $6e$ of the cover member $60^4$. The cover member $60^4$ may be made from any desirable material such as, for example, a plastic material; in some implementations, the material may include a coating (e.g., an antimicrobial coating). The upper surface $66^4$ of the cover member $60^4$ may also include printed or hand-written indicia $68^4$ (as seen in FIG. 9) that may, for example, inform a user what type or kind of fluid, F, is contained within the container $12^4$.

The width dimension $W_{60}^4$ of the cover member $60^4$ may be approximately equal to but slightly less than the width dimension $W_{56}^4$ of the gap $56^4$ extending between the cover-retaining members $50a^4$, $50b^4$. The height dimension $H_{60}^4$ of the cover member $60^4$ may be approximately equal to but slightly less than the height dimension $H_{56}^4$ of the gap $56^4$ extending between radial surface portion $54^4$ of each cover-retaining member $50a^4$, $50b^4$ and the outer surface $28_O^4$ of the end wall $28^4$ of the container closure $14^4$. As a result of the proportions of the width and height dimensions, $W_{56}^4$, $H_{56}^4$, of the gap $56^4$ and the width and height dimensions, $W_{60}^4$, $H_{60}^4$, of the cover member $60^4$, the cover member $60^4$ may be selectively retained to the container closure $14^4$ by the pair of cover-retaining members $50^4$.

Figure 10B:
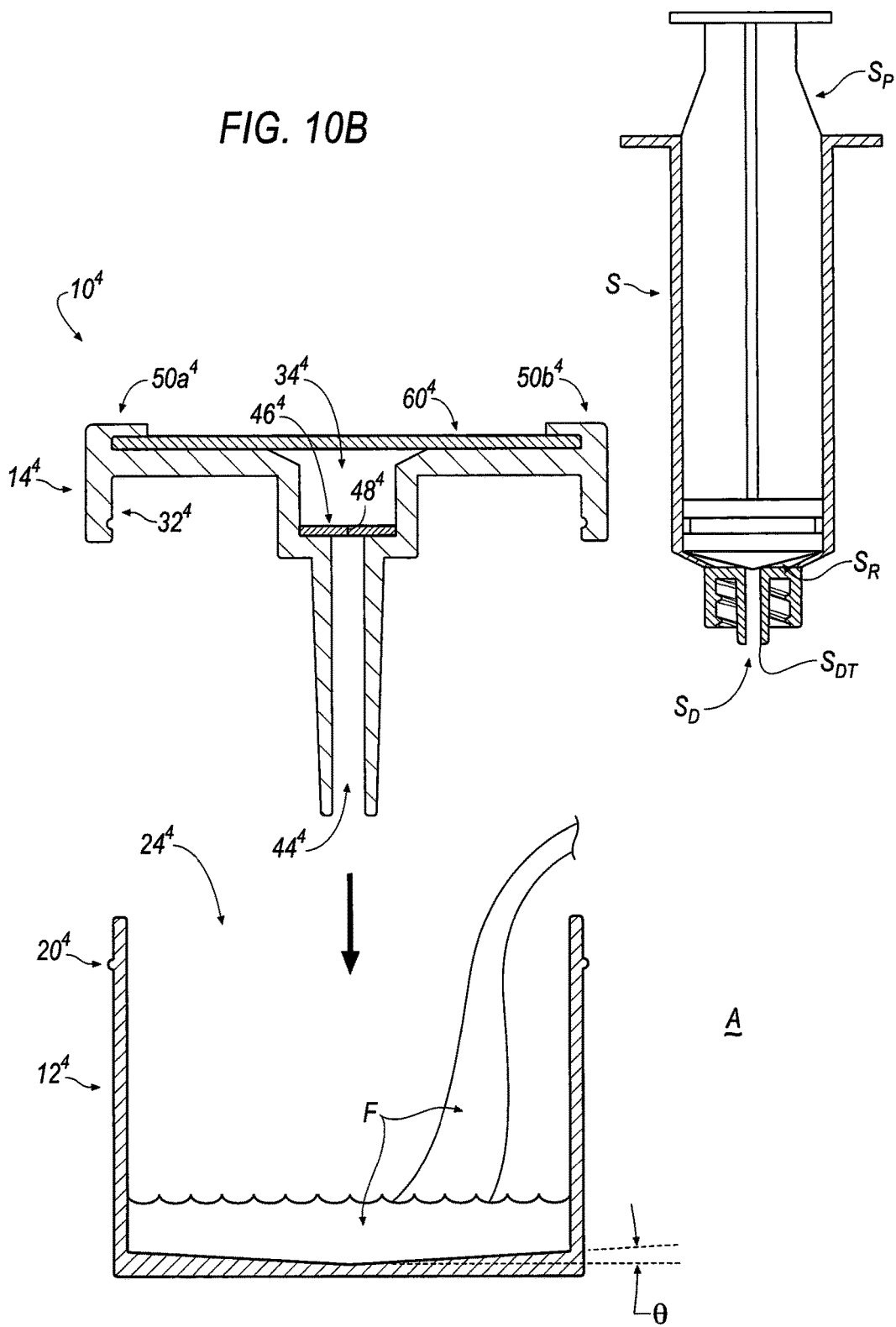
FIGS. 10B-10E illustrate a method of utilizing the container assembly of FIG. 10A.
Figure 10C:
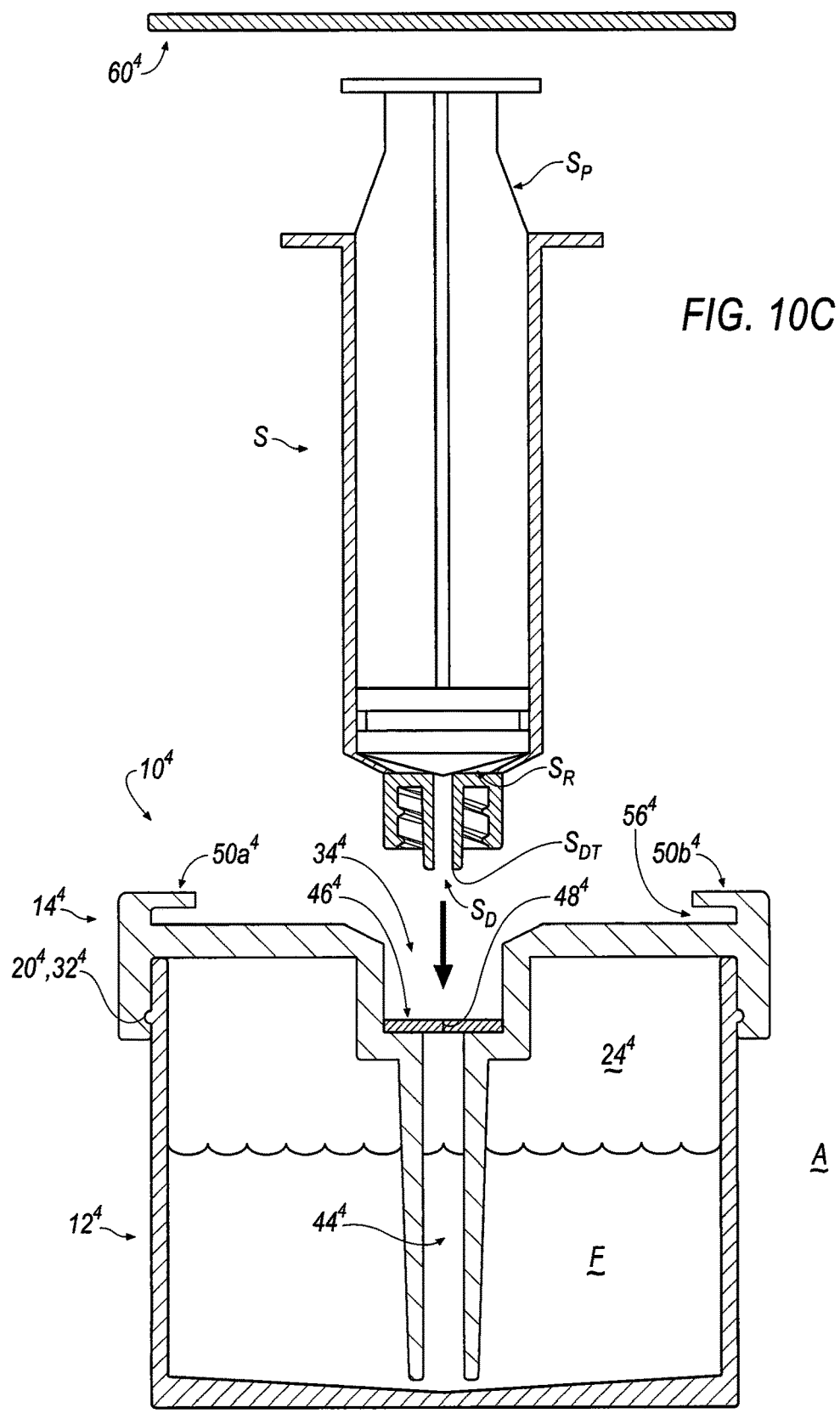
Figure 10D:
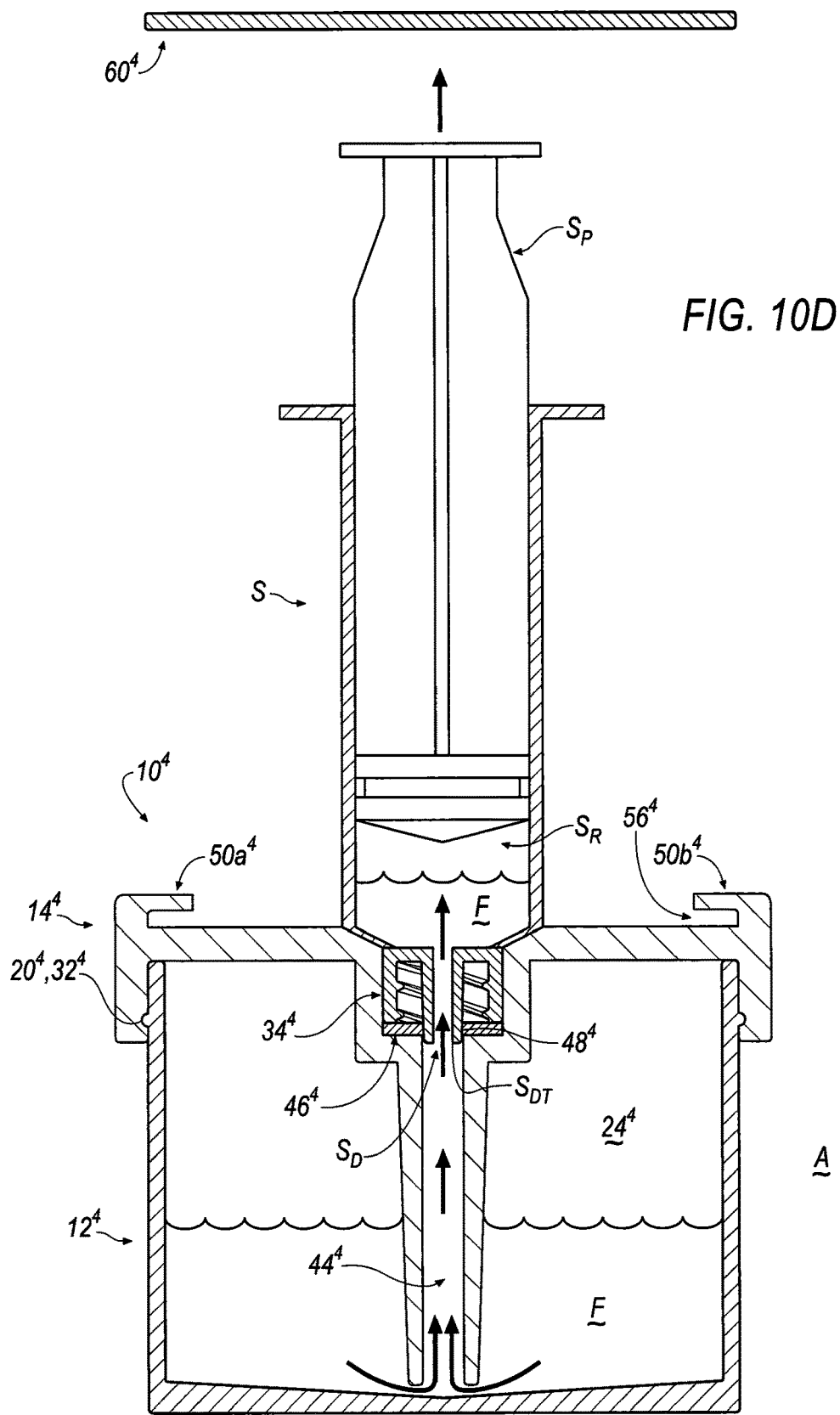
Figure 10E:
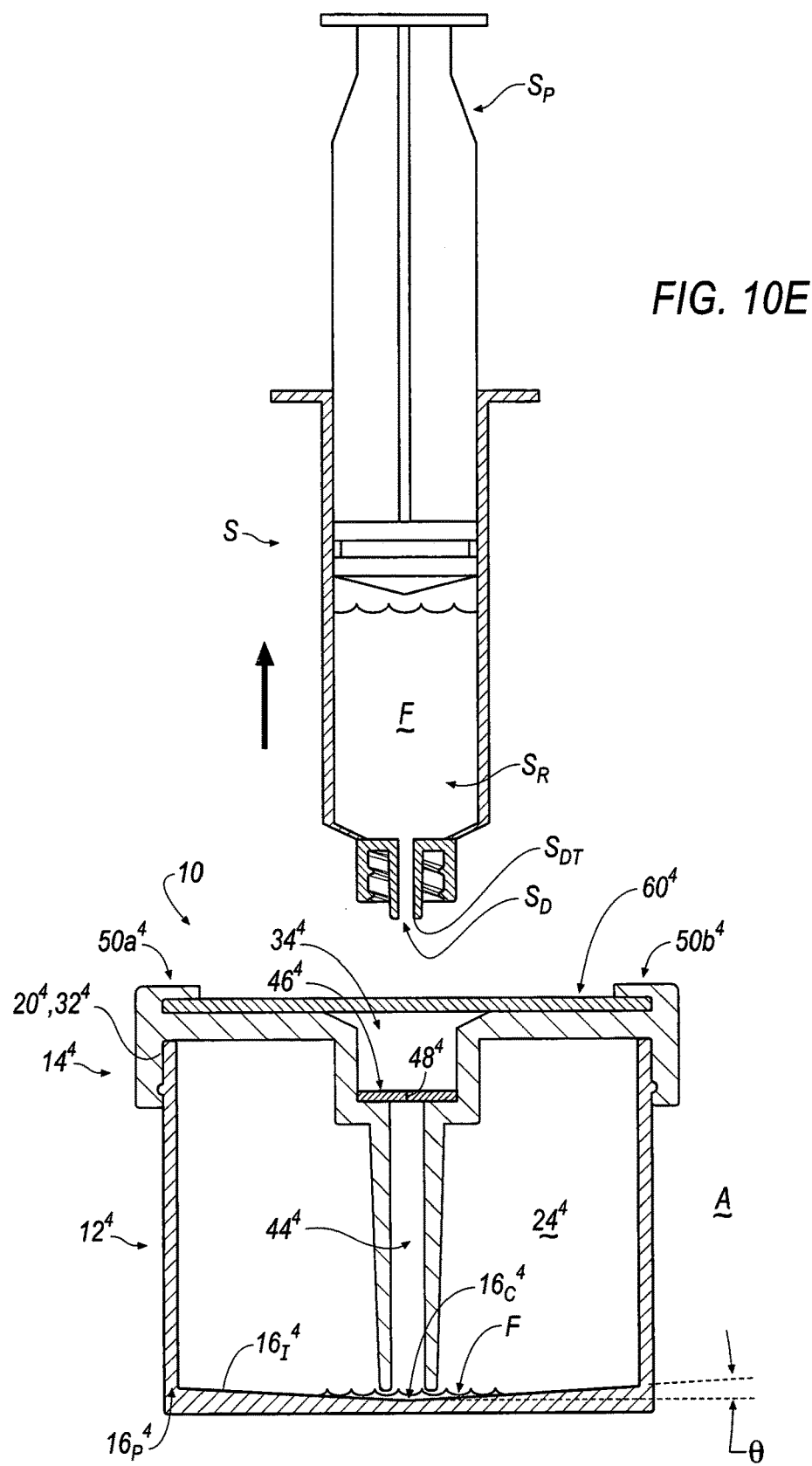

Referring to FIGS. 10B-10G, a method for utilizing the container assembly $10^4$ is described. Referring firstly to FIG. 10B, the container closure $14^4$ (which also includes the cover member $60^4$ selectively-attached thereto) is shown disengaged from the container $12^4$, and, a fluid, F, is disposed within the fluid reservoir $24^4$. As seen in FIG. 10C, the cover member $60^4$ may be selectively removed from the container closure $14^4$ by sliding the cover member $60^4$ out of the gap $56^4$ that is formed by the pair of cover-retaining members $50^4$.

Referring to FIG. 10C, the container closure $14^4$ is snap-fit-connected to the container $12^4$ by the cooperating projection $20^4$ and recess $32^4$ of the container $12^4$ and container closure $14^4$ thereby fluidly sealing the fluid reservoir $24^4$ from surrounding atmosphere, A. Once the container closure $14^4$ is secured to the container $12^4$, the distal end, $S_D$, of the syringe, S, may be axially-aligned with and arranged over the syringe-receiving bore $34^4$ formed in the central portion $28_C^4$ of the end wall $28^4$ of the container closure $14^4$.

Referring to FIG. 10D, the distal end, $S_D$, of the syringe, S, is inserted into the syringe-receiving bore $34^4$ and the distal tip, $S_{DT}$, of the syringe, S, axially penetrates the slit $48^4$ to thereby arrange a fluid reservoir, $S_R$, of the syringe, S, is in fluid communication with the fluid-flow passage $44^4$ that is in fluid communication with the fluid, F, contained by the fluid reservoir $24^4$. Once the fluid reservoir, $S_R$, of the syringe, S, is in fluid communication with the fluid-flow passage $44^4$ as described above, a user may axially manipulate a plunger, $S_P$, of the syringe, S, in order to draw the fluid, F, from the fluid reservoir $28^4$ into the fluid reservoir, $S_R$, of the syringe, S, by way of the fluid-flow passage $44^4$.

Referring to FIG. 10E, once the user has withdrawn a desired amount of fluid, F, from the fluid reservoir $24^4$ and into the fluid reservoir, $S_R$, of the syringe, S, the user may remove the distal end, $S_D$, of the syringe, S, from the syringe-receiving bore $34^4$. Once the distal end, $S_D$, of the syringe, S, is withdrawn from the syringe-receiving bore $34^4$, the distal tip, $S_{DT}$, of the syringe, S, no longer penetrates the slit $48^4$, and, as a result, the disk-shaped member $4e$ may return to its pre-penetrated state, thereby fluidly sealing the fluid flow passage $44^4$ and the fluid reservoir $28^4$ from surrounding atmosphere, A. As seen in FIG. 10E, the user may then selectively re-attach the cover member $60^4$ to the container closure $14^4$ by sliding the cover member $60^4$ into the gap $56^4$ that is formed by the pair of cover-retaining members $50^4$.

As seen in FIG. 10E, the conically-pitched angle, θ, formed by the inner surface $16_I^4$ of the end wall $16^4$, directs a remainder of non-withdrawn fluid, F, disposed upon the inner surface $16_I^4$ of the end wall $16^4$ (with the assistance of gravity) away from the outer perimeter portion $16_P^4$ of the end wall $16^4$ and toward the central portion $16_C^4$ of the end wall $16^4$; as a result, the remainder of the non-withdrawn fluid, F, may be arranged/aligned with the fluid-flow passage $44^4$ for subsequent withdrawal from the container $12^4$.

Figure 11:
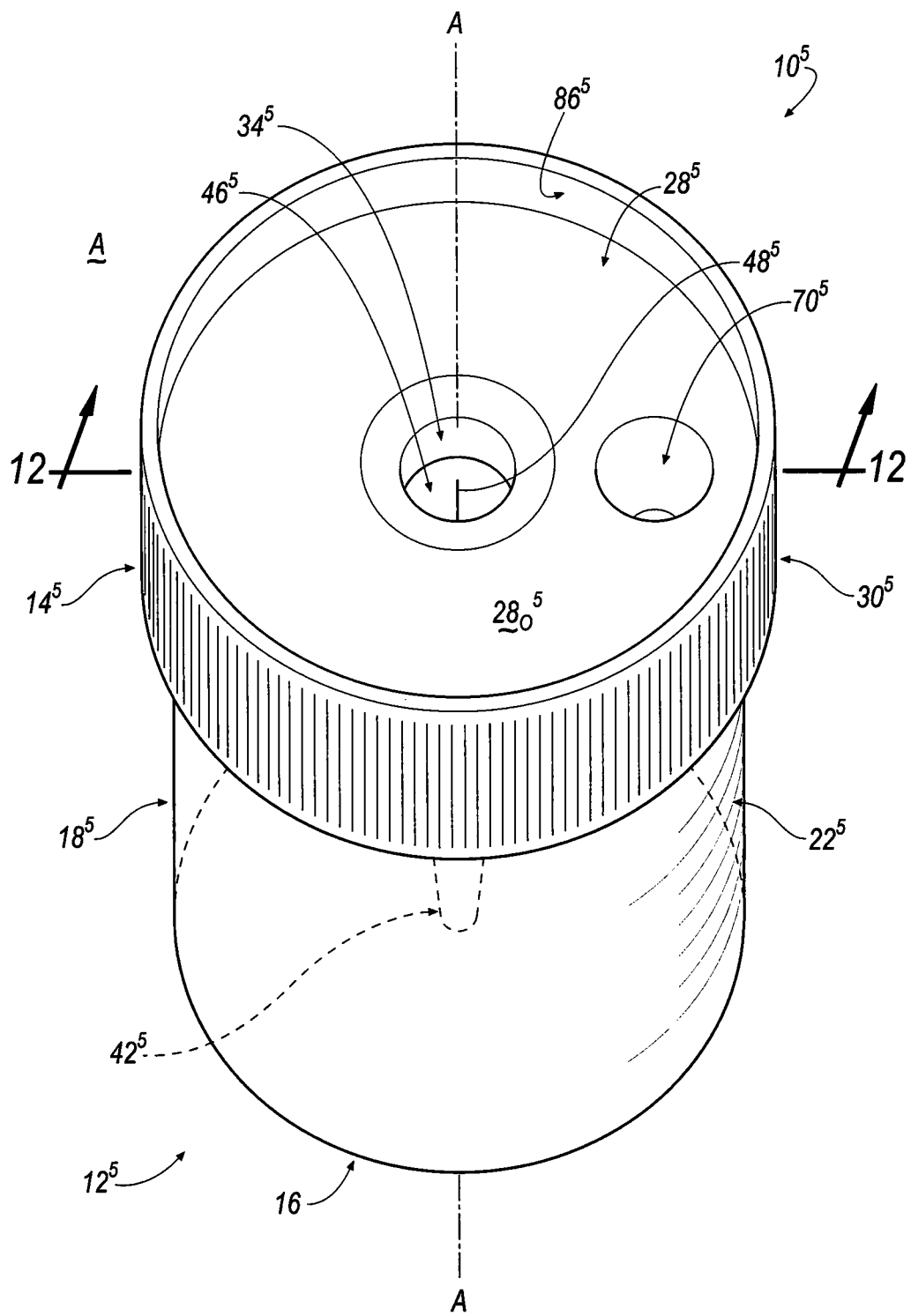
FIG. 11 illustrates a perspective view of a container assembly in accordance with an exemplary embodiment of the invention.

An exemplary container assembly is shown generally at $10^5$ in FIG. 11. The container assembly $10^5$ generally includes a container $12^5$ and a container closure $14^5$.

Figure 12A:
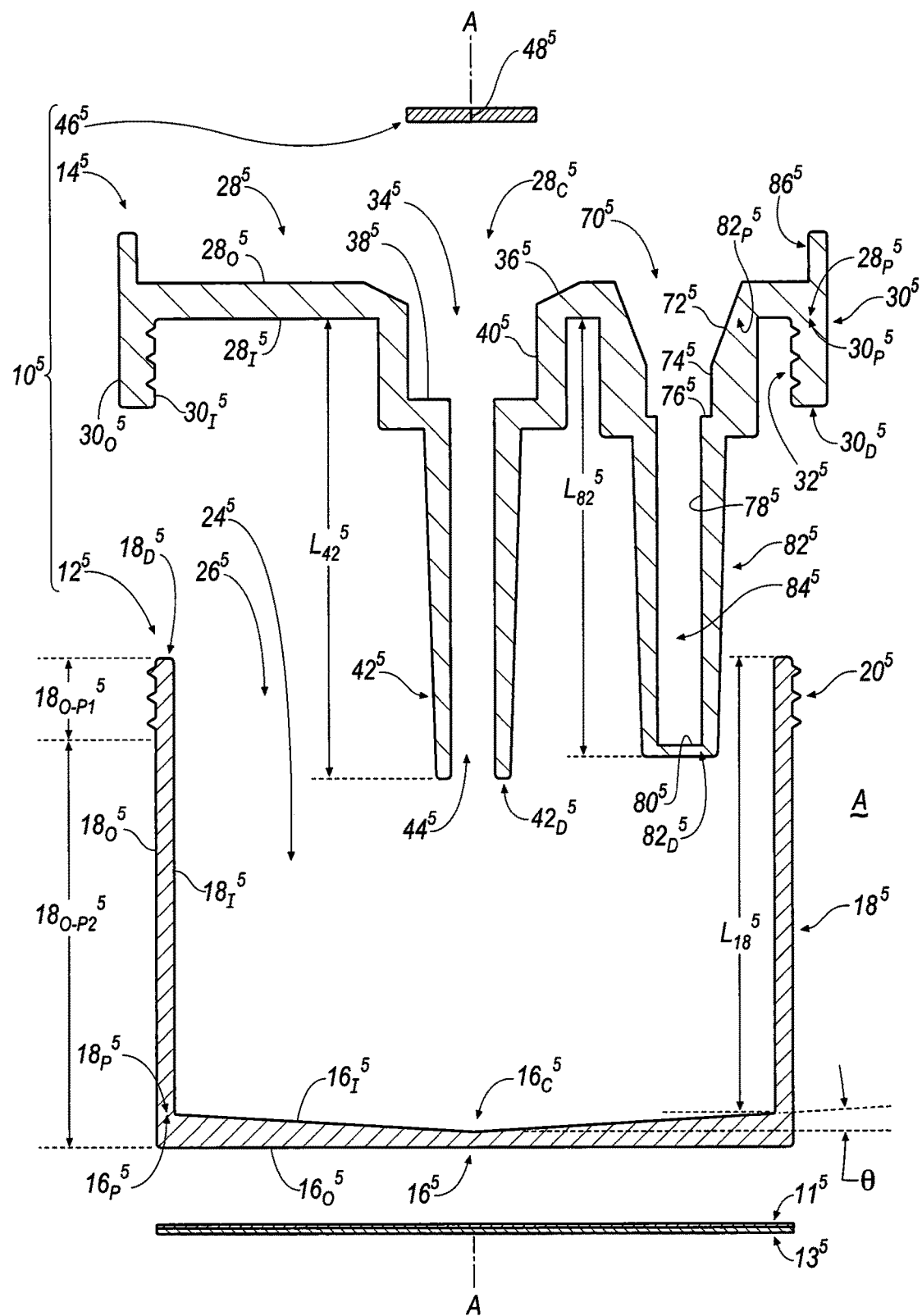
FIG. 12A is an exploded cross-sectional view of the container assembly according to line 12-12 of FIG. 11.

Referring to FIG. 12A, the container $12^5$ includes an end wall $16^5$ and a side wall $18^5$. The end wall $16^5$ and the side wall $18^5$ may include any desirable material or geometry. In some instances, the container $12^5$ may include a clear plastic or glass material; in some implementations, the material may include a coating (e.g., an antimicrobial coating). In some examples as seen in FIG. 11, the end wall $16^5$ may define an annular member and the side wall $18^5$ may define a cylindrical, tube-shaped body.

As seen in FIG. 12A, the end wall $16^5$ includes a central portion $16^5$ and an outer perimeter portion $16_P^5$. The side wall $18^5$ includes a proximal end $18_P^5$ and a distal end $18_D^5$. The proximal end $18_P^5$ of the side wall $18^5$ is connected to and extends away from the outer perimeter portion $16_P^5$ of the end wall $16^5$.

The end wall $16^5$ includes an inner surface $16_I^5$ and an outer surface $16_O^5$. The inner surface $16_I^5$ of the end wall $16^5$ may be conically-pitched according to an angle, θ, to define the central portion $16^5$ of the end wall $16^5$ the container $12^5$ to be a low point of the inner surface $16_I^5$ of the end wall $16^5$ of the container $12^5$. In some instances, the angle may be approximately equal to 15°. In some examples, the container $12^5$ may optionally include an adhesive $11^5$ applied over the outer surface $16_O^5$ of the end wall $16^5$. In some instances, an optional release paper $13^5$ may be applied over the adhesive $11^5$. Prior to disposing the container $12^5$ upon a support surface, a user may remove the release paper (thereby exposing the adhesive $11^5$ applied over the outer surface $16_O^5$ of the end wall $16^5$); the exposed adhesive $13^5$ may assist in the prevention of movement of the container $12^5$ upon the support surface once the outer surface $16_O^5$ of the end wall $16^5$ is arranged upon the support surface.

The side wall $18^5$ includes an inner surface $18_I^5$ and an outer surface $18_O^5$. A first portion $18_{O-P1}^5$ of the outer surface $18_O^5$ of the side wall $18^5$ may define an outer threaded surface $20^5$ of the container $12^5$. A second portion $18_{O-P2}^5$ of the outer surface $18_O^5$ of the side wall $18^5$ may include printed indicia $22^5$ (as seen in FIG. 11) defining, for example, an amount of fluid disposed within the container $12^5$. As will be described in the following disclosure, the outer threaded surface $20^5$ of the container $12^5$ may cooperate with an inner threaded surface $32^5$ of the container closure $14^5$ for selectively attaching the container closure $14^5$ to the container $12^5$.

The container $12^5$ forms a fluid reservoir $24^5$ that is defined by the inner surface $16_I^5$, $18_I^5$ of both of the end wall $16^5$ and the side wall $18^5$. Access to the fluid reservoir $24^5$ is permitted by an opening $26^5$ formed by the distal end $18_D^5$ of the side wall $18^5$.

Referring to FIG. 12A, the container closure $14^5$ includes an end wall $28^5$ and a side wall $30^5$. The end wall $28^5$ and the side wall $30^5$ may include any desirable material or geometry. In some instances, the container closure $14^5$ may include an opaque plastic material; in some implementations, the material may include a coating (e.g., an antimicrobial coating). In some examples as seen in FIG. 11, the end wall $28^5$ may define an annular member and the side wall $30^5$ may define a cylindrical, tube-shaped body.

As seen in FIG. 12A, the end wall $28^5$ includes a central portion $28_C^5$ and an outer perimeter portion $28_P^5$. The side wall $30^5$ includes a proximal end $30_P^5$ and a distal end $30_D^5$. The proximal end $30_P^5$ of the side wall $30^5$ is connected to and extends away from the outer perimeter portion $28_P^5$ of the end wall $28^5$. The central portion $28_C^5$ of the end wall $28^5$ of the container closure $14^5$ and the central portion $16^5$ of the end wall $16^5$ of the container $12^5$ may be aligned with a central axis, A-A, extending through the container assembly $10^5$.

The end wall $28^5$ includes an inner surface $28_I^5$ and an outer surface $28_O^5$. The side wall $30^5$ includes an inner surface $30_I^5$ and an outer surface $30_O^5$. The inner surface $30_I^5$ of the side wall $30^5$ may define an inner threaded surface $32^5$ of the container closure $14^5$. As will be described in the following disclosure, the inner threaded surface $32^5$ of the container closure $14^5$ may cooperate with the outer threaded surface $20^5$ of the container $12^5$ for selectively attaching the container closure $14^5$ to the container $12^5$.

The outer surface $28_O^5$ of the end wall $28^4$ of the container closure $14^5$ generally defines a syringe-engaging portion, such as, for example, a syringe-receiving bore $34^5$. The syringe-receiving bore $34^5$ is formed in the central portion $28_C^5$ of the end wall $28^5$ of the container closure $14^5$. An axial center of the syringe-receiving bore $34^5$ is aligned with the central axis, A-A.

The syringe-receiving bore $34^5$ is defined by portions $36^5$, $38^5$, $40^5$ of the outer surface $28_O^5$ of the end wall $28^5$ of the container closure $14^5$ and sized for receiving a distal end, $S_D$, of a syringe, S. The portions $36^5$, $38^5$, $40^5$ of the outer surface $28_O^5$ of the end wall $28^5$ of the container closure $14^5$ includes: a first shoulder surface $36^5$, a second shoulder surface $3e$ and an axial wall surface $40^5$ extending substantially perpendicularly from the second shoulder surface $38^5$ and connects the first shoulder surface $36^5$ to the second shoulder surface $3e$. The first shoulder surface $36^5$ may be tapered in order to conform to a tapered outer wall surface portion of the distal end, $S_D$, of the syringe, S.

The container closure $14^5$ also includes a fluid-drawing member $42^5$ that extends axially away from and is integral with the inner surface $28_I^5$ of the end wall $28^5$ of the container closure $14^5$. The fluid-drawing member $42^5$ includes a proximal end $42_P^5$ and a distal end $42_D^5$. A fluid-flow passage $44^5$ extends through the fluid-drawing member $42^5$ between the proximal end $42_P^5$ and the distal end $42_D^5$. The fluid-flow passage $44^5$ is aligned with an axial center of the fluid-drawing member $42^5$. When the container closure $14^5$ is connected to the container $12^5$, the fluid-flow passage $44^5$ is in fluid communication with the fluid reservoir $28^4$ defined by the container $12^5$.

The proximal end $42_P^5$ of the fluid-drawing member $42^5$ is connected to and extends away from the inner surface $28_I^5$ of the end wall $28^5$ of the container closure $14^5$. In some instances, the fluid-drawing member $42^5$ may extend away from the inner surface $28_I^5$ at the central portion $28_C^5$ of the end wall $28^5$ of the container closure $14^5$ (such that the fluid-drawing member $42^5$ is aligned with the central axis, A-A, when the container closure $14^5$ is attached to the container $12^5$).

The fluid-drawing member $42^5$ may also be defined by a length dimension, $L_{42}^5$. A portion of the syringe-receiving bore $34^5$ may extend into a portion of the length, $L_{42}^5$, defining the fluid-drawing member $42^5$. The length dimension $L_{42}^5$ of the fluid-drawing member $42^5$ may be approximately equal to, but slightly greater than a length $L_{18}^5$ of the side wall $18^5$ of the container $12^5$; due to the conically-pitched angle, $\theta$, formed by the inner surface $16_I^5$ of the end wall $16^5$, upon connecting the container closure $14^5$ to the container $12^5$, the distal end $42_D^5$ of the fluid-drawing member $42^5$ may be arranged substantially adjacent to but in a slightly spaced-apart relationship with respect to the inner surface $16_I^5$ of the end wall $16^5$ defined by the central portion $16^5$ of the end wall $16^5$ that is aligned with the central axis, A-A. By selectively defining the length relationship of the length dimensions $L_{42}^5$, $L_{18}^5$ of the fluid-drawing member $42^5$ and the side wall $18^5$, and, in addition, the axial alignment of the fluid-drawing member $42^5$ with respect to the central portion $28_C^5$ of the end wall $28^5$ of the container closure $14^5$, the fluid drawing member $42^5$ is selectively positioned relative to the container $12^5$ in order to draw a remainder of fluid, F, contained within the fluid reservoir $24^5$ when all of the fluid, F, contained within the container $12^5$ is nearly depleted as seen in FIG. 12G.

The container assembly $10^5$ also includes a disk-shaped member $46^5$ that is disposed upon and supported by one or both of the second shoulder surface $38^5$ and the axial wall surface $40^5$ defining the syringe-receiving bore $34^5$. The disk-shaped member $46^5$ may be secured to one or more of the second shoulder surface $38^5$ and the axial wall surface $40^5$ in any desirable fashion (e.g., with an adhesive or a friction-fit connection). The disk-shaped member $46^5$ may be formed from any desirable material including, for example, foam, rubber or the like.

The disk-shaped member $46^5$ selectively prevents fluid communication between the syringe-receiving bore $34^5$ and the fluid-flow passage $44^5$. The disk-shaped member $46^5$ also inhibits contaminates from surrounding atmosphere, A, from entering the fluid-flow passage $44^5$ and into the fluid reservoir $24^5$.

The disk-shaped member $46^5$ may include a slit $48^5$ that is aligned with an axial center of both of the container closure $14^5$ and the disk-shaped member $46^5$. The slit $48^5$ permits selective fluid communication with the fluid-flow passage $44^5$ and the fluid reservoir $24^5$ from surrounding atmosphere, A. Access to (i.e., fluid communication) with the fluid-flow passage $44^5$ from a device (e.g., the syringe, S) that is located in surrounding atmosphere, A, is permitted when a distal tip, $S_{DT}$, of the syringe, S, axially penetrates the slit $4e$ as seen in FIG. 12F.

The outer surface $28_O{}^5$ of the end wall $28^4$ of the container closure $14^5$ further defines a needle hub-engaging portion, such as, for example, a needle hub-receiving bore $70^5$. The needle hub-receiving bore $70^5$ is formed in a radially-offset orientation with respect to the central portion $28_C{}^5$ of the end wall $28^5$ of the container closure $14^5$; therefore, an axial center of the needle hub-receiving bore $70^5$ is not aligned with the central axis, A-A.

The needle hub-receiving bore $70^5$ is defined by portions $72^5$, $74^5$, $76^5$, $78^5$, $80^5$ of the outer surface $28_O{}^5$ of the end wall $28^5$ of the container closure $14^5$ and sized for receiving a portion of the distal end, $S_D$, of a syringe, S, and a needle hub, $S_{NH}$, that is attached to the distal end, $S_D$, of a syringe, S, and a needle, $S_N$, extending away from the needle hub, $S_{NH}$. The portions $72^5$, $74^5$, $76^5$, $78^5$, $80^5$ of the outer surface $28_O{}^5$ of the end wall $28^5$ of the container closure $14^5$ includes: a first shoulder surface $72^5$, a first axial wall surface $74^5$, a second shoulder surface $76^5$, a second axial wall surface $78^5$ and a third shoulder surface $80^5$. The first axial wall surface $74^5$ connects the first shoulder surface $72^5$ to the second shoulder surface $76^5$. The second shoulder surface $76^5$ extends substantially perpendicularly from the first axial wall surface $74^5$. The first shoulder surface $72^5$ is tapered and is not substantially perpendicular with respect to the first axial wall surface $74^5$. The second axial wall surface $78^5$ extends substantially perpendicularly from the second shoulder surface $76^5$. The third shoulder surface $80^5$ extends substantially perpendicularly from the second axial wall surface $78^5$.

The first shoulder surface $72^5$ may be sized for receiving a portion of the distal end, $S_D$, of a syringe, S. The first axial wall surface $74^5$ and the second shoulder surface $76^5$ may be sized for receiving a flanged portion, $S_{N-F}$ (see, e.g., FIG. 13), of the needle hub, $S_{NH}$, that is attached to the distal end, $S_D$, of a syringe, S. With reference to FIG. 12D, the first axial wall surface $74^5$ may be configured to receive four flanges (see, e.g., FIG. 13) defining the flanged portion, $S_{N-F}$, of needle hub, $S_{NH}$, and, the second shoulder surface $76^5$ may be sized for receiving a portion of the needle hub, $S_{NH}$. With further reference to FIG. 12D, the second axial wall surface $78^5$ and the third shoulder surface $80^5$ are sized for receiving a needle, $S_N$, extending axially away from the needle hub, $S_{NH}$.

Referring to FIG. 12A, the container closure $14^5$ also includes a needle sheath member $82^5$ that extends axially away from and is integral with the inner surface $28_I{}^5$ of the end wall $28^5$ of the container closure $14^5$. The needle sheath member $82^5$ includes a needle-receiving passage $84^5$ that is in fluid communication with the needle hub-receiving bore $70^5$ and is formed in a radially-offset orientation with respect to the central portion $28_C{}^5$ of the end wall $28^4$ of the container closure $14^5$; therefore, an axial center of the needle hub-receiving bore $70^5$ is not aligned with the central axis, A-A.

The needle sheath member 82 includes a proximal end $82_P{}^5$ and a distal end $82_D{}^5$. The proximal end $82_P{}^5$ of the needle sheath member 82 is connected to and extends away from the inner surface $28_I{}^5$ of the end wall $28^5$ of the container closure $14^5$. The needle-receiving passage $84^5$ extends through a portion of the needle sheath member 82 between the proximal end $82_P{}^5$ and the distal end $82_D{}^5$. As described above, because the needle hub-receiving bore $70^5$ is formed in a radially-offset orientation with respect to the central portion $28_C{}^5$ of the end wall $28^5$ of the container closure $14^5$, and because the needle-receiving passage $84^5$ is in fluid communication with the needle hub-receiving bore $70^5$, the needle-receiving passage $84^5$ is also not aligned with the axial center of the needle hub-receiving bore $70^5$.

The needle sheath member $82$ may also be defined by a length dimension, $L_{82}{}^5$. A portion of the needle hub-receiving bore $70^5$ may extend into a portion of the length, $L_{82}{}^5$, defining the needle sheath member $82^5$. The length dimension $L_{82}{}^5$ of the needle sheath member $82^5$ may be approximately equal to, but slightly less than a length $L_{18}{}^5$ of the side wall $18^5$ of the container $12^5$; due to the conically-pitched angle, $\theta$, formed by the inner surface $16_I{}^5$ of the end wall $16^5$.

The container closure $14^5$ also includes a flange wall $86^5$ that extends axially away from and is integral with the outer surface $28_O{}^5$ of the end wall $28^5$ of the container closure $14^5$. The flange wall $86^5$ may be aligned with and extend away from the proximal end $30_P{}^5$ the side wall $30^5$. Functionally, the flange wall $86^5$ may contain the tip of the needle, $S_N$, in an area about the outer surface $28_O{}^5$ of the end wall $28^5$ should the user fail at initially locating the needle, $S_N$, within the needle hub-receiving bore $70^5$ prior to arranging the needle, $S_N$, within the needle-receiving passage $84^5$.

Figure 12B:
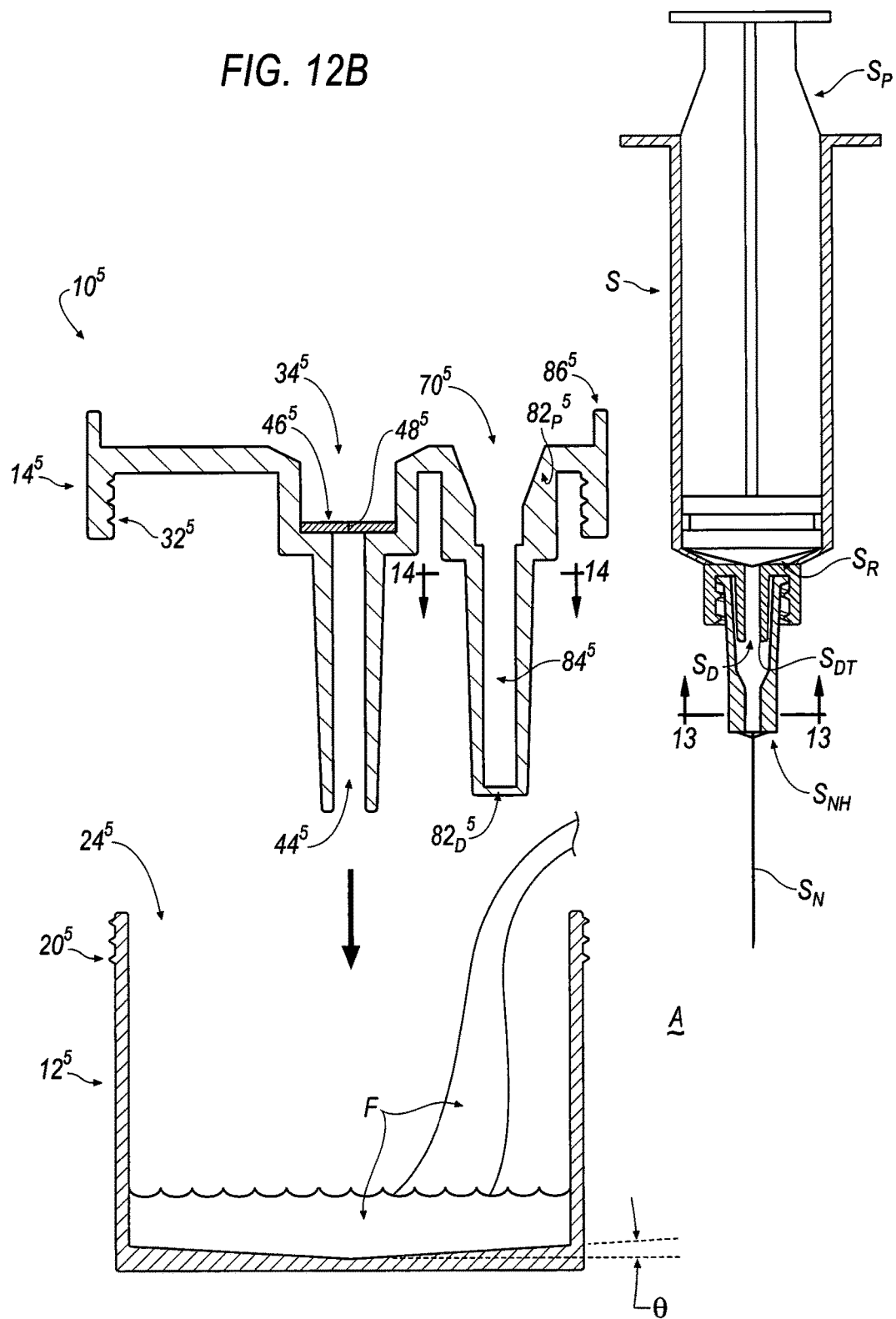
Figure 12D:
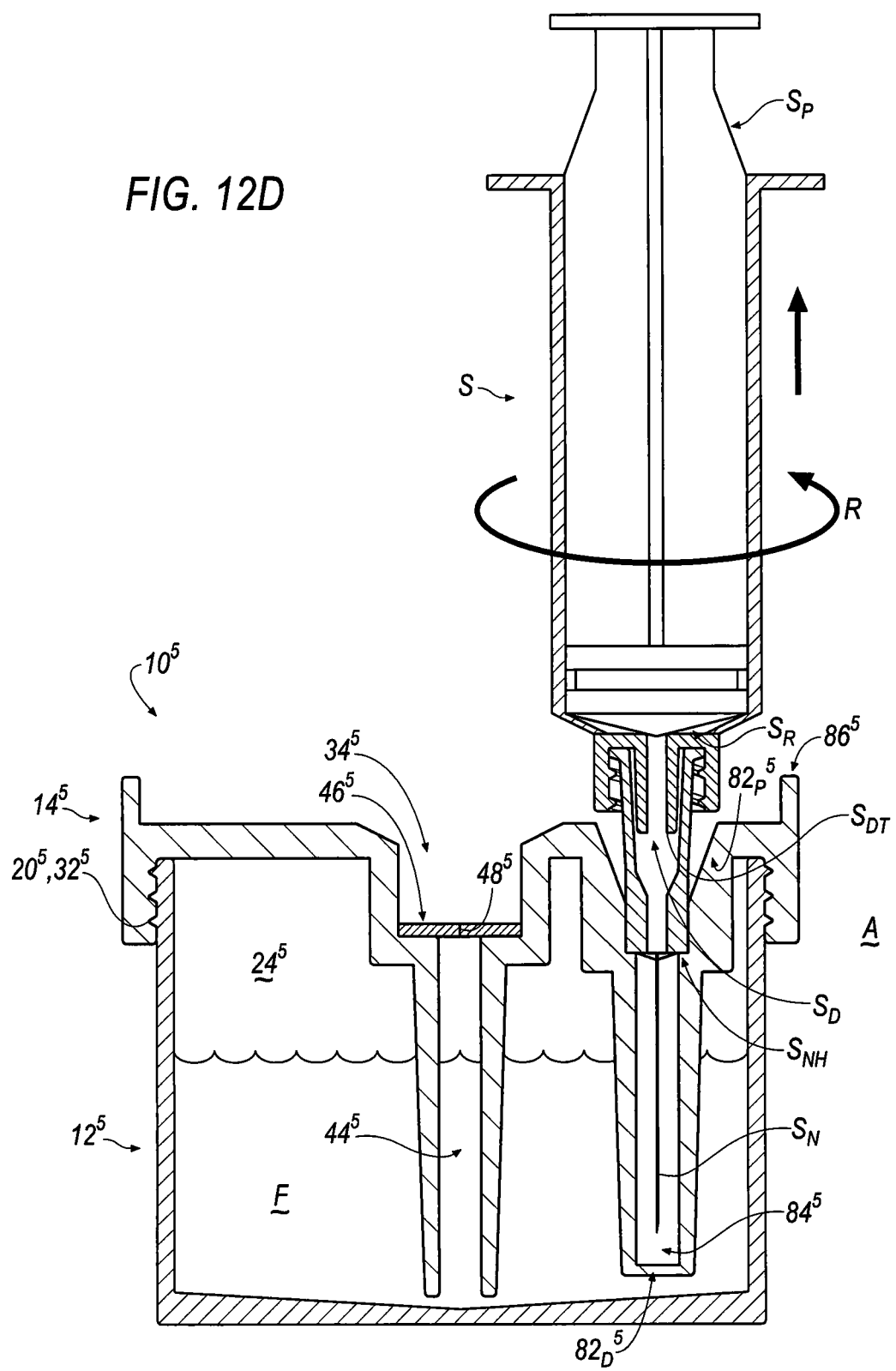
Figure 12E:
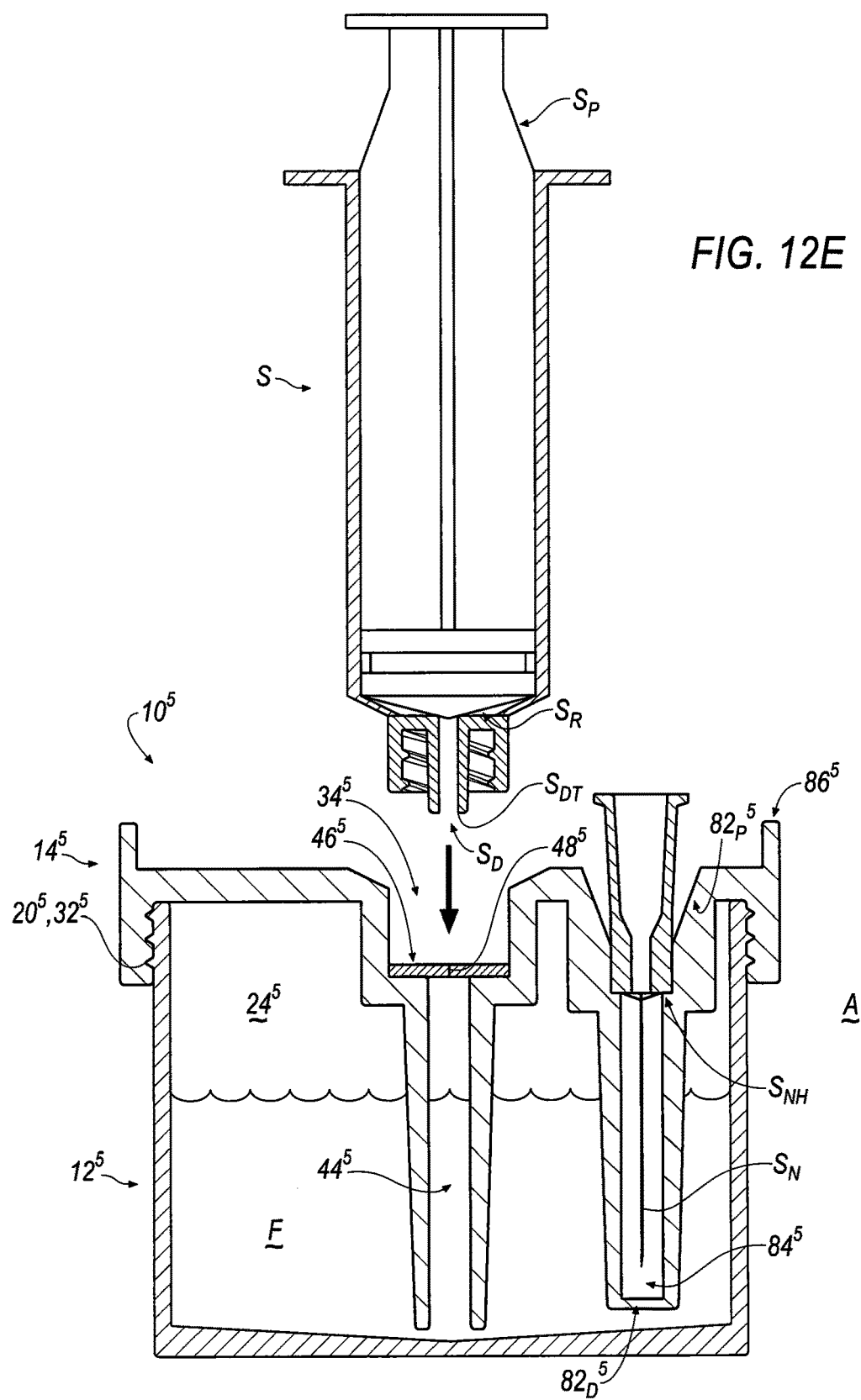
Figure 12F:
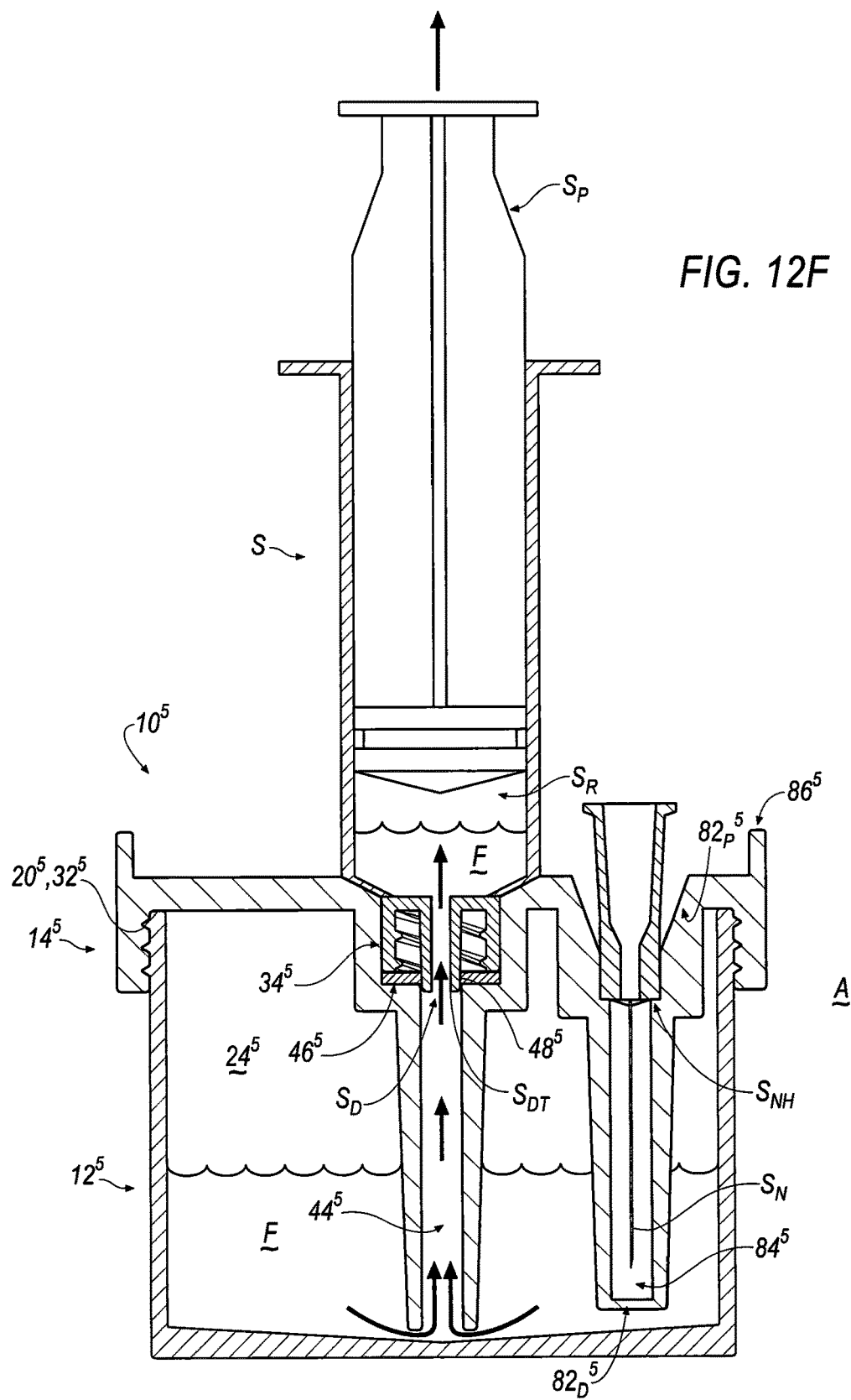
Figure 12G:
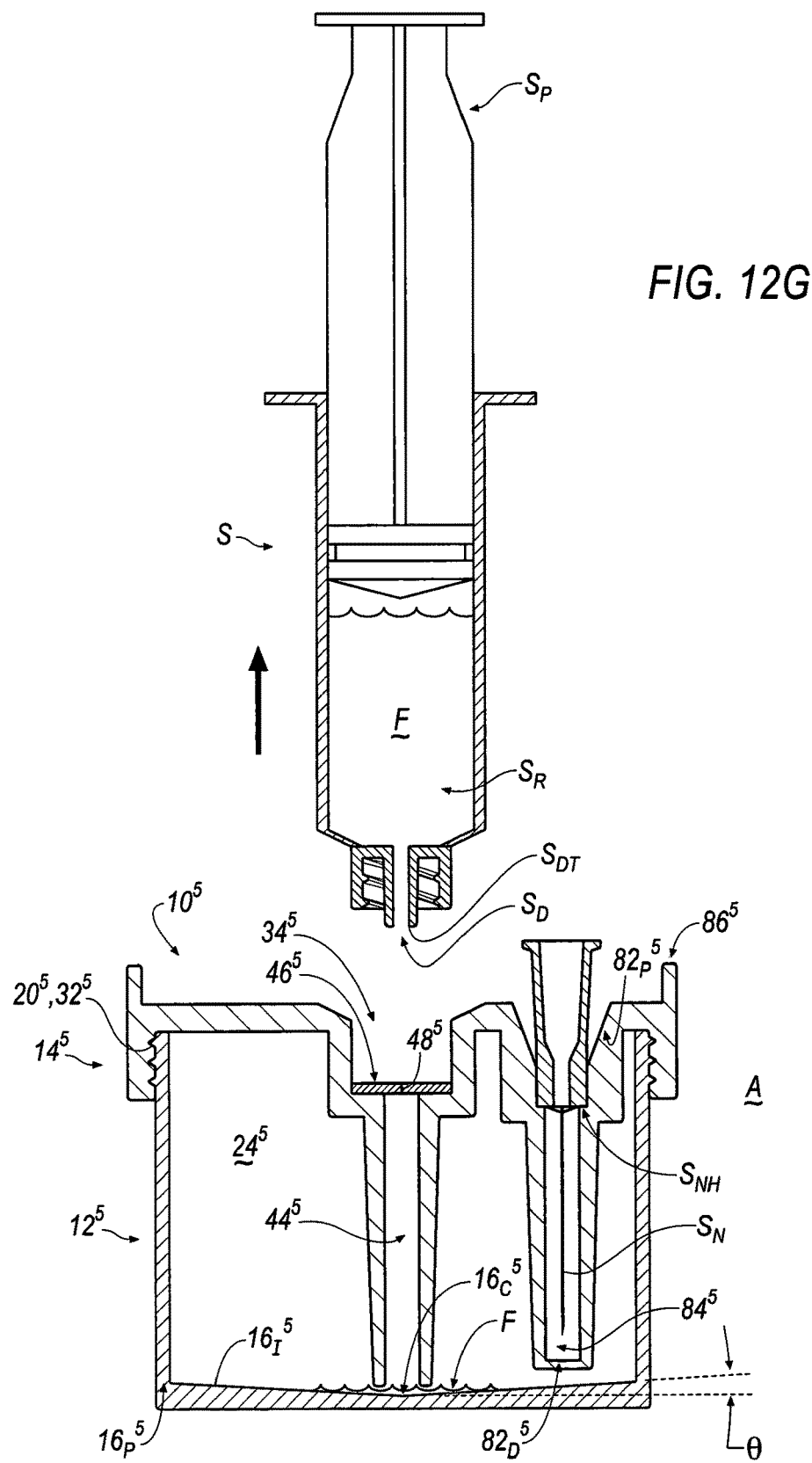

Referring to FIGS. 12B-12H, a method for utilizing the container assembly $10^5$ is described. Referring firstly to FIG. 12B, the container closure $14^5$ is shown disengaged from the container 12, and, a fluid, F, is disposed within the fluid reservoir $24^5$. Referring to FIG. 12C, the container closure $14^5$ is connected (e.g., threadingly-connected) to the container $12^5$ by, for example, the cooperating threaded surfaces $20^5$, $32^5$ of the container $12^5$ and container closure $14^5$ thereby fluidly sealing the fluid reservoir $24^4$ from surrounding atmosphere, A. Once the container closure $14^5$ is secured to the container 12, the distal tip of the needle, $S_N$, may be axially-aligned with and arranged over the needle hub-receiving bore $70^5$ and the needle-receiving passage $84^5$ formed in the end wall $28^5$ of the container closure $14^5$.

Referring to FIG. 12C, the distal tip of the needle, $S_N$, is firstly inserted into needle hub-receiving bore $70^5$ and then subsequently into the needle-receiving passage $84^5$ until all of the length of the needle, $S_N$, is disposed within the needle-receiving passage $84^5$ and the needle hub, $S_{NH}$, is disposed within the needle hub-receiving bore $70^5$. Referring to FIG. 12D, once the needle hub, $S_{NH}$, is disposed within the needle hub-receiving bore $70^5$ such that the flanged portion, $S_{N-F}$, of the needle hub, $S_{NH}$, is received by the first axial wall surface $74^5$ and the second shoulder surface $76^5$ of the needle hub-receiving bore $70^5$, the user may then apply a rotational force, R, to the syringe, S, in order to cause the syringe, S, to be disconnected from the needle hub, $S_{NH}$ (i.e., when the flanged portion, $S_{N-F}$, of the needle hub, $S_{NH}$, is interfaced with the first axial wall surface $74^5$ and the second shoulder surface $76^5$ of the needle hub-receiving bore $70^5$, the syringe, S, is permitted to rotate, R, relative to a spatially-fixed orientation of the needle hub, $S_{NH}$, that is rotationally fixed-in-place within the needle hub-receiving bore $70^5$ thereby permitting the syringe, S, to rotate relative to and be disconnected from the needle hub, $S_{NH}$). As seen in FIG. 12E, the user may then arranging the syringe, S, in axial alignment with the syringe-receiving bore $34^5$ without the needle hub, $S_{NH}$, connected thereto as the needle hub, $S_{NH}$, remains docked within the needle hub-receiving bore $70^5$ with the needle, $S_N$ (which is connected to the needle hub, $S_{NH}$), remaining docked within the needle-receiving passage $84^5$.

Referring to FIG. 12E, the distal end, $S_D$, of the syringe, S, may then be axially-aligned with and arranged over the syringe-receiving bore $34^5$ formed in the central portion $28_C^5$ of the end wall $28^5$ of the container closure $14^5$ for subsequent insertion into the syringe-receiving bore $34^5$. Referring to FIG. 12F, once the distal end, $S_D$, of the syringe, S, is arranged within the syringe-receiving bore $34^5$, the distal tip, $S_{DT}$, of the syringe, S, axially penetrates the slit $48^5$ to thereby arrange a fluid reservoir, $S_R$, of the syringe, S, in fluid communication with the fluid-flow passage $44^5$ that is in fluid communication with the fluid, F, contained by the fluid reservoir $24^5$. As seen in FIG. 12F, once the fluid reservoir, $S_R$, of the syringe, S, is in fluid communication with the fluid-flow passage $44^5$ as described above, a user may axially manipulate the plunger, $S_P$, of the syringe, S, in order to draw the fluid, F, from the fluid reservoir $24^5$ into the fluid reservoir, $S_R$, of the syringe, S, by way of the fluid-flow passage $44^5$.

Referring to FIG. 12G, once the user has withdrawn a desired amount of fluid, F, from the fluid reservoir $24^5$ and into the fluid reservoir, $S_R$, of the syringe, S, the user may remove the distal end, $S_D$, of the syringe, S, from the syringe-receiving bore $34^5$. Once the distal end, $S_D$, of the syringe, S, is withdrawn from the syringe-receiving bore $34^5$, the distal tip, $S_{DT}$, of the syringe, S, no longer penetrates the slit $48^5$, and, as a result, the disk-shaped member $46^5$ may return to its pre-penetrated state, thereby fluidly sealing the fluid flow passage $44^5$ and the fluid reservoir $24^5$ from surrounding atmosphere, A.

As seen in FIG. 12G, the conically-pitched angle, $\theta$, formed by the inner surface $16_I^5$ of the end wall $16^5$, directs a remainder of non-withdrawn fluid, F, disposed upon the inner surface $16_I^5$ of the end wall $16^5$ (with the assistance of gravity) away from the outer perimeter portion $16_P^5$ of the end wall $16^5$ and toward the central portion $16_C^5$ of the end wall $16^5$; as a result, the remainder of the non-withdrawn fluid, F, may be arranged/aligned with the fluid-flow passage $44^5$ for subsequent withdrawal from the container $12^5$.

Figure 12H:
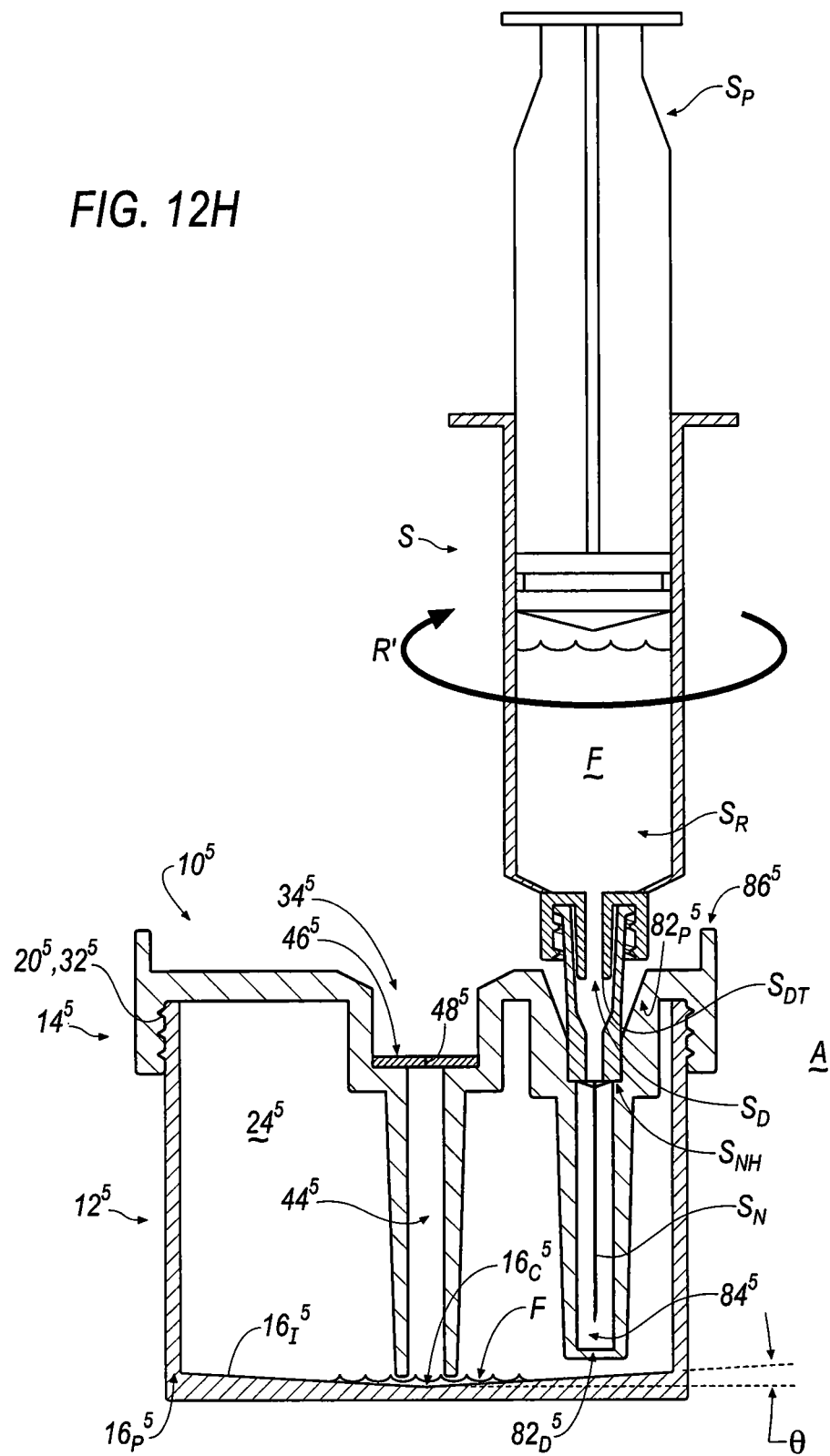
Figure 12I:
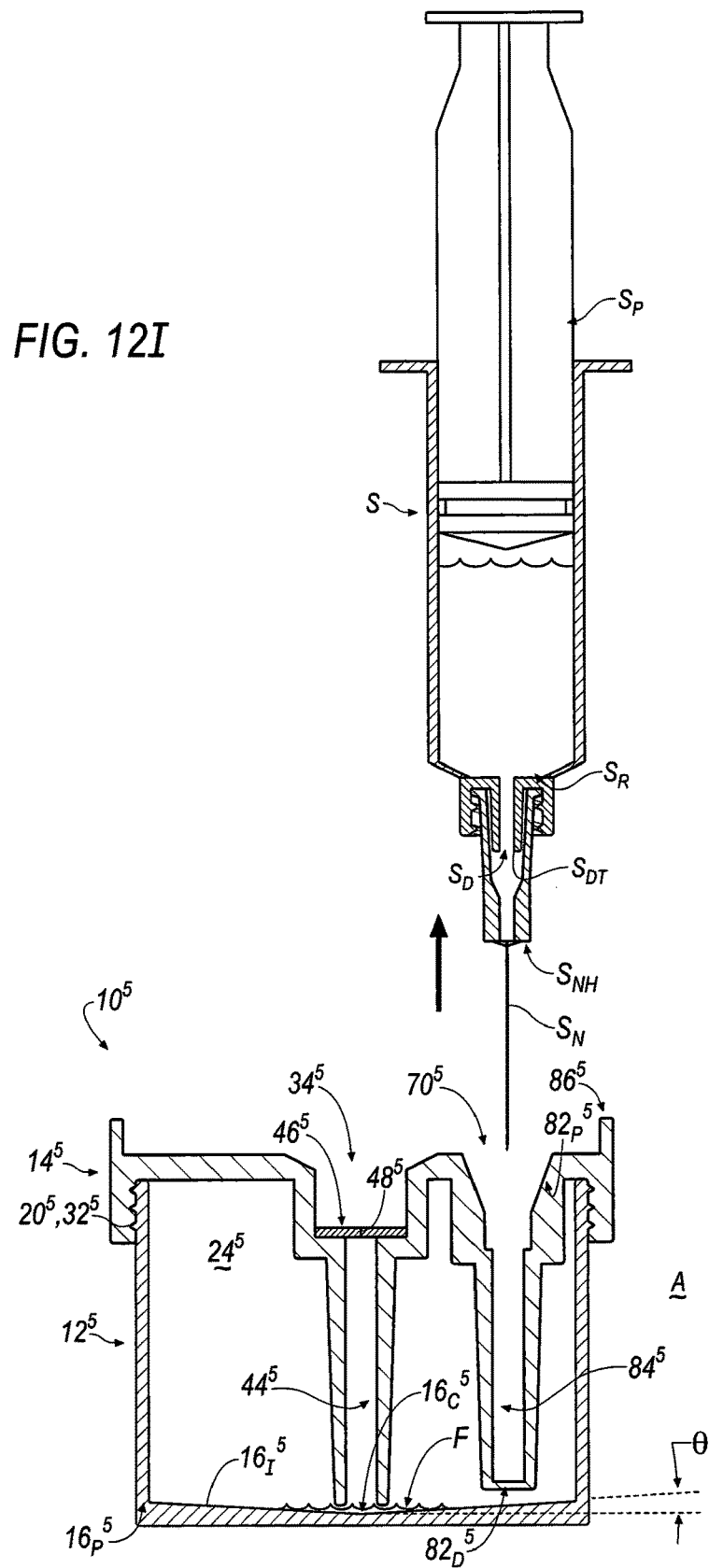

Referring now to FIG. 12H, the distal end, $S_D$, of the syringe, S, may then be axially-aligned with and arranged over the needle hub-receiving bore $70^5$ for subsequent insertion into the needle hub-receiving bore $70^5$ that contains the needle hub, $S_{NH}$. Once the distal end, $S_D$, of the syringe, S, is arranged within the needle hub-receiving bore $70^5$, the distal tip, $S_{DT}$, of the syringe, S, is axially interfaced with the needle hub, S. The user may then apply a rotational force, R' (that is opposite the rotational force, R), to the syringe, S, in order to cause the syringe, S, to be reconnected to the needle hub, $S_{NH}$ (i.e., when the flanged portion, $S_{N-F}$, of the needle hub, $S_{NH}$, is interfaced with the first axial wall surface $74^5$ and the second shoulder surface $76^5$ of the needle hub-receiving bore $70^5$, the needle hub, $S_{NH}$, is held in place while the syringe, S, is reattached to the needle hub, $S_{NH}$). Referring to FIG. 12I, once the syringe, S, is reconnected to the needle hub, $S_{NH}$, the syringe, S, may be axially withdrawn from the needle hub-receiving bore $70^5$, which also causes the needle hub, $S_{NH}$, and the needle, $S_N$ (which is connected to the needle hub, $S_{NH}$), to be withdrawn from the needle hub-receiving bore $70^5$ and the needle-receiving passage $84^5$.

Figure 15:
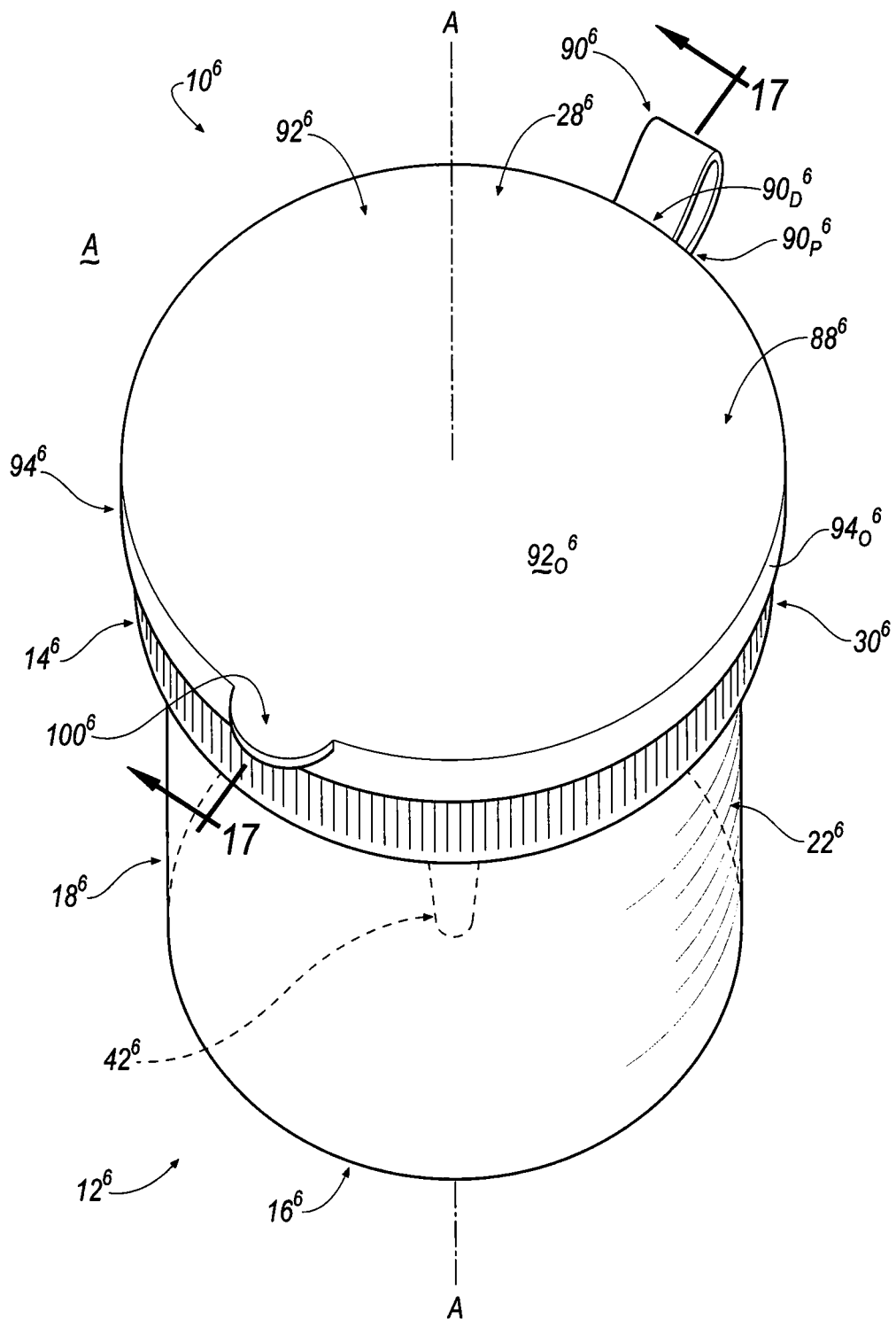
FIG. 15 illustrates a perspective view of a container assembly arranged in a first orientation in accordance with an exemplary embodiment of the invention.
Figure 16:
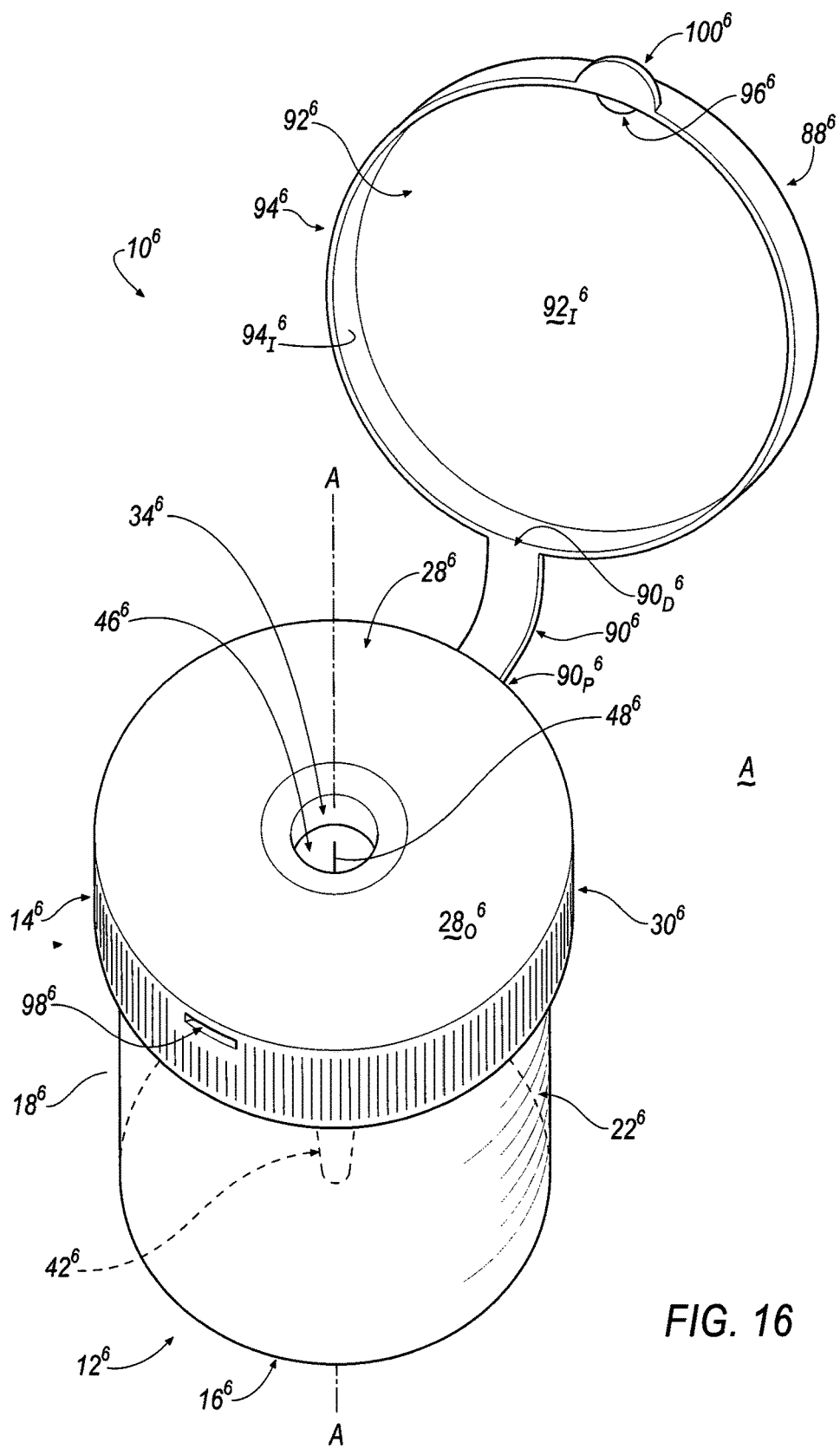
FIG. 16 illustrates a perspective view of the container assembly of FIG. 15 arranged in a second orientation in accordance with an exemplary embodiment of the invention.

An exemplary container assembly is shown generally at $10^6$ in FIGS. 15-16. The container assembly $10^6$ generally includes a container $12^6$ and a container closure $14^6$. The container assembly $10^6$ includes a cover member $88^6$ that is attached to the container closure $14^6$ by a tether $90^6$. The cover member $88^6$ may be arranged relative to the container closure $14^6$ in a closed orientation (as seen in FIG. 15) or an open orientation (as seen in FIG. 16).

Figure 17A:
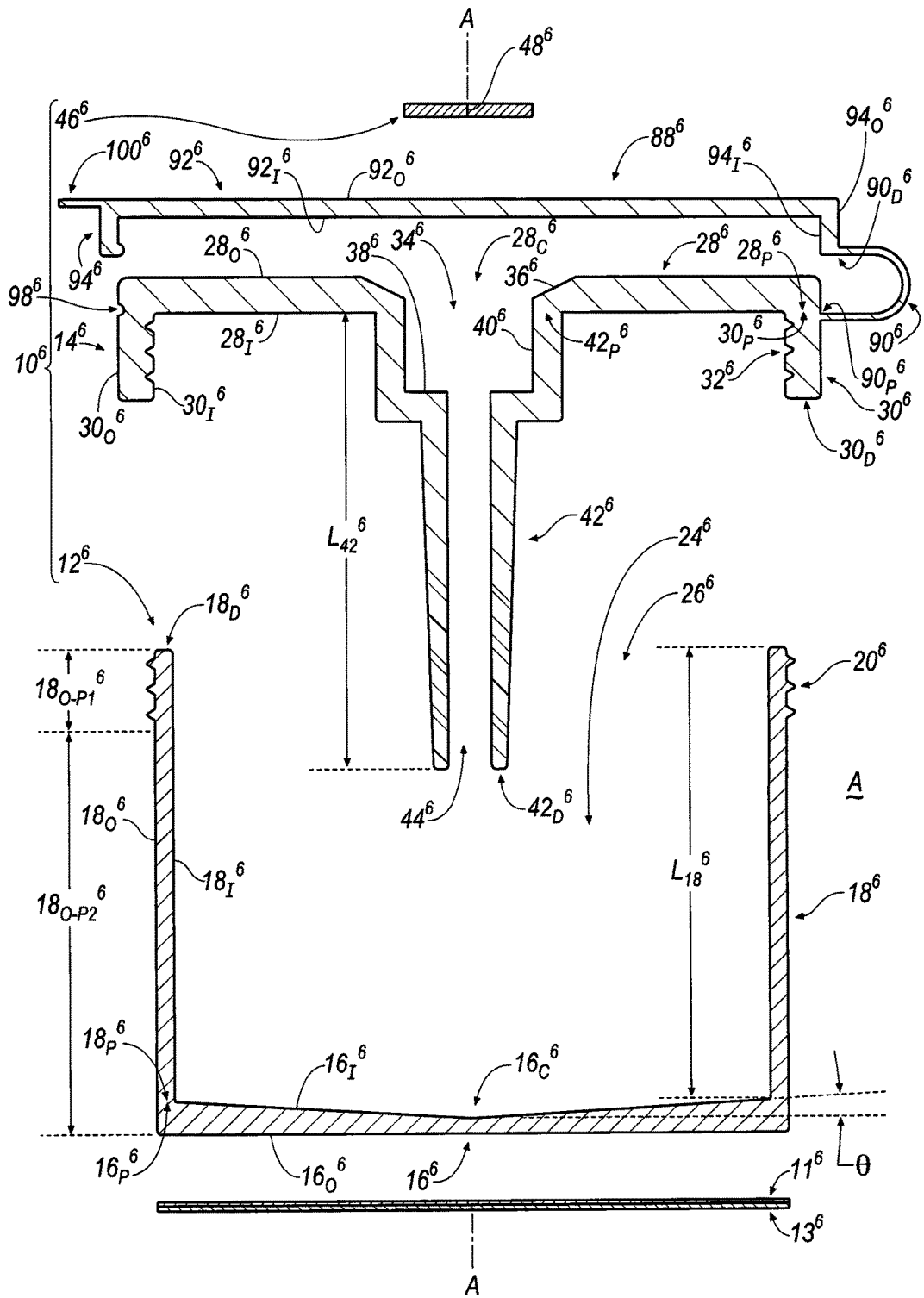
FIG. 17A is an exploded cross-sectional view of the container assembly according to line 17-17 of FIG. 15.

Referring to FIG. 17A, the container $12^6$ includes an end wall $16^6$ and a side wall $18^6$. The end wall $16^6$ and the side wall $18^6$ may include any desirable material or geometry. In some instances, the container $12^6$ may include a clear plastic or glass material; in some implementations, the material may include a coating (e.g., an antimicrobial coating). In some examples as seen in FIGS. 15-16, the end wall $16^6$ may define an annular member and the side wall $18^6$ may define a cylindrical, tube-shaped body.

As seen in FIG. 17A, the end wall $16^6$ includes a central portion $16^6$ and an outer perimeter portion $16_P^6$. The side wall $18^6$ includes a proximal end $18_P^6$ and a distal end $18_D^6$. The proximal end $18_P^6$ of the side wall $18^6$ is connected to and extends away from the outer perimeter portion $16_P^6$ of the end wall $16^6$.

The end wall $16^6$ includes an inner surface $16_I^6$ and an outer surface $16_O^6$. The inner surface $16_I^6$ of the end wall $16^6$ may be conically-pitched according to an angle, A, to define the central portion $16_C^6$ of the end wall $16^6$ the container $12^6$ to be a low point of the inner surface $16_I^6$ of the end wall $16^6$ of the container $12^6$. In some instances, the angle may be approximately equal to 15°. In some examples, the container $12^6$ may optionally include an adhesive $11^6$ applied over the outer surface $16_O^6$ of the end wall $16^6$. In some instances, an optional release paper $13^6$ may be applied over the adhesive $11^6$. Prior to disposing the container $12^6$ upon a support surface, a user may remove the release paper (thereby exposing the adhesive $11^6$ applied over the outer surface $16_O^6$ of the end wall $16^6$); the exposed adhesive $13^6$ may assist in the prevention of movement of the container $12^6$ upon the support surface once the outer surface $16_O^6$ of the end wall $16^6$ is arranged upon the support surface.

The side wall $18^6$ includes an inner surface $18_I^6$ and an outer surface $18_O^6$. A first portion $18_{O-P1}^6$ of the outer surface $18_O^6$ of the side wall $18^6$ may define an outer threaded surface $20^6$ of the container $12^6$. A second portion $18_{O-P2}^6$ of the outer surface $18_O^6$ of the side wall $18^6$ may include printed indicia $22^6$ (as seen in FIGS. 15-16) defining, for example, an amount of fluid disposed within the container $12^6$. As will be described in the following disclosure, the outer threaded surface $20^6$ of the container $12^6$ may cooperate with an inner threaded surface $32^6$ of the container closure $14^6$ for selectively attaching the container closure $14^6$ to the container $12^6$.

The container $12^6$ forms a fluid reservoir $24^6$ that is defined by the inner surface $16_I^6$, $18_I^6$ of both of the end wall $16^6$ and the side wall $18^6$. Access to the fluid reservoir $24^6$ is permitted by an opening $26^6$ formed by the distal end $18_D^6$ of the side wall $18^6$.

Referring to FIG. 17A, the container closure $14^6$ includes an end wall $28^6$ and a side wall $30^6$. The end wall $28^6$ and the side wall $30^6$ may include any desirable material or geometry. In some instances, the container closure $14^6$ may include an opaque plastic material; in some implementations, the material may include a coating (e.g., an antimicrobial coating). In some examples as seen in FIGS. 15-16, the end wall $28^6$ may define an annular member and the side wall $30^6$ may define a cylindrical, tube-shaped body.

As seen in FIG. 17A, the end wall $28^6$ includes a central portion $28_C^6$ and an outer perimeter portion $28_P^6$. The side wall $30^6$ includes a proximal end $30_P^6$ and a distal end $30_D^6$. The proximal end $30_P^6$ of the side wall $30^6$ is connected to and extends away from the outer perimeter portion $28_P^6$ of the end wall $28^6$. The central portion $28_C^6$ of the end wall $28^6$ of the container closure $14^6$ and the central portion $16^6$ of the end wall $16^6$ of the container $12^6$ may be aligned with a central axis, A-A, extending through the container assembly $10^6$.

The end wall $28^6$ includes an inner surface $28_I^6$ and an outer surface $28_O^6$. The side wall $30^6$ includes an inner surface $30_I^6$ and an outer surface $30_O^6$. The inner surface $30_I^6$ of the side wall $30^6$ may define an inner threaded surface $32^6$ of the container closure $14^6$. As will be described in the following disclosure, the inner threaded surface $32^6$ of the container closure $14^6$ may cooperate with the outer threaded surface $20^6$ of the container $12^6$ for selectively attaching the container closure $14^6$ to the container $12^6$.

The outer surface $28_O^6$ of the end wall $28^6$ of the container closure $14^6$ generally defines a syringe-engaging portion, such as, for example, a syringe-receiving bore $34^6$. The syringe-receiving bore $34^6$ is formed in the central portion $28_C^6$ of the end wall $28^6$ of the container closure $14^6$. An axial center of the syringe-receiving bore $34^6$ is aligned with the central axis, A-A.

The syringe-receiving bore $34^6$ is defined by portions $36^6$, $38^6$, $40^6$ of the outer surface $28_O^6$ of the end wall $28^6$ of the container closure $14^6$ and sized for receiving a distal end, $S_D$ (see, e.g., FIGS. 17B-17G), of a syringe, S (see, e.g., FIGS. 17B-17G). The portions $36^6$, $38^6$, $40^6$ of the outer surface $28_O^6$ of the end wall $28^6$ of the container closure $14^6$ includes: a first shoulder surface $36^6$, a second shoulder surface $38^6$ and an axial wall surface $40^6$ extending substantially perpendicularly from the second shoulder surface $38^6$ and connects the first shoulder surface $36^6$ to the second shoulder surface $38^6$. The first shoulder surface $36^6$ may be tapered in order to conform to a tapered outer wall surface portion of the distal end, $S_D$, of the syringe, S.

The container closure $14^6$ also includes a fluid-drawing member $42^6$ that extends axially away from and is integral with the inner surface $28_I^6$ of the end wall $28^6$ of the container closure $14^6$. The fluid-drawing member $42^6$ includes a proximal end $42_P^6$ and a distal end $42_D^6$. A fluid-flow passage $44^6$ extends through the fluid-drawing member $42^6$ between the proximal end $42_P^6$ and the distal end $42_D^6$. The fluid-flow passage $44^6$ is aligned with an axial center of the fluid-drawing member $42^6$. When the container closure $14^6$ is connected to the container $12^6$, the fluid-flow passage $44^6$ is in fluid communication with the fluid reservoir $24^6$ defined by the container $12^6$.

The proximal end $42_P^6$ of the fluid-drawing member $42^6$ is connected to and extends away from the inner surface $28_I^6$ of the end wall $28^6$ of the container closure $14^6$. In some instances, the fluid-drawing member $42^6$ may extend away from the inner surface $28_I^6$ at the central portion $28_C^6$ of the end wall $28^6$ of the container closure $14^6$ (such that the fluid-drawing member $42^6$ is aligned with the central axis, A-A, when the container closure $14^6$ is attached to the container $12^6$).

The fluid-drawing member $42^6$ may also be defined by a length dimension, $L_{42}^6$. A portion of the syringe-receiving bore $34^6$ may extend into a portion of the length, $L_{42}^6$, defining the fluid-drawing member $42^6$. The length dimension $L_{42}^6$ of the fluid-drawing member $42^6$ may be approximately equal to, but slightly greater than a length $L_{18}^6$ of the side wall $18^6$ of the container $12^6$; due to the conically-pitched angle, $\theta$, formed by the inner surface $16_I^6$ of the end wall $16^6$, upon connecting the container closure $14^6$ to the container $12^6$, the distal end $42_D^6$ of the fluid-drawing member $42^6$ may be arranged substantially adjacent to but in a slightly spaced-apart relationship with respect to the inner surface $16_I^6$ of the end wall $16^6$ defined by the central portion $16^6$ of the end wall $16^6$ that is aligned with the central axis, A-A. By selectively defining the length relationship of the length dimensions $L_{42}^6$, $L_{18}^6$ of the fluid-drawing member $42^6$ and the side wall $18^6$, and, in addition, the axial alignment of the fluid-drawing member $42^6$ with respect to the central portion $28_C^6$ of the end wall $28^6$ of the container closure $14^6$, the fluid drawing member $42^6$ is selectively positioned relative to the container $12^6$ in order to draw a remainder of fluid, F, contained within the fluid reservoir $24^6$ when all of the fluid, F, contained within the container $12^6$ is nearly depleted as seen in FIG. 17F.

The container assembly $10^6$ also includes a disk-shaped member $46^6$ that is disposed upon and supported by one or both of the second shoulder surface $38^6$ and the axial wall surface $40^6$ defining the syringe-receiving bore $34^6$. The disk-shaped member $46^6$ may be secured to one or more of the second shoulder surface $38^6$ and the axial wall surface $40^6$ in any desirable fashion (e.g., with an adhesive or a friction-fit connection). The disk-shaped member $46^6$ may be formed from any desirable material including, for example, foam, rubber or the like.

The disk-shaped member $46^6$ selectively prevents fluid communication between the syringe-receiving bore $34^6$ and the fluid-flow passage $44^6$. The disk-shaped member $46^6$ also inhibits contaminates from surrounding atmosphere, A, from entering the fluid-flow passage $44^6$ and into the fluid reservoir $24^6$.

The disk-shaped member $46^6$ may include a slit $48^6$ that is aligned with an axial center of both of the container closure $14^6$ and the disk-shaped member $46^6$. The slit $48^6$ permits selective fluid communication with the fluid-flow passage $44^6$ and the fluid reservoir $24^6$ from surrounding atmosphere, A. Access to (i.e., fluid communication) with the fluid-flow passage $44^6$ from a device (e.g., the syringe, S) that is located in surrounding atmosphere, A, is permitted when a distal tip, $S_{DT}$, of the syringe, S, axially penetrates the slit $48^6$ as seen in FIG. 17E.

As seen at FIGS. 15-16 and 17A, the container assembly $10^6$ also includes the cover member $88^6$ that is attached to the container closure $14^6$ by the tether $90^6$. The cover member $88^6$ includes an end wall $92^6$ having an inner surface $92_I^6$ and an outer surface $92_O^6$. The cover member $88^6$ also includes a side wall $94^6$ having an inner surface $94_I^6$ and an outer surface $94_O^6$. The tether $90^6$ includes a proximal end $90_P^6$ and a distal end $90_D^6$.

The proximal end $90_P^6$ of the tether $90^6$ integrally extends radially away from the outer surface $30_O^6$ of the side wall $30^6$ of the container closure $14^6$. The distal end $90_D^6$ of the tether $90^6$ integrally extends from the outer surface $94_O^6$ of the side wall $94^6$ of the cover member $88^6$.

Referring to FIGS. 16 and 17A, the cover member $88^6$ may define a first portion of a snap-fit connection (such as, for example, a projection $96^6$). The projection $96^6$ may extend radially inwardly from the inner surface $94_I^6$ of the side wall $94^6$ of the cover member $88^6$. As seen in FIGS. 16 and 17A, the container closure $14^6$ may define a second portion of the snap-fit connection (such as, e.g., a recess $98^6$). The recess $98^6$ may be formed in the outer surface $30_O^6$ of the side wall $30^6$ of the container closure $14^6$ and opposite where the proximal end $90_P^6$ of the tether $90^6$ that integrally extends radially away from the outer surface $30_O^6$ of the side wall $30^6$ of the container closure $14^6$.

The snap-fit connection $96^6$, $98^6$ permits the cover member $88^6$ to be: (1) selectively secured to the container closure $14^6$ in a closed orientation (as seen in FIG. 15) or (2) selectively arranged relative the container closure $14^6$ in an open orientation (as seen in FIG. 16). When the cover member $88^6$ is arranged in the closed orientation, contaminates that may fall with gravity are less likely to infiltrate the syringe-receiving bore $34^6$.

The cover member $88^6$ may also include a flanged lip $100^6$ that extends radially outwardly from the outer surface $94_O{}^6$ of the side wall $94^6$. The flanged lip $100^6$ may be radially aligned with the snap-fit connection defined by the projection $96^6$ and the recess $98^6$ in order to assist in seating or unseating the projection $96^6$ relative the recess $98^6$.

Figure 17B:
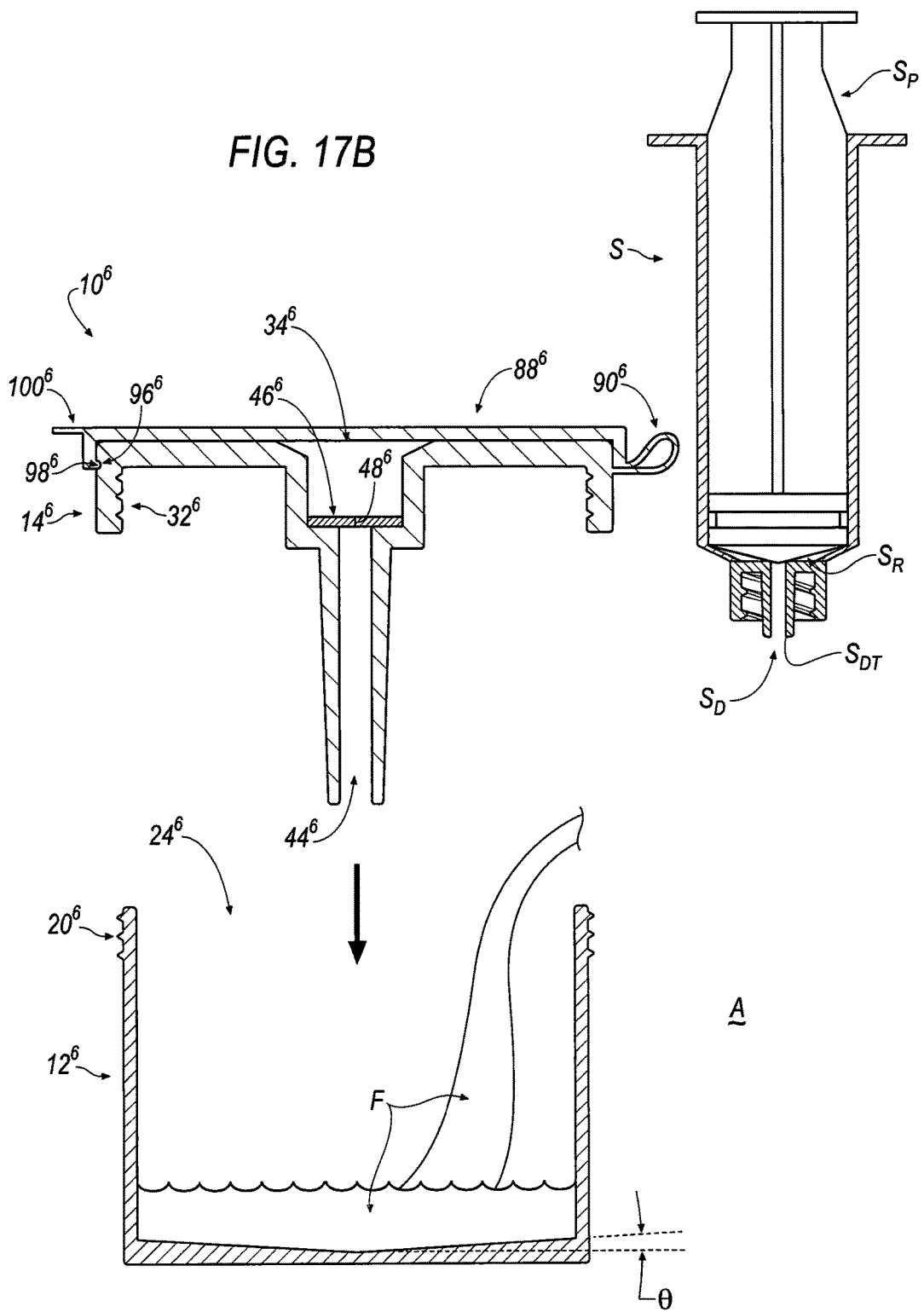
Figure 17C:
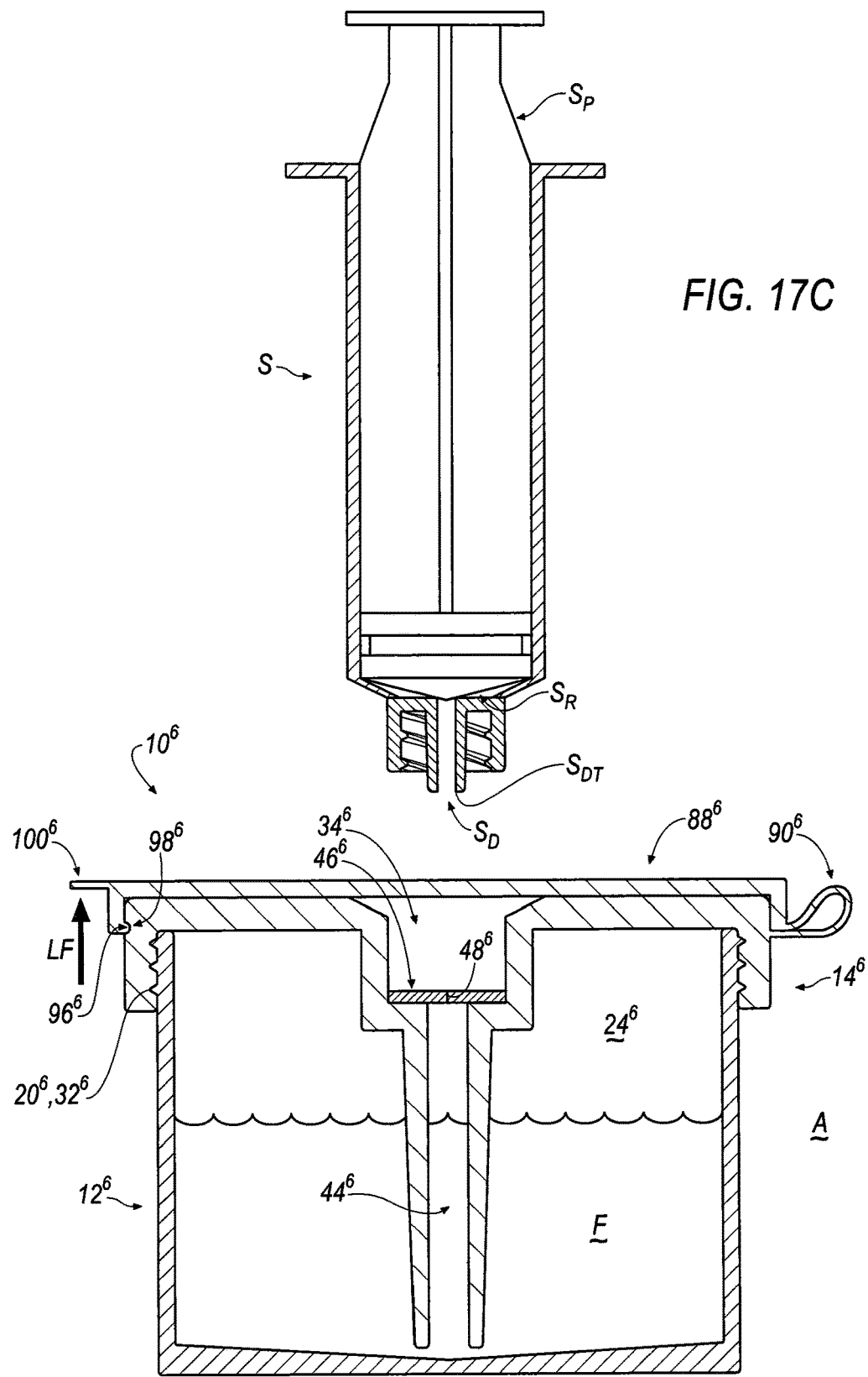
Figure 17D:
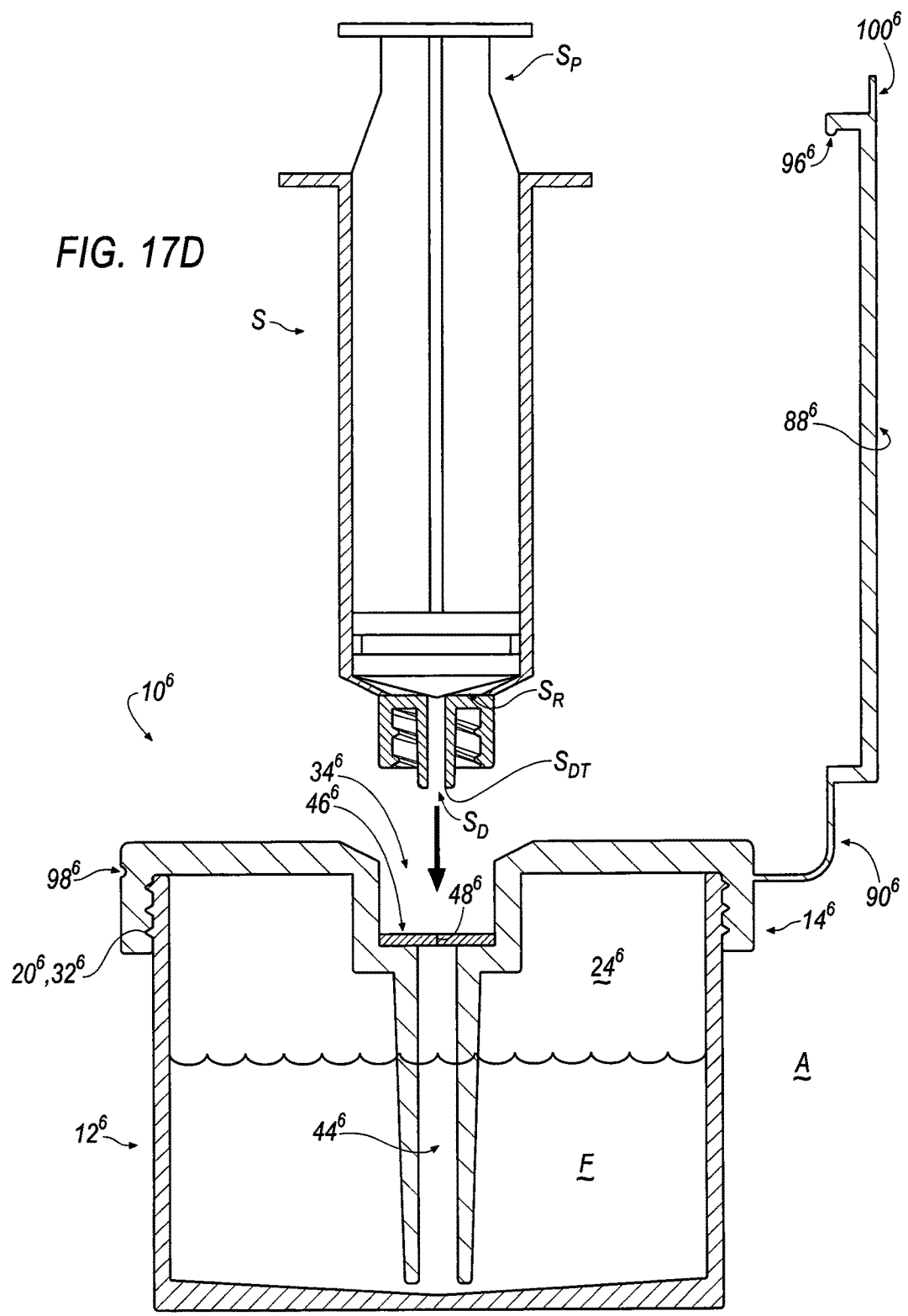
Figure 17F:
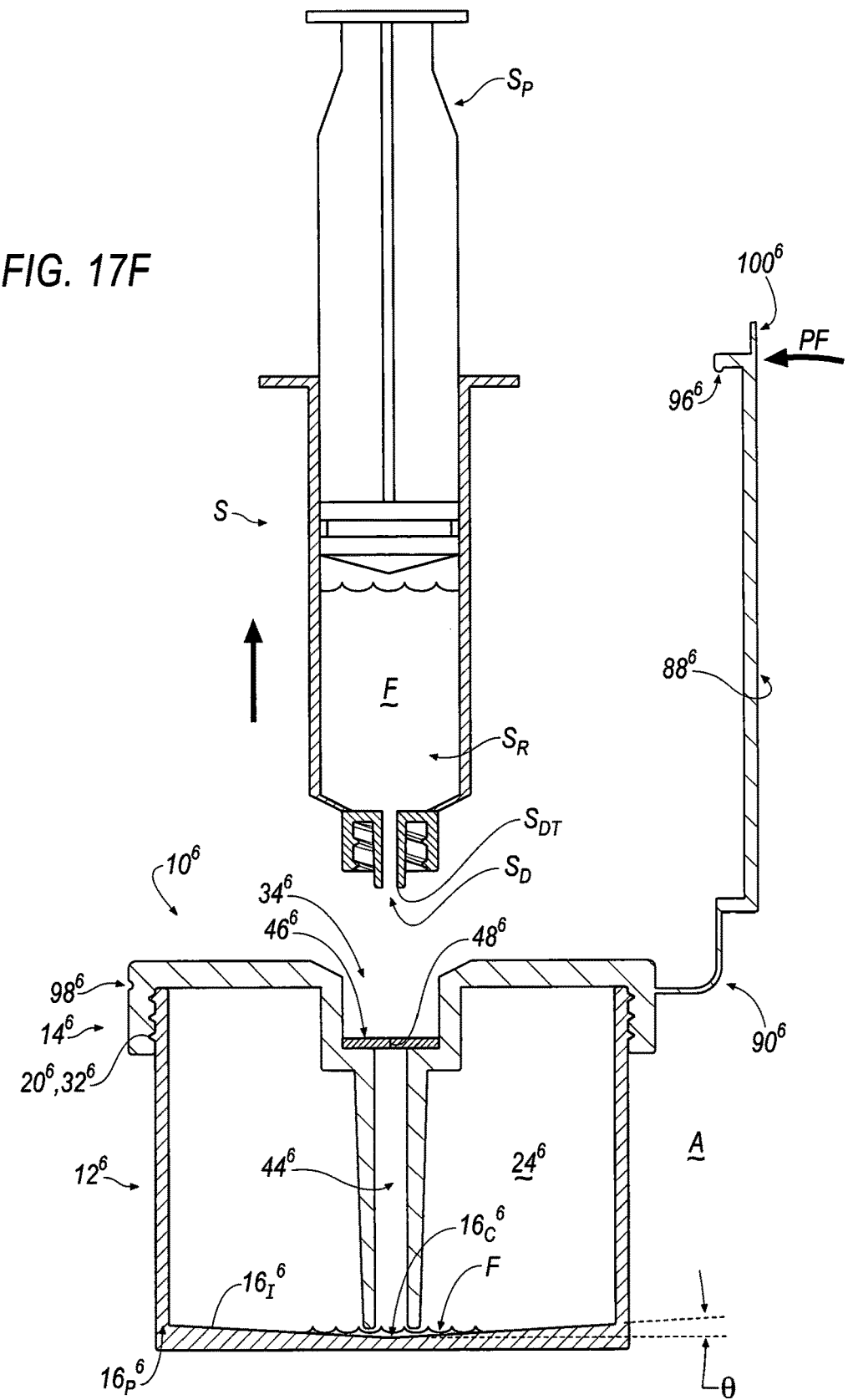

Referring to FIGS. 17B-17G, a method for utilizing the container assembly $10^6$ is described. As seen in FIG. 17B, the cover member $88^6$ may be secured to the container closure $14^6$ in a closed orientation (as seen in FIG. 15) as a result of the projection $96^6$ being seated in the recess $98^6$. As also seen in FIG. 17B, the container closure $14^6$ is shown disengaged from the container $12^6$, and, a fluid, F, is disposed within the fluid reservoir $24^6$. Referring to FIG. 17C, the container closure $14^6$ is connected (e.g., threadingly-connected) to the container $12^6$ by, for example, the cooperating threaded surfaces $20^6$, $32^6$ of the container $12^6$ and container closure $14^6$ thereby fluidly sealing the fluid reservoir $24^6$ from surrounding atmosphere, A. Then, as seen in FIG. 17C, the user may apply a lifting force, LF, to the flanged lip $100^6$ in order to unseat the projection $96^6$ from the recess $98^6$ in order to arrange the cover member $88^6$ relative the container closure $14^6$ in an open orientation (as seen in FIGS. 16, 17D). Referring to FIG. 17D, once the container closure $14^6$ is secured to the container $12^6$, and, once the cover member $88^6$ is arranged relative to the container closure $14^6$ in the open orientation, the distal end, $S_D$, of the syringe, S, may be axially-aligned with and arranged over the syringe-receiving bore $34^6$ formed in the central portion $28_C{}^6$ of the end wall $28^6$ of the container closure $14^6$.

Referring to FIG. 17E, the distal end, $S_D$, of the syringe, S, is inserted into the syringe-receiving bore $34^6$ and the distal tip, $S_{DT}$, of the syringe, S, axially penetrates the slit $48^6$ to thereby arrange a fluid reservoir, $S_R$, of the syringe, S, in fluid communication with the fluid-flow passage $44^6$ that is in fluid communication with the fluid, F, contained by the fluid reservoir $24^6$. Once the fluid reservoir, $S_R$, of the syringe, S, is in fluid communication with the fluid-flow passage $44^6$ as described above, a user may axially manipulate a plunger, $S_P$, of the syringe, S, in order to draw the fluid, F, from the fluid reservoir $24^6$ into the fluid reservoir, $S_R$, of the syringe, S, by way of the fluid-flow passage $44^6$.

Referring to FIG. 17F, once the user has withdrawn a desired amount of fluid, F, from the fluid reservoir $24^6$ and into the fluid reservoir, $S_R$, of the syringe, S, the user may remove the distal end, $S_D$, of the syringe, S, from the syringe-receiving bore $34^6$. Once the distal end, $S_D$, of the syringe, S, is withdrawn from the syringe-receiving bore $34^6$, the distal tip, $S_{DT}$, of the syringe, S, no longer penetrates the slit $48^6$, and, as a result, the disk-shaped member $46^6$ may return to its pre-penetrated state, thereby fluidly sealing the fluid-flow passage $44^6$ and the fluid reservoir $24^6$ from surrounding atmosphere, A. Then, as seen in FIGS. 17F-17G, the user may apply a pushing force, PF, to the flanged lip $100^6$ in order to seat the projection $96^6$ within the recess $98^6$ in order to return the cover member $88^6$ to the container closure $14^6$ to the closed orientation (as seen in FIG. 16).

Figure 17G:
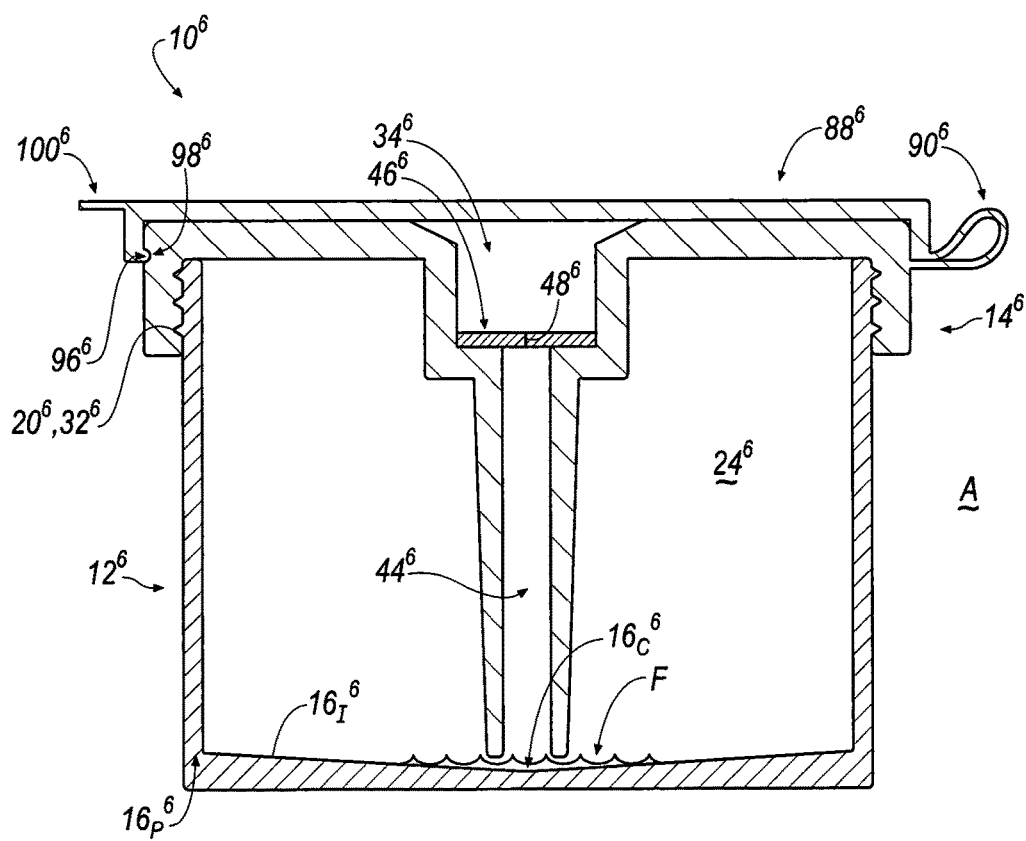

As seen in FIGS. 17F-17G, the conically-pitched angle, θ, formed by the inner surface $16_I{}^6$ of the end wall $16^6$, directs a remainder of non-withdrawn fluid, F, disposed upon the inner surface $16_I{}^6$ of the end wall $16^6$ (with the assistance of gravity) away from the outer perimeter portion $16_P{}^6$ of the end wall $16^6$ and toward the central portion $16_C{}^6$ of the end wall $16^6$; as a result, the remainder of the non-withdrawn fluid, F, may be arranged/aligned with the fluid-flow passage $44^6$ for subsequent withdrawal from the container $12^6$.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

What is claimed is:

1. A portion of a container assembly comprising:
a container closure including an end wall connected to a side wall, wherein the end wall includes a central portion and an outer perimeter portion, wherein the side wall includes a proximal end and a distal end, wherein the proximal end of the side wall is connected to and extends away from the outer perimeter portion of the end wall, wherein the end wall includes an inner surface and an outer surface, wherein the side wall includes an inner surface and an outer surface; and
a needle sheath member that extends axially away from and is integral with the inner surface of the end wall of the container closure, wherein the needle sheath member forms a needle-receiving passage that is sized for receiving a needle extending from a needle hub that is removably-attached to a syringe, wherein the needle-receiving passage is in fluid communication with a needle hub-engaging portion that is defined by the outer surface of the end wall of the container closure, and wherein the needle hub-engaging portion is sized for receiving the needle hub that is removably-attached to a syringe;
wherein the outer surface of the end wall of the container closure defines a syringe-engaging portion, and
wherein the container closure includes a fluid-drawing member that extends axially away from and is integral with the inner surface of the end wall of the container closure, wherein the fluid-drawing member includes a proximal end and a distal end, wherein a fluid-flow passage extends through the fluid-drawing member between the proximal end of the fluid-drawing member and the distal end of the fluid-drawing member, and wherein the proximal end of the fluid-drawing member is connected to and extends away from the inner surface of the end wall of the container closure.

2. The portion of the container assembly according to claim 1, wherein the syringe-engaging portion is aligned with a central axis extending through an axial center of the container closure, and wherein the needle hub-engaging portion and the needle-receiving passage are radially-offset with respect to the central axis extending through an axial center of the container closure.

3. The portion of the container assembly according to claim 1, wherein the needle hub-engaging portion is a needle hub-receiving bore.

4. The portion of the container assembly according to claim 3, wherein one or more surface portions of the needle hub-receiving bore are sized for receiving a flanged portion of the needle hub.

5. The portion of the container assembly according to claim 1 further comprising:

a flange wall that extends axially away from and is integral with the outer surface of the end wall of the container closure.

6. The portion of the container assembly according to claim 1 further comprising:
    a cover member attached to the container closure by a tether, wherein the cover member includes an end wall having an inner surface and an outer surface, wherein the cover member includes a side wall having an inner surface and an outer surface, wherein the tether includes a proximal end and a distal end, wherein the proximal end of the tether integrally extends radially away from the outer surface of the side wall of the container closure, and wherein the distal end of the tether integrally extends from the outer surface of the side wall of the cover member.

7. The portion of the container assembly according to claim 6, wherein the cover member defines a first portion of a snap-fit connection including a projection, wherein the projection extends radially inwardly from the inner surface of the side wall of the cover member, wherein the container closure defines a second portion of the snap-fit connection including a recess, and wherein the recess is formed in the outer surface of the side wall of the container closure and opposite where the proximal end of the tether integrally extends radially away from the outer surface of the side wall of the container closure.

8. The portion of the container assembly according to claim 7, wherein the cover member includes a flanged lip that extends radially outwardly from the outer surface of the side wall of the cover member, and wherein the flanged lip is radially aligned with the snap-fit connection defined by the projection and the recess.

9. A container assembly, comprising:
    a container closure including an end wall connected to a side wall, wherein the end wall includes a central portion and an outer perimeter portion, wherein the side wall includes a proximal end and a distal end, wherein the proximal end of the side wall is connected to and extends away from the outer perimeter portion of the end wall, wherein the end wall includes an inner surface and an outer surface, wherein the side wall includes an inner surface and an outer surface; and
    a container connected to the container closure, wherein the container includes an end wall and a side wall, wherein the end wall of the container includes a central portion and an outer perimeter portion, wherein the side wall of the container includes a proximal end and a distal end, wherein the proximal end of the side wall of the container is connected to and extends away from the outer perimeter portion of the end wall of the container, wherein an inner surface of the end wall of the container and an inner surface of the side wall of the container form a fluid reservoir, wherein access to the fluid reservoir is permitted by an opening formed by a distal end of the side wall of the container; wherein the outer surface of the end wall of the container closure defines a syringe-engaging portion, wherein the container closure includes a fluid-drawing member that extends axially away from and is integral with the inner surface of the end wall of the container closure, wherein the fluid-drawing member includes a proximal end and a distal end, wherein a fluid-flow passage extends through the fluid-drawing member between the proximal end of the fluid-drawing member and the distal end of the fluid-drawing member, and wherein the proximal end of the fluid-drawing member is connected to and extends away from the inner surface of the end wall of the container closure, and wherein the fluid-drawing member extends through the opening and into the fluid reservoir, and wherein a distal end of the fluid-drawing member is arranged proximate the inner surface of the end wall of the container, wherein the container closure further includes a disk-shaped member including a slit, wherein the disk-shaped member is disposed upon and supported by one or more of a shoulder surface and an axial wall surface defining the syringe-engaging portion.

10. The container assembly according to claim 9, wherein the inner surface of the side wall of the container closure is connected to an outer surface of the side wall of the container.

11. The container assembly according to claim 10, wherein the inner surface of the side wall of the container closure defines an inner threaded surface, wherein the outer surface of the side wall of the container defines an outer threaded surface, and wherein the inner threaded surface is connected to the outer threaded surface.

12. The container assembly according to claim 9, wherein the inner surface of the side wall of the container closure defines one of a projection and a recess, wherein the outer surface of the side wall of the container defines the other of the projection and the recess, and wherein the projection is disposed in the recess.

13. The container assembly according to claim 9, wherein an outer surface of the side wall of the container includes printed indicia.

14. The container assembly according to claim 9, wherein the inner surface of the end wall of the container is conically-pitched according to an angle toward the central portion of the end wall of the container, and wherein the central portion of the end wall of the container is aligned with a central axis extending through an axial center of the container assembly.

15. A method for utilizing the container assembly of claim 9, comprising the steps of:
    disposing a fluid within the fluid reservoir of the container;
    from surrounding atmosphere, interfacing a syringe with the container closure by:
        axially-aligning the syringe with the syringe-engaging portion of the container closure,
        connecting a distal end of the syringe to the syringe-engaging portion of the container closure, and
        utilizing a distal tip of the syringe for penetrating the disk-shaped member to permit fluid communication between a fluid reservoir of the syringe and the fluid-flow passage that is in fluid communication with the fluid reservoir that contains the fluid; and
    actuating the syringe for withdrawing an amount of the fluid from the fluid reservoir.

16. The method according to claim 15, wherein the syringe-engaging portion is a syringe-receiving bore, and wherein the connecting step includes:
    inserting the distal end of the syringe into the syringe-receiving bore.

17. The method according to claim 15, wherein the syringe-engaging portion is a cylindrical tube-shaped member extending away from the outer surface of the end wall of the container closure, wherein the cylindrical tube-shaped member includes an outer threaded surface that is sized for receiving an inner threaded surface portion of a syringe, and wherein the connecting step includes:

rotating the syringe relative to the cylindrical tube-shaped member for threadingly connecting the inner threaded surface portion of a syringe to the outer threaded surface of the cylindrical tube-shaped member.

18. The method according to claim 15, wherein, prior to the interfacing step, further comprising the step of:
removing a cover member from the outer surface of the end wall of the container closure for permitting access to the syringe-engaging portion.

19. The method according to claim 15, wherein, prior to the interfacing step, further comprising the steps of:
axially-aligning the syringe that is attached to a needle hub that is attached to a needle with a needle sheath member defining a needle-receiving passage and a needle hub-receiving bore;
inserting the needle into the needle-receiving passage and arranging the needle hub within the needle hub-receiving bore; and
disconnecting the needle hub from the distal end of the syringe and docking the needle in needle sheath member.

20. The method according to claim 19, wherein, after the actuating step, further comprising the steps of:
axially-aligning the distal end of the syringe with the needle hub-receiving bore;
attaching the distal end of the syringe to the needle hub; and
withdrawing the needle from the needle-receiving passage and the needle hub from the needle hub-receiving bore.

21. The portion of the container assembly according to claim 1, wherein the syringe-engaging portion is a syringe-receiving bore, and wherein the syringe-receiving bore is sized for receiving a distal end of a syringe.

22. The portion of the container assembly according to claim 21, wherein the syringe-receiving bore is formed in the outer surface of the end wall, and wherein the syringe-receiving bore is aligned with a central axis extending through the container closure.

23. The portion of the container assembly according to claim 21, wherein the syringe-receiving bore is formed in the outer surface of the side wall, and wherein the syringe-receiving bore is arranged perpendicularly with respect to a central axis extending through the container closure.

24. The portion of the container assembly according to claim 23, wherein the fluid-drawing member includes a radial segment and an axial segment, wherein the radial segment is integral with and extends in a radial direction toward the central axis from the inner surface of the side wall of the container closure, and wherein the radial segment is connected to the axial segment that is aligned with the central axis.

25. The portion of the container assembly according to claim 1, wherein the syringe-engaging portion is a cylindrical tube-shaped member extending away from the outer surface of the end wall of the container closure, and wherein the cylindrical tube-shaped member includes an outer threaded surface that is sized for receiving an inner threaded surface portion of a syringe.

26. The portion of the container assembly according to claim 25, wherein the cylindrical tube-shaped member is recessed within a bore formed in the outer surface of the end wall of the container closure.

27. The portion of the container assembly according to claim 25, wherein the cylindrical tube-shaped member is aligned with a central axis extending through the container closure.

28. The portion of the container assembly according to claim 1, wherein at least a portion of the fluid-flow passage is aligned with an axial center of the fluid-drawing member.

29. The portion of the container assembly according to claim 1 further comprising:
a disk-shaped member including a slit, wherein the disk-shaped member is disposed upon and supported by one or more of a shoulder surface and an axial wall surface defining the syringe-engaging portion.

30. The portion of the container assembly according to claim 29, wherein the disk-shaped member is secured to one or more of the shoulder surface and the axial wall surface by an adhesive connection.

31. The portion of the container assembly according to claim 29, wherein the disk-shaped member is secured to one or more of the shoulder surface and the axial wall surface by a friction-fit connection.

32. The portion of the container assembly according to claim 29, wherein the disk-shaped member includes a foam or rubber material.

33. The portion of the container assembly according to claim 1 further comprising:
a pair of spaced-apart cover-retaining members extending from the outer surface of the end wall of the container closure, wherein the pair of spaced-apart cover-retaining members includes a first cover-retaining member and a second cover-retaining member; and
a cover member that is selectively disposed upon and supported by outer surface of the end wall of the container closure, wherein the cover member is selectively retained to the container closure by the pair of spaced-apart cover-retaining members.

34. The portion of the container assembly according to claim 33, wherein the cover member isolates the syringe-engaging portion from surrounding atmosphere when the cover member is selectively disposed upon and supported by the outer surface of the end wall of the container closure.

35. The portion of the container assembly according to claim 33, wherein each cover-retaining member of the pair of cover-retaining members includes an axial surface portion and a radial surface portion, wherein the axial surface portion of the first cover-retaining member is spaced apart from the axial surface portion of the second cover-retaining member to define a width gap having a width dimension, wherein the radial surface portion of each of the first cover-retaining member and the second cover-retaining member is spaced apart from the outer surface of the end wall of the container closure to define a height gap having a height dimension, wherein the cover member includes a width dimension extending between opposite side surfaces of the cover member, wherein the cover member also includes a height dimension extending between a lower surface and an upper surface of the cover member, wherein the width dimension of the cover member is less than the width dimension of the gap extending between the axial surface portions of the first cover-retaining member and the second cover-retaining member, and wherein the height dimension of the cover member is less than the height dimension of the gap extending between the radial surface portion of each of the first cover-retaining member and the second cover-retaining member and the outer surface of the end wall of the container closure.

* * * * *